(12) United States Patent
Dawson et al.

(10) Patent No.: US 10,366,624 B2
(45) Date of Patent: Jul. 30, 2019

(54) DIFFERENTIALLY WEIGHTED MODIFIABLE PRESCRIBED HISTORY REPORTING APPARATUS, SYSTEMS, AND METHODS FOR DECISION SUPPORT AND HEALTH

(71) Applicant: RESCON LTD, Crondall (GB)

(72) Inventors: Thomas Andrew Dawson, Hampshire (GB); Laura Miranda Gilbert, Hampshire (GB); Ioannis Tsitsonis, Surrey (GB)

(73) Assignee: RESCON LTD, Crondall (GB)

( * ) Notice: Subject to any disclaimer, the term of this patent is extended or adjusted under 35 U.S.C. 154(b) by 385 days.

(21) Appl. No.: 15/190,059

(22) Filed: Jun. 22, 2016

(65) Prior Publication Data

US 2016/0379511 A1    Dec. 29, 2016

Related U.S. Application Data

(60) Provisional application No. 62/183,732, filed on Jun. 23, 2015.

(51) Int. Cl.
| | |
|---|---|
| *G06F 19/00* | (2018.01) |
| *G16H 10/00* | (2018.01) |
| *G09B 7/08* | (2006.01) |
| *G06T 11/20* | (2006.01) |
| *G16H 50/20* | (2018.01) |
| *G16H 15/00* | (2018.01) |
| *G06F 3/0488* | (2013.01) |
| *G06F 3/0484* | (2013.01) |

(52) U.S. Cl.
CPC ............. *G09B 7/08* (2013.01); *G06T 11/206* (2013.01); *G16H 15/00* (2018.01); *G16H 50/20* (2018.01); *G06F 3/04847* (2013.01); *G06F 3/04886* (2013.01); *G06T 2200/24* (2013.01); *G06T 2210/41* (2013.01)

(58) Field of Classification Search
CPC . G06F 19/00; G06F 3/00; G06F 17/00; G06F 3/048; G06Q 30/00; G16H 10/00
See application file for complete search history.

(56) References Cited

U.S. PATENT DOCUMENTS

| | | | |
|---|---|---|---|
| 2006/0089543 A1* | 4/2006 | Kim | A61B 5/00 600/300 |
| 2012/0158616 A1* | 6/2012 | Verstandig | G06Q 30/02 706/11 |

(Continued)

*Primary Examiner* — Hugo Molina
(74) *Attorney, Agent, or Firm* — Chad D Tillman; Jeremy C Doerre; Tillman Wright, PLLC

(57) ABSTRACT

Apparatus, systems, and methods of health reporting are disclosed that enhance decision support and provide alerts when health deterioration or the need for intervention has been detected. Embodiments utilize combined pictorial representations (including physical, mental, and social health determinants) as an avatar or pictogram, comparing health status to a general or target population, and using different methods to represent and reinforce health status. The apparatus, systems, and methods further enable individuals to access their own medical records in a way that can be understood by them and therefore is more widely accessible. The invention enhances health reporting, improving utility, usability and desirability of health reporting tools.

15 Claims, 96 Drawing Sheets

(56) References Cited

U.S. PATENT DOCUMENTS

| | | | | |
|---|---|---|---|---|
| 2014/0046680 A1* | 2/2014 | Wentz | G16H 50/30 | 705/2 |
| 2014/0114680 A1* | 4/2014 | Mills | G16H 50/30 | 705/2 |
| 2014/0316856 A1* | 10/2014 | Williams | G06Q 30/02 | 705/7.32 |
| 2015/0024360 A1* | 1/2015 | Mantynen | G06F 19/3481 | 434/257 |
| 2015/0066814 A1* | 3/2015 | Allen | G06N 5/041 | 706/11 |
| 2015/0351655 A1* | 12/2015 | Coleman | A61B 5/0482 | 600/301 |
| 2015/0364057 A1* | 12/2015 | Catani | G09B 19/0092 | 434/127 |
| 2016/0019858 A1* | 1/2016 | Wang | G09G 5/18 | 345/520 |
| 2017/0080346 A1* | 3/2017 | Abbas | A63F 13/825 | |
| 2017/0147775 A1* | 5/2017 | Ohnemus | G16H 50/30 | |

* cited by examiner

Frequency (reminders)

Length of Evaluation: 2 weeks

| Day | | Week | |
|---|---|---|---|
| ☑ | 7-10 | ☑ | M |
| ☐ | 10-12 | ☑ | T |
| ☐ | 12-3 | ☑ | W |
| ☐ | 3-6 | ☑ | T |
| ☑ | 6-9 | ☑ | F |
| ☐ | 9-7 | ☑ | S |
| | | ☑ | S |

MODE OF REMINDER
- ☑ SMS
- ☐ Phone
- ☐ Email
- ☑ In System

1700

FIG. 17 fatigue anxiety social life

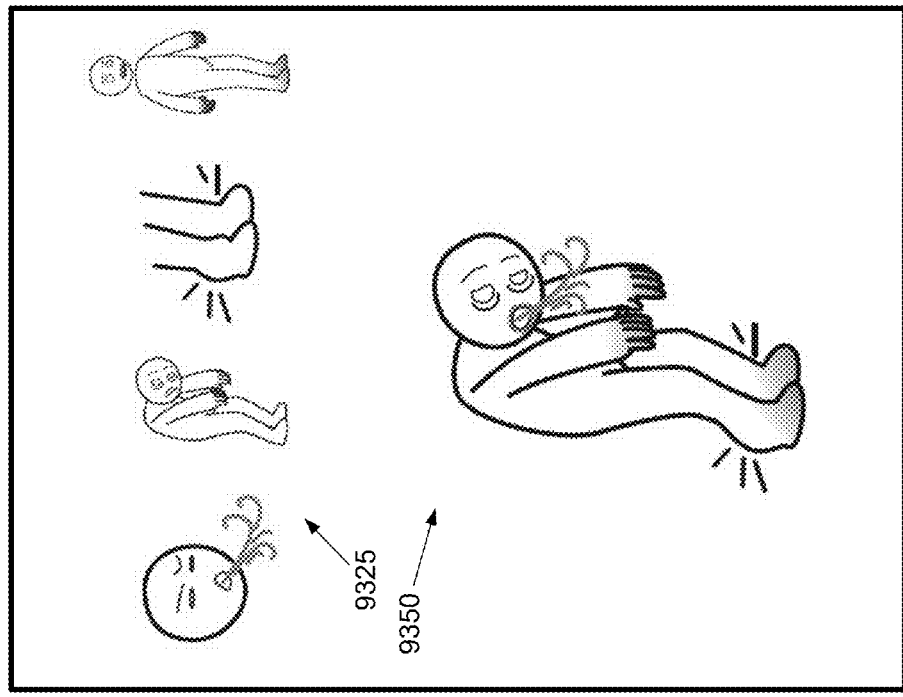
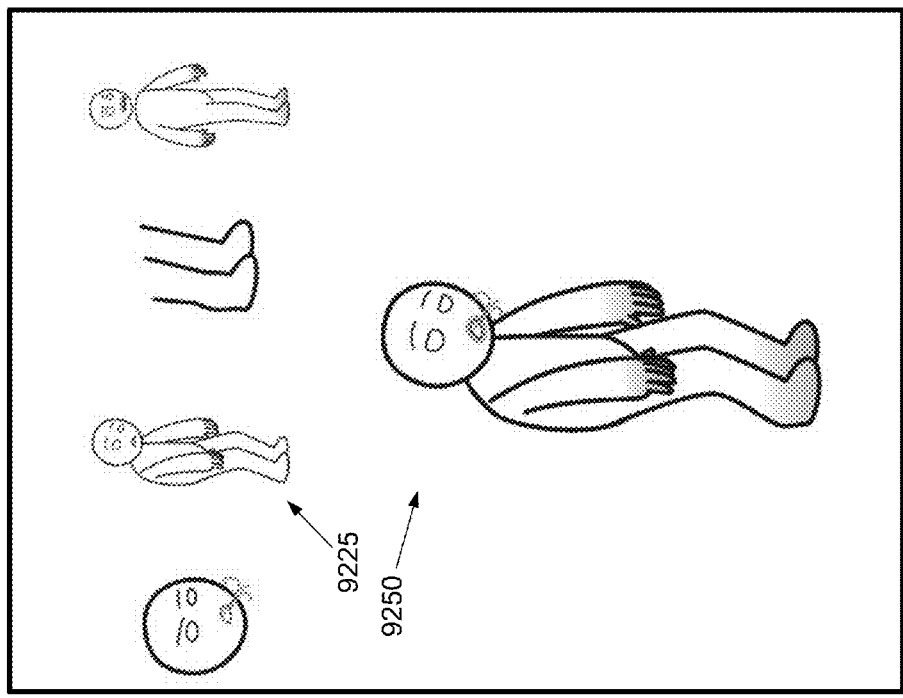

FIG. 102

Content Administration

View/Edit Articles

| ID | Title | Summary | Type | Date Added | User | Last Edit | By | Action |
|---|---|---|---|---|---|---|---|---|
| 1032 | Psoriatic Arthritis | Psoriatic arthritis is a rare form of arthritis with similar... | Text | 2016-04-19 1:59 | Max Wood | 2016-05-19 11:59 | Admin User | |
| 1031 | Ultrasound Scans | This article provides a concise but informative description... | Text | 2016-02-15 4:25 | Max Wood | 0001-01-01 00:01 | N/A | |
| 1030 | X-Rays | X-Rays are a common procedure used to help diagnose medical... | Text | 2016-01-03 17:11 | Max Wood | 0001-01-01 00:01 | N/A | |
| 1029 | MRI Scans | Individuals may feel anxious before having an MRI scan, espe... | Text | 2016-01-28 12:17 | Max Wood | 0001-01-01 00:01 | N/A | |
| 1028 | CT Scans | Having any form of imaging diagnostic procedure can be stre... | Text | 2016-02-25 1:56 | Max Wood | 0001-01-01 00:01 | N/A | |

DIFFERENTIALLY WEIGHTED MODIFIABLE PRESCRIBED HISTORY REPORTING APPARATUS, SYSTEMS, AND METHODS FOR DECISION SUPPORT AND HEALTH

COPYRIGHT STATEMENT

For purposes of the United States, this patent application claims the benefit under 35 U.S.C. § 119 to U.S. provisional patent application 62/183,732 filed on Jun. 23, 2015, the disclosure of which is incorporated herein by reference. For purposes of all other countries and regions, this patent application claims the benefit under the Paris Convention to U.S. provisional patent application 62/183,732 filed on Jun. 23, 2015, the disclosure of which is incorporated herein by reference.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

Current health reporting apparatus, systems, and methods provide individuals with the ability to capture and analyze relevant information about their health, with many platforms integrating wireless devices and feedback into an overall healthcare system. Such apparatus, systems, and methods further may be targeted towards specific groups, or health conditions, while others may provide more general health tracking capabilities, and an individual's use of such apparatus, systems, and methods is often in conjunction with family, community, and healthcare professionals.

Furthermore, there are multiple determinants of human health and wellbeing. The contemporary medical model focuses on physical aspects, with the majority of spend and human resource being targeted to this area. The remainder targets mental aspects of human health, with a small amount addressing social health, including emotional health. It has been increasingly recognized that social determinants of health are extremely important, with metrics such as "loneliness" in the elderly being tightly correlated to hospital admissions. Mental health also is very important and has a major impact on society in direct and indirect costs, such as time off from work. Accordingly, it is believed that not only physical determinants but mental and social determinants increasingly should be taken into consideration in healthcare any health reporting apparatus, systems, and methods should include health reporting with respect to not only physical determinants, but also mental and social determinants.

Moreover, enabling individuals to capture and analyze relevant information about their health is believed to enhance health knowledge and promote symptom management, treatment, and beneficial lifestyle change by such individuals. In turn, this is believed to be important in reducing strain on healthcare systems and improving overall quality of life. Indeed, given that most individuals spend limited time with healthcare professionals, such individuals themselves actually are their own primary healthcare providers, each being responsible for the vast majority of his or her healthcare. As such, there is a need for the healthcare industry worldwide—primarily reactive and disease focused—to shift focus from outpatient appointments to supporting individuals in managing their own healthcare. Such transformation is believed vital in order to cope with a growing burden of chronic health conditions worldwide.

An individual's use of health reporting apparatus, systems, and methods further enhances overall health reporting for use by professional healthcare providers in supporting decision making. Indeed, such use by an individual builds a record of that individual's health and care over time, and overcomes issues relating to the accuracy of information recall such individuals when informing professional healthcare providers during patient encounters. Indeed, patient memory for medical information is often inaccurate and poor, especially if the patient is old or anxious. Without accurate recall and transcription of events, the accuracy of medical diagnosis and appropriate intervention can be compromised. In addition, physicians rely on patient feedback on efficacy of interventions, reporting of adverse effects, and progression of disease. Due to treatment and individual variability, the response to any one intervention is variable, and thus, the feedback can be extremely important. This is especially true in view of the limited time an individual spends with professional healthcare providers.

Fortunately, adoption of such use is easier than before due to advances in—and the increasing popularity of—mobile technology including mobile phones. Such mobility enables frequent data collection independent of time and place. And current health reporting apparatus, systems, and methods are evolving. For example, recent, conventional health reporting apparatus, systems, and methods enable perceptual health reporting generally utilizing words, phrases, icons, and combinations thereof. A patent disclosing such conventional apparatus, systems, and methods is U.S. Pat. No. 8,941,659 B1, which is incorporated herein by reference.

Other recent, conventional health reporting apparatus, systems, and methods gather data from wearable devices including activity trackers and heart rate monitors; health and wellbeing devices, such as blood pressure monitors, glucometers or scales; or environmental devices, such as switches, movement sensors, door sensors, and temperature sensors. Some apparatus, systems, and methods enable tagging of events and interventions, or factors, that provide for identification of the impact they may have on health and wellbeing; some apparatus, systems, and methods enable detection of changes in health, assistance in identifying appropriate interventions, and determinations of whether interventions have been effective or not; and some apparatus, systems, and methods learn from user input to provide personalized feedback, such feedback including alerts when health deterioration has been detected—often through a change in pattern or behavior, alerts when intervention may be required, or both. Apparatus, systems, and methods also analyze and present collected data through a variety of data output methods, including graphs, raw numbers, and averages. In many cases, data is displayed in a visual output, with some tools also enabling advanced data views. While considered beneficial, such feedback and data can be difficult to understand, interpret, or act upon by users and, thus, it is believed that the full benefit has not been realized in practice. Moreover, barriers exist to the widespread adoption and effectiveness of use by everyone of health reporting apparatus, systems, and methods. Such barriers include health literacy levels, computer literacy levels, and reading literacy levels.

In view of the foregoing, it is believed that needs exist for improvements in health reporting apparatus, systems, and methods, including a need for such apparatus, systems, and methods that better engage individuals for making such apparatus, systems, and methods more effective in enhancing decision making and the provision of care, both by the individuals themselves and by professional healthcare providers; and a need for overcoming the aforementioned literacy barriers thereby enabling wider accessibility of health information to enhance health knowledge and self-care, and reduce strain on the healthcare system.

One or more aspects and features of the invention are believed to represent improvements in health reporting apparatus, methods, and systems. One or more preferred embodiments are believed to increase accessibility to, and provide better and intuitive representations and corresponding understanding of, health and wellbeing data of an individual by that individual, leading to ownership and control over that individual's health, improving self-care, and thereby leading to better health outcomes.

SUMMARY OF THE INVENTION

The present invention generally relates to apparatus, systems, and methods relating to a person's health and wellbeing, and more particularly relates to health reporting apparatus, systems, and methods in which a person's health and wellbeing are monitored and recorded. The present invention includes many aspects and features of such apparatus, systems, and methods.

In an aspect of one or more methods, apparatus, and systems of the present invention, a method for visualization of a quantitative overall health of an individual based on mental, social, and physical determinants of the individual comprises the steps of: receiving input representative of one or more mental determinants of overall health of the individual, the input received for each respective mental determinant representing one out of three or more predefined inputs corresponding to a range of progression between one or more worst case scenarios, and one or more best case scenarios, for such respective mental determinant, each predefined input being linked to a predefined value; receiving input representative of one or more social determinants of overall health of the individual, the input received for each respective social determinant representing one out of three or more predefined inputs corresponding to a range of progression between one or more worst case scenarios, and one or more best case scenarios, for such respective social determinant, each predefined input being linked to a predefined value; receiving input representative of one or more physical determinants of overall health of the individual, the input received for each respective physical determinant representing one out of three or more predefined inputs corresponding to a range of progression between one or more worst case scenarios, and one or more best case scenarios, for such respective physical determinant, each predefined input being linked to a predefined value; and, based on the linked predefined values of the received input representative of the mental, social, and physical determinants, determining, using an electronic device, a pictorial representation of the overall health of the individual out of a plurality of predefined pictorial representations, wherein the linked predefined values are utilized in an equation incorporated into computer-executable instructions that are executed by a processor of the electronic device.

In features of this aspect, the method further comprises displaying, on the electronic device or a different electronic device, the determined pictorial representation of the individual. Moreover, the pictorial representation may be displayed, for example, as holograms, tactile visualizations utilizing ultrasound waves, within virtual reality environments and displays, and on projector screens.

In another feature, the step of determining the pictorial representation of the overall health of the individual out of a plurality of predefined pictorial representations includes weighting one or more of the linked values relative to each other. The weighting may be selected by the individual, by a professional healthcare provider, by a healthcare organization, or by a group of individuals. The weighting also may be determined based on machine learning, or any combination thereof. Furthermore, the method may further comprise maintaining a profile of the individual, and the weighting may be based, at least in part, on the profile of the individual that is maintained. In this regard, the profile preferably includes medical information of the individual, a medical history of the individual, information acquired from an electronic health record of the individual, and combinations thereof.

This profile also can be composed of other features that relate to the behavior of the individual, such as the choices made within an environment, including how the individual might rate the outcomes of the choices made. The combination of the choices of groups of individuals with similar features also can be utilized to inform an individual's predicted decision-making or behavior profile, and this may be utilized to customize that individual's experience in combination with the system learning the individual's ongoing decision-making activity, choices and ratings.

In another feature, the method further comprises the step of maintaining a profile of the individual, wherein the determining of the pictorial visualization is based at least in part on the profile of the individual that is maintained.

In another feature, the received input representative of a mental or social determinant of overall health of the individual results from the taking of a survey by the individual. The survey may be taken by the individual on the electronic device, or the survey may be taken by the individual on a different electronic device.

In another feature, the received input representative of a physical determinant of overall health of the individual is communicated from an electronic sensor that acquires data pertaining to the physical determinant. The electronic sensor may be worn by the individual, or may be part of a device that is used by the individual, such as a scale, an exercise machine, a phone (e.g., iPhone), or a watch (e.g., Apple watch).

In another feature, the step of determining the pictorial representation of the overall health of the individual out of a plurality of predefined pictorial representations includes: determining a first pictorial visualization corresponding to the received input representative of the one or more mental determinants of overall health of the individual, wherein the first pictorial visualization is one out of a set of pictorial visualizations corresponding to a range of progression between one or more best case scenarios, and one or more worst case scenarios, of the one or more mental determinants of overall health of the individual; determining a second pictorial visualization corresponding to the received input representative of the one or more social determinants of overall health of the individual, wherein the second pictorial visualization is one out of a set of pictorial visualizations corresponding to a range of progression between one or more best case scenarios, and one or more worst case scenarios, of the one or more social determinants of overall health of the individual; determining a third pictorial visualization corresponding to the received input representative of the one or more physical determinants of overall health of the individual, wherein the third pictorial visualization is one out of a set of pictorial visualizations corresponding to a range of progression between one or more best case scenarios, and one or more worst case scenarios, of the one or more physical determinants of overall health of the individual, and combining the determined first, second, and third pictorial visualizations into a composite pictorial visualization to form the pictorial representation of the overall health of the individual. In this regard, the method further may comprise displaying, on the electronic device, or through other display means, the determined first pictorial representation upon receipt of input representative of the one or more mental determinants, the determined second pictorial representation upon receipt of input representative of the one or more social determinants, the determined third pictorial representation upon receipt of input representative of the one or more physical determinants. Furthermore, each of the input representative of the one or more mental determinants, the input representative of the one or more social determinants, and the input representative of the one or more physical determinants may be received through a user interface of the electronic device. The method also may further comprise displaying the composite pictorial visualization on the electronic device for view by the user, communicating the composite pictorial visualization from the electronic device for view by others, or both. For example, the composite pictorial visualization may be displayed to others by way of a social networking website or app (e.g., Facebook), other communication device or application (e.g., FaceTime or Skype), or combinations thereof.

In other features of this aspect, the method further comprises identifying the individual as being at risk for suicide based on the pictorial representation that is determined; identifying the individual as being recommended for hospital admission based on the pictorial representation that is determined; identifying the individual as being recommended for hospital admission based on the pictorial representation that is determined; identifying the individual as being prone toward domestic violence based on the pictorial representation that is determined; identifying the individual as experiencing heart failure based on the pictorial representation that is determined; and combinations thereof.

In another aspect, an apparatus used in monitoring health and wellbeing of a person comprises: a display; one or more user inputs for receiving input from the person; machine readable medium; a processor; and computer readable instructions contained in non-transitory computer readable medium which, when executed by the processor, perform a method comprising repeating, over a period of time, the steps of: receiving input representative of one or more mental determinants of overall health of the individual, the input received for each respective mental determinant representing one out of three or more predefined inputs corresponding to a range of progression between one or more worst case scenarios, and one or more best case scenarios, for such respective mental determinant, each predefined input being linked to a predefined value; receiving input representative of one or more social determinants of overall health of the individual, the input received for each respective social determinant representing one out of three or more predefined inputs corresponding to a range of progression between one or more worst case scenarios, and one or more best case scenarios, for such respective social determinant, each predefined input being linked to a predefined value; receiving input representative of one or more physical determinants of overall health of the individual, the input received for each respective physical determinant representing one out of three or more predefined inputs corresponding to a range of progression between one or more worst case scenarios, and one or more best case scenarios, for such respective physical determinant, each predefined input being linked to a predefined value; and, based on the linked predefined values of the received input representative of the mental, social, and physical determinants, determining a pictorial representation of the overall health of the individual out of a plurality of predefined pictorial representations, wherein the linked predefined values are utilized in an equation incorporated into computer-executable instructions executed by the processor of the apparatus.

In another aspect, a system for monitoring health and wellbeing of a plurality of persons comprises a plurality of computing devices, each used by a respective person whose health and wellbeing are monitored. Each computing device comprises: a display; one or more user inputs for receiving input from the person; machine readable medium; a processor; and computer readable instructions contained in computer readable medium which, when executed by the processor, perform a method comprising repeating, over a period of time, the steps of: receiving input representative of one or more mental determinants of overall health of the individual, the input received for each respective mental determinant representing one out of three or more predefined inputs corresponding to a range of progression between one or more worst case scenarios, and one or more best case scenarios, for such respective mental determinant, each predefined input being linked to a predefined value, receiving input representative of one or more social determinants of overall health of the individual, the input received for each respective social determinant representing one out of three or more predefined inputs corresponding to a range of progression between one or more worst case scenarios, and one or more best case scenarios, for such respective social determinant, each predefined input being linked to a predefined value; receiving input representative of one or more physical determinants of overall health of the individual, the input received for each respective physical determinant representing one out of three or more predefined inputs corresponding to a range of progression between one or more worst case scenarios, and one or more best case scenarios, for such respective physical determinant, each predefined input being linked to a predefined value, and, based on the linked predefined values of the received input representative of the mental, social, and physical determinants, determining a pictorial representation of the overall health of the individual out of a plurality of predefined pictorial representations, wherein the linked predefined values are utilized in an equation incorporated into computer-executable instructions executed by the processor of the apparatus. The system further comprises one or more computing devices configured to receive the communicated data from the plurality of computing devices of the persons, and to store the received data such that the data is accessible later for processing of the data.

In another aspect, a combinatorial, pictorial visualization representative of the health and wellbeing of a person is determined. A method of such determination comprises the steps of: (a) receiving first input representative of a first one of a plurality of health and wellbeing factors (a first determinant), and determining a pictorial visualization corresponding to the received first input from a first set of predefined pictorial visualizations for the first one of the plurality of health and wellbeing factors, the first set of pictorial visualizations representing a progression between a best case scenario, or scenarios, and a worst case scenario, or scenarios, for the first one of the plurality of health and wellbeing factors; (b) receiving second input representative of a second one of a plurality of health and wellbeing factors (a second determinant), and determining a pictorial visualization corresponding to the received second input from a second set of predefined pictorial visualizations for the second one of the plurality of health and wellbeing factors, the second set of pictorial visualizations representing a progression between best case scenario, or scenarios, and a worst case scenario, or scenarios, for the second of the plurality of health and wellbeing factors; and (c) combining the determined pictorial visualizations into a composite pictorial visualization.

In a feature, the method further comprises electronically displaying the composite pictorial visualization on an electronic display. The composite pictorial visualization preferably is displayed to the person. Furthermore, a second composite pictorial visualization may be displayed to the person, wherein the second composite pictorial visualization is: for another person; for the same person, but at a different time; or for an average person of a defined population, against which the person is being compared. Further in this respect, the predefined population may comprise a predefined group of people of the same culture; a predefined group of people of the same socioeconomic status; a predefined group of people of the same learning difficulties; a predefined group of people with high risks regarding a particular health condition or disease; or a predefined group of people with one or more common characteristics.

In additional various features, the composite pictorial visualization comprises an avatar, which avatar may be derived from a picture, video, or three dimensional scan of the person, or may be derived from another real-life or previously alive or mythical person or character; a combined pictorial visualization is displayed on a video screen during a conversation between two or more individuals in order to enhance communication amongst the individuals, which video screen may comprise an augmented reality display built into glasses or a contact lens or other method of projecting data; a combined pictorial visualization is displayed on social media for sharing with selected individuals, such as family, friends, or caregivers, groups of individuals, or the entire social network of the individual; a combined pictorial visualization is displayed for public view; each composite pictorial visualization comprises an avatar that changes based on changes in input; and the composite pictorial visualization is displayed to a healthcare professional for enhanced clinical decision support.

In another feature, the method further comprises receiving third input representative of a third one of a plurality of health and wellbeing factors (a third determinant), and determining a pictorial visualization corresponding to the received third input from a third set of predefined pictorial visualizations for the third one of the plurality of health and wellbeing factors, the third set of pictorial visualizations representing a progression between a best case scenario and a worst case scenario for the third of the plurality of health and wellbeing factors; and further combining the determined pictorial visualization into the composite pictorial visualization that is displayed to the person.

In still additional features, the method further comprises displaying to the person the determined pictorial visualization corresponding to the received first input when receiving the first input such that a degree, level, or extent of the first one of the plurality of health and wellbeing factors is pictorially represented in the display; the method further comprises recording the composite pictorial visualization in non-transitory computer readable medium for later access, including for later display and reporting; and the method further comprises recording a chronological sequence of composite pictorial visualizations of the person in non-transitory computer readable medium; accessing the chronological sequence of composite pictorial visualizations; and displaying one or more of the composite pictorial visualizations of the sequence to the person.

In more features: the first input and the second input each is received from an electronic device; the first input and the second input each is received through a user interface of an electronic device; the first input and the second input each is received through a user control of a user interface of an electronic device; the first input and the second input each is received through a slider control of a user interface of an electronic device; the steps are performed on a mobile electronic device that is configured with software for performing the method; the steps are performed on a tablet that is configured with software for performing the method; the steps are performed on a smartphone that is configured with software for performing the method; the steps are performed on a personal computing device that is configured with software for performing the method; the steps are performed on a wrist-mounted personal electronic device that is configured with software for performing the method; the steps are performed on a personal electronic wearable device that is configured with software for performing the method; the first input and the second input each comprises user input; at least one of the first input and the second input comprises input from a sensor; the plurality of health and wellbeing factors comprise physical, mental, and social factors; the plurality of health and wellbeing factors pertain to coughing, swollen ankles, fatigue, and cyanosis, wherein the composite pictorial visualization may be used an indicator of heart failure of the person; the plurality of health and wellbeing factors pertain to alcohol or substance abuse, job satisfaction, home situation, and activity, wherein the composite pictorial visualization may be used an indicator of likelihood of domestic violence; the plurality of health and wellbeing factors pertain to feeling supported, pertain to mood, pertain to self-image, pertain to activity as self-assessed or measured by a wearable electronic device, pertain to feelings of control, and combinations thereof, wherein the composite pictorial visualization may be used as an indicator of suicide risk; the plurality of health and wellbeing factors pertain to discomfort, loneliness, itchiness, and shortness of breath, wherein the composite pictorial visualization may be used as an indicator of likelihood of hospital admission; wherein the plurality of health and wellbeing factors pertain to organ system function, such as brain, lung, heart, nerve, kidney, liver, intestinal, bladder, skin, musculoskeletal and vascular systems, wherein the composite pictorial visualization may be used as an indicator of overall health; the method further comprises electronically communicating the composite pictorial visualization to a healthcare provider; each composite pictorial visualization consists of no words; and, the method further comprises generating one or more alerts based on the composite pictorial visualization.

In yet additional features, the method further comprises electronically communicating the composite pictorial visualization to, and recording the composite pictorial visualization in, an electronic healthcare record of the person. The composite pictorial visualizations recorded in the person's electronic healthcare record may be made electronically accessible for generating a history or comparison of the health and wellbeing of the person over time; and may be made electronically accessible and used to facilitate self, professional or automated decision making, support, audit, or guidance.

In additional aspects, a health reporting apparatus performs the method of any of the foregoing; and a health reporting system incorporates the method of any of the foregoing claims.

In still another aspect, an apparatus used in monitoring health and wellbeing of a person comprises: a display; one or more user inputs for receiving input from the person; machine readable medium; a processor; and computer readable instructions contained in computer readable medium which, when executed by the processor, perform a method comprising repeating, over a period of time, the steps of: (i) receiving first input representative of a first one of a plurality of health and wellbeing factors and determining a pictorial visualization corresponding to the received first input from a first set of pictorial visualizations for the first one of the plurality of health and wellbeing factors, the first set of pictorial visualizations representing a progression between best and worst for the first one of the plurality of health and wellbeing factors; (ii) receiving second input representative of a second one of a plurality of health and wellbeing factors and determining a pictorial visualization corresponding to the received second input from a second set of pictorial visualizations for the second one of the plurality of health and wellbeing factors, the second set of pictorial visualizations representing a progression between best and worst for the second of the plurality of health and wellbeing factors; (iii) combining the determined pictorial visualizations into a composite pictorial visualization; and (iv) displaying the composite pictorial visualization on the display.

In various features, the display and the user input are components of a touch screen; the apparatus comprises a consumer electronic device; the apparatus comprises a handheld consumer electronic device; the apparatus is portable; the apparatus is handheld; the apparatus is wearable; data regarding each composite pictorial visualization is electronically recorded such that it is accessible later for generating a history of the health and wellbeing of the person over the period of time; the apparatus further comprises a communications component by which the recorded data is communicated from the apparatus to another device, whereat a history is generated of the health and wellbeing of the person over the period of time; and the apparatus further comprises a wireless communications component by which the recorded data is communicated from the apparatus to another device whereat a history is generated of the health and wellbeing of the person over the period of time, wherein the wireless communications component may comprise a radio component.

In another aspect, a system for monitoring health and wellbeing of a plurality of persons comprises: a plurality of computing devices each used by a respective person whose health and wellbeing are monitored, each computing device comprising (a) a display; (b) one or more user inputs for receiving input from the person; (c) machine readable medium; (d) a processor; and (e) computer readable instructions contained in computer readable medium which, when executed by the processor, perform a method comprising repeating, over a period of time, the steps of: (i) receiving first input representative of a first one of a plurality of health and wellbeing factors and determining a pictorial visualization corresponding to the received first input from a first set of pictorial visualizations for the first one of the plurality of health and wellbeing factors, the first set of pictorial visualizations representing a progression between best and worst for the first one of the plurality of health and wellbeing factors; (ii) receiving second input representative of a second one of a plurality of health and wellbeing factors and determining a pictorial visualization corresponding to the received second input from a second set of pictorial visualizations for the second one of the plurality of health and wellbeing factors, the second set of pictorial visualizations representing a progression between best and worst for the second of the plurality of health and wellbeing factors; (iii) combining the determined pictorial visualizations into a composite pictorial visualization; (iv) displaying the composite pictorial visualization on the display; and (v) electronically communicating data regarding the composite pictorial visualization from the computing device. The system further comprises one or more computing devices configured to receive the communicated data from the plurality of computing devices of the persons, and store the received data such that the data is accessible later for processing of the data.

In various features, the one or more computing devices configured to receive the communicated data comprise one or more servers, and the communicated data is received over the Internet; and at least one of the computing devices configured to receive the communicated data is configured to electronically access the stored data and process the accessed data for generating a history of health and wellbeing of the person.

In another aspect, a method for automatically creating a computer-generated composite visualization based on multivariate health data for an individual comprises the steps of: (a) displaying, to a user via a touchscreen display, (i) a first input control displayed in association with a first health question, (ii) a second input control displayed in association with a second health question, and (iii) a third input control displayed in association with a third health question, (iv) wherein the first, second, and third health questions are all related to a first health metric; (b) receiving, from the user via touching of the touchscreen display, first user input corresponding to interaction with the first input control; (c) receiving, from the user via touching of the touchscreen display, second user input corresponding to interaction with the second input control; (d) receiving, from the user via touching of the touchscreen display, third user input corresponding to interaction with the third input control; (e) determining, based on the first user input, a first answer value associated with the first question; (f) determining, based on the second user input, a second answer value associated with the second question; (g) determining, based on the third user input, a third answer value associated with the third question; (h) determining, based on the first answer value associated with the first question, a first score for the first answer by (i) accessing a sentiment value associated with the first question, (ii) calculating the first score for the first answer based on the first answer value and the accessed sentiment value associated with the first question, wherein (A) if the sentiment value is positive, the first score is set to be the first answer value, (B) if the sentiment value is negative, the first score is set to be the difference between the maximum possible first answer value and the input first answer value, and (C) if the sentiment value is zero, the first score is calculated differently based on whether the first answer value was above or below the median possible first answer value; (i) determining, based on the second answer value associated with the second question, a second score for the second answer by (i) accessing a sentiment value associated with the second question, (ii) calculating the second score for the second answer based on the second answer value and the accessed sentiment value associated with the second question, wherein (A) if the sentiment value is positive, the second score is set to be the second answer value, (B) if the sentiment value is negative, the second score is set to be the difference between the maximum possible second answer value and the input second answer value, and (C) if the sentiment value is zero, the second score is calculated differently based on whether the second answer value was above or below the median possible second answer value; (j) determining, based on the third answer value associated with the third question, a third score for the third answer by (i) accessing a sentiment value associated with the third question, (ii) calculating the third score for the third answer based on the third answer value and the accessed sentiment value associated with the third question, wherein (A) if the sentiment value is positive, the third score is set to be the third answer value, (B) if the sentiment value is negative, the third score is set to be the difference between the maximum possible third answer value and the input third answer value, and (C) if the sentiment value is zero, the third score is calculated differently based on whether the third answer value was above or below the median possible third answer value; (k) determining a weighted metric score for the first health metric by (i) accessing weight values associated with the first, second, and third questions, and (ii) calculating the weighted metric score for the health metric utilizing the calculated first, second, and third scores and the accessed weight values; (l) calculating a first image value for the first health metric based on the determined weighted metric score; (m) accessing, from a data store containing a plurality of images associated with the first health metric, each image being associated with an image value, a first component image associated with the first image value; (n) accessing, from a data store containing a plurality of images associated with a second health metric, each image being associated with an image value, a second component image associated with a second image value calculated in the same manner as the first image value; (o) accessing, from a data store containing a plurality of images associated with a third health metric, each image being associated with an image value, a third component image associated with a third image value calculated in the same manner as the first image value; (p) automatically combining the accessed first component image, the accessed second component image, and the accessed third component image to generate the composite visualization; and (q) displaying, to the user via the touchscreen display, the generated composite visualization.

In another aspect, a decision-support, trending, and alerting system for clinical, social, and self-care utilizes quantified self-reported subjective and objective data; quantified observed subjective and objective data; and quantified measured data, all of which relates to the health and wellbeing of individuals and communities.

In a feature, each of a data type and subtype—where than can be several levels of subtypes—are assigned a fixed or modifiable: (a) weighting; (b) error score (generally a range); (c) sentiment (where sentiment is described as negative, positive, neutral, or a combination that is assigned a shape); (d) relevance (tightly associated with weight, where a cough may be highly relevant when associated with an individual with a heart condition, a smoker or someone who is short of breath, but where a cough could be deemed to be not as relevant when an individual has a painful finger, arthritis or was briefly exposed to an irritant); and (e) patterning (tightly associated with weighting, relevance and sentiment and can be either: expert-defined, where an expert can be an individual, committee or association; or computer-defined, where a learning algorithm recognizes a common pattern in an individual or in a group of individuals defined by a commonality or commonalities.

In another feature, the components that relate to the outputs can be automatically weighted by the system dependent of the profile of the user. In features thereof, for individuals with heart failure, "swollen ankles" and "coughing" are more heavily weighted than for a fit athlete; "coughing" over two days is more heavily weighted in an individual with respiratory disease and a history of hospitalization from this; appetite in an individual having a history of suicide attempts is more heavily weighted; and loneliness in an individual having a history of hospitalization is more heavily weighted.

In various additional features, the data is self-reported (such as from online text reporting or picture reporting); is observed (such as by a family member, informal or formal career or medical professional); comes from wearable devices (such as activity trackers and heart rate monitors); comes from health and wellbeing devices (such as blood pressure monitors, glucometers or scales); comes from environmental devices (such as switches, movement sensors, door sensors, temperature sensors); and any combination thereof.

In yet another feature, the impact or prediction of an event or intervention is analyzed by recording the social, mental, and physical health metrics, and used to predict or determine the impact of an event. The impact or prediction further may be visualized in accordance with the present disclosure.

In another aspect, a decision-support, trending, and alerting system for clinical, social, and self-care utilizing quantified self-reported subjective and objective data; observed subjective and objective data; and measured data, all of which pertains to the health and wellbeing of individuals and communities. The subtypes may comprise several levels each. Furthermore, each type of data and subtype of data, if any, preferably are assigned a weighting; an error score or range; a sentiment; a relevance; and a patterning. Any of the weighting, error score or range, sentiment, relevance, and patterning may be fixed or modifiable. The data may self-reported by the individuals, observed by others, received from wearable devices, received from health and wellbeing devices, received from environmental devices, and combinations thereof.

In features, the weighting may be defined by an expert, wherein the expert comprises an individual, committee or association; the weighting may be computer-defined, with a learning algorithm configured to recognize a common pattern in an individual or a group of individuals defined by a commonality or commonalities; the weighting is automatically determined based, in part, on medical information that is maintained in the system in a user profile for each individual; and combinations thereof.

In feature, the sentiment is described as negative, positive, or neutral.

In features, a combination of data types, subtypes, or both are assigned a shape.

The others may include family members, caregivers, and medical professionals; the wearable devices may include activity trackers and heart rate monitors; the health and wellbeing devices may include blood pressure monitors, glucometers, and scales; and the environmental devices may include switches, movement sensors, door sensors, temperature sensors.

The data preferably is recorded to predict or determine the impact or prediction of an event or intervention, and the impact or prediction preferably is visualized using a combined pictorial representation.

In additional features, the data is recorded in an electronic health record (EHR) of the individual, and the data recorded in the EHR is accessed and used in creating the pictorial visualization, which is then displayed to the individual to which the pictorial visualization applies.

In another aspect, a method of displaying an overall health status representing a wellbeing state of an individual, comprises combining pictorial visualizations representing physical, mental, and social health determinants into a composite pictorial visualization, each of the physical, mental, and social determinants being represented by separate pictorial visualizations of the composite pictorial visualization. The combined pictorial visualizations comprise pictograms, each pictogram corresponding to a physical determinant or combination of physical determinants; a mental determinant or combination of mental determinants; or a social determinant or combination of social determinants. Each pictogram preferably corresponds to a numeric value that is used in programmatically determining the composite pictorial visualization.

In features, the method further includes displaying health status in the present, health status in the past, and a health status trend; comparing the overall health status of the individual to an average overall health status of a population of individuals; respectively comparing each of the pictorial visualizations representing physical, mental, and social health determinants of the individual to each of pictorial visualizations representing physical, mental, and social health determinants of an average of a population of individuals; and combinations thereof. Moreover, more than one health status trend may be displayed concurrently for an individual, such as a first health status trend of an individual spanning a week being displayed in conjunction with the display of a first health status trend of the individual spanning a month and a third health status trend of the individual spanning a year. The population may be a general population or a targeted population; colors, external lines, shapes, images, and combinations thereof may be used in the display of the overall health status to represent or reinforce the health status of the individual; and arrows, shading, and combinations thereof may be used in the display of the overall health status to represent health trends of the individual.

In another feature of one or more of the foregoing aspects, profile metrics as a whole or in part, for example activity level, or activity on the system, are used as a point system for real or game environment situations where they may translate to real world benefits such as discounts for shopping or virtual world benefits such as for game points or being assigned to boost the health or status of a game avatar or component of a game.

In another aspect, a health reporting tools provides users with pictorial visualizations of data that change depending on user input. The pictorial visualizations represent combined pictorial representations, each corresponding to one or more social determinants of health; one or more social determinants of health; or one or more physical determinants of health. Furthermore, each of the combined pictorial visualizations may comprise a pictogram regarding the one or more determinants to which the visualization corresponds.

In another aspect, a health monitoring and reporting system provides feedback to individual by combining physical, mental, and social health determinants into a quantitative pictorial visualization that comprises an avatar, that compares health status to a general or target population, and that uses colors, external lines, shapes, or combinations thereof to represent and reinforce health status.

In other aspects, a method, apparatus, and system each includes the provision of health information of an individual in the form of integrated into pictograms for interpretation by individuals having a range of literacy levels.

In other aspects, a method, apparatus, and system each includes the provision of health information from an electronic health record (EHR) of an individual that is integrated into pictograms for interpretation by individuals having a range of literacy levels.

In other aspects, a method, apparatus, and system each uses representations of symptoms in an on-screen pictorial visualization format, including combining physical, mental and social health determinants in a single field of view, and separate components of each; which provides the assignment to symptoms of values, including weighting—whether automatic or by a user, range, sentiment, relevance and patterning; which provides entering such data into electronic health records for the purposes of a decision support, tending and alert system; which provides accessible and intuitive representations of health and wellbeing data, including combined quantitative visualization of physical, mental and social health, use of colors, external lines and shapes, to represent and reinforce health status; and which provides comparison of health status with the general population/target population.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals.

FIGS. 2-5 respectively illustrate a screenshot of a "Home" page, a screenshot of a "Surveys" page, a screenshot of an "Events" page, and a screenshot of a "Measurements" page, all in accordance with a first skin.

FIGS. 6-9 respectively illustrate a screenshot of a "Home" page, a screenshot of a "Surveys" page, a screenshot of an "Events" page, and a screenshot of a "Measurements" page, all in accordance with a second skin.

FIGS. 16 and 17 illustrate interfaces for selecting settings regarding alerts.

FIG. 92 illustrates an individual with a combination of physical factors including coughing, swollen ankles, fatigue and cyanosis, which factors in the illustrated severity indicate mild heart failure.

FIG. 93 illustrates the same combination of factors as those in FIG. 92, but are represented as being severe, which indicates severe heart failure.

Figure 102:
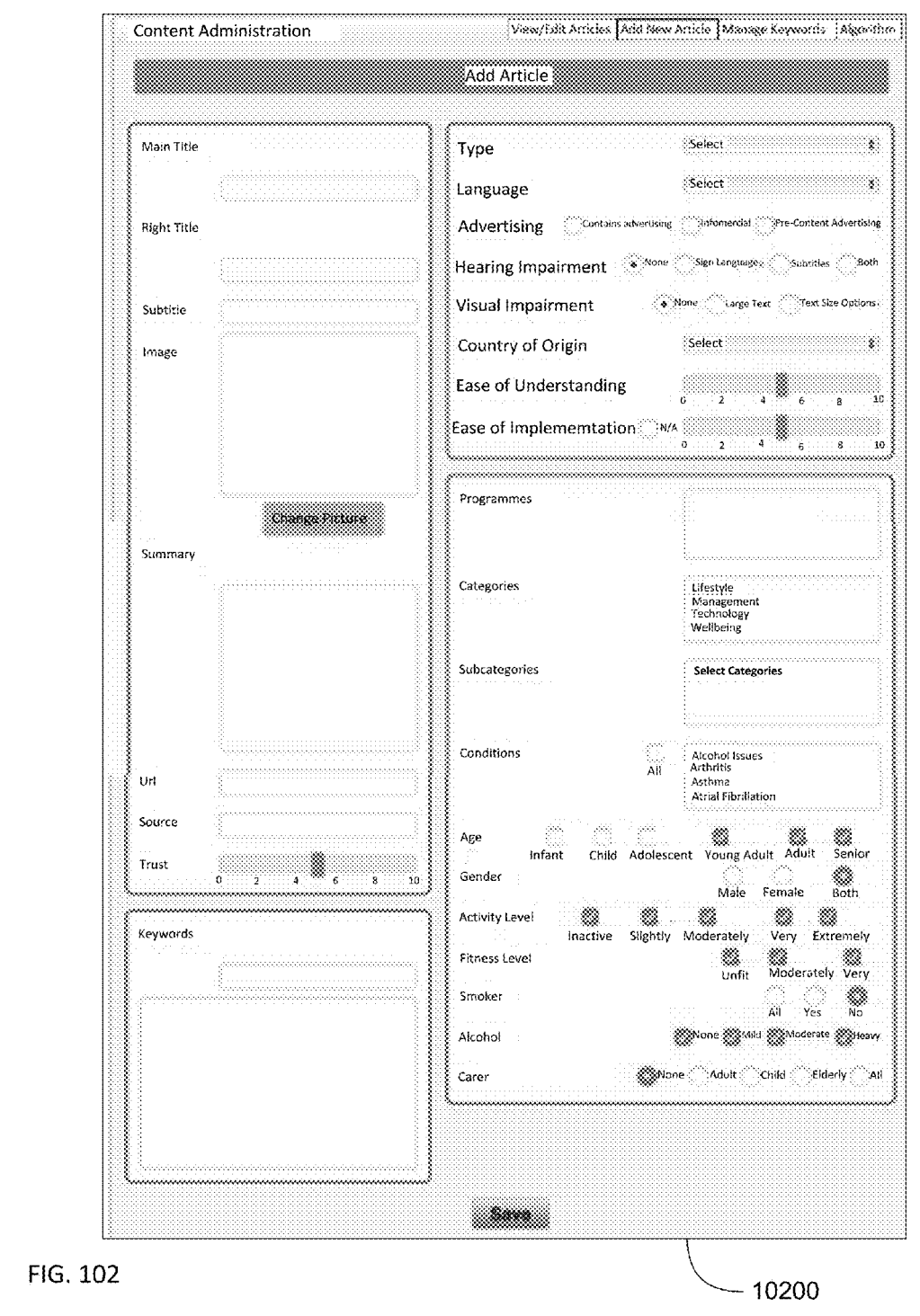

FIG. 102 illustrates an exemplary user interface for adding a new article to curated content for availability for display to users through a personalized recommended content engine and search engine of preferred embodiments of the invention.

FIG. 103 illustrates an exemplary user interface for viewing and editing articles that have been added to the curated content.

FIG. 104 illustrates an exemplary user interface for individuals for searching for and managing content on a personal basis for each such individual.

DETAILED DESCRIPTION

Figure 1:
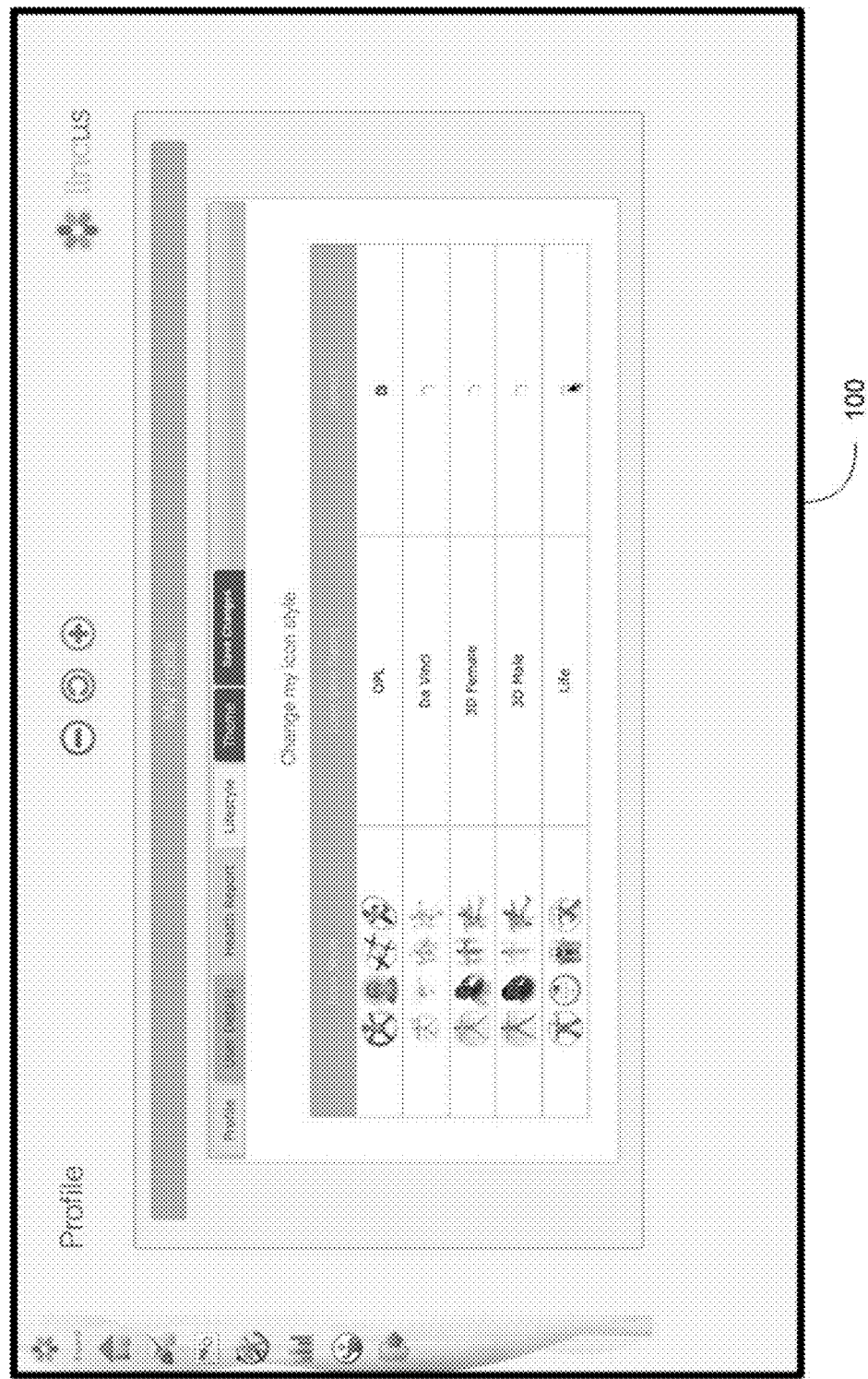
FIG. 1 illustrates a screenshot of a profile control panel, wherein one of a plurality of skins can be selected by an individual user.

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Furthermore, an embodiment of the invention may incorporate only one or a plurality of the aspects of the invention disclosed herein; only one or a plurality of the features disclosed herein; or combination thereof. As such, many embodiments are implicitly disclosed herein and fall within the scope of what is regarded as the invention.

Accordingly, while the invention is described herein in detail in relation to one or more embodiments, it is to be understood that this disclosure is illustrative and exemplary of the invention, and is made merely for the purposes of providing a full and enabling disclosure of the invention. The detailed disclosure herein of one or more embodiments is not intended, nor is to be construed, to limit the scope of patent protection afforded the invention in any claim of a patent issuing here from, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein-as understood by the Ordinary Artisan based on the contextual use of such term-differs in any way from any particular dictionary definition of such term, it is intended that the meaning of the term as understood by the Ordinary Artisan should prevail.

Regarding applicability of 35 U.S.C. 112(f) in the United States, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." When used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Furthermore, as used herein, "self-evaluation" is intended to refer to evaluation completed by a specific individual or another individual or advocate on the specific individual's behalf.

Referring now to the drawings, one or more preferred embodiments of the invention are next described. The following description of one or more preferred embodiments is merely exemplary in nature and is in no way intended to limit the invention, its implementations, or uses.

Profile Creation

In accordance with one or more preferred implementations, profiles are used as a base for stratification of evaluation prescription and recommendation for individuals. There are fixed, slow change and fast change components of the profile. Fixed components include factors such as gender, age (changes but cannot be modified), history of previous disease, personality, learning disabilities, and a long-term unresolvable disease which includes fixed accessibility issues such as learning disability, permanent visual impairment, and permanent hearing impairment. Slow change components include factors such as academic achievement or education level, academic, career or life specialisms, preferences, associated organizations such as a university, care home where the individual may be either a staff member or a recipient of a service, curable diseases, social situation, curable medical conditions, or the severity of a particular unresolvable disease such as diabetes (type 1 and type 2), hypertension, kidney disease, cardiovascular disease, respiratory disease, gastrointestinal disease, neurological disease, musculoskeletal disease, skin disease, and urological disease; and accessibility issues such as changing learning disability (recovery from head trauma or stroke), improving or worsening vision and/or hearing, and place of residence. Fast change components include factors such as rapidly changing preferences, symptoms—including those that are recorded as pictorial representations, recordings from on body or environmental sensors, or perception of social inclusivity.

A profile is created for an individual using data from traditional check box and questionnaire tools, self-evaluation, observed evaluation through a framework integrated into the system, system use, wearables, health/wellbeing devices, home and external environmental sensors, personality tests, platform use as measured by interaction with and choices made within the platform and other systems that may interact with the platform, emotional response to platform use measured by video camera or other sensors, physiological response to platform use measured by video camera or other sensors, and conventional social and health records.

Furthermore, profile information can be pre-populated for an individual with the same or similar characteristics to another individual or group of individuals that have previously responded in such a way to the platform through use, decision-making, choices, and ratings.

Furthermore, based on profiles a recommended content engine can be developed and utilized, as discussed in detail below with reference to FIGS. 100-105.

User Interface

In accordance with one or more preferred implementations, a user interface can be changed depending on user preferences, either automatically based on the user profile or manually through the platform. The user interface can be changed to suit the user preferences, therefore enhancing the user experience.

Figure 2:
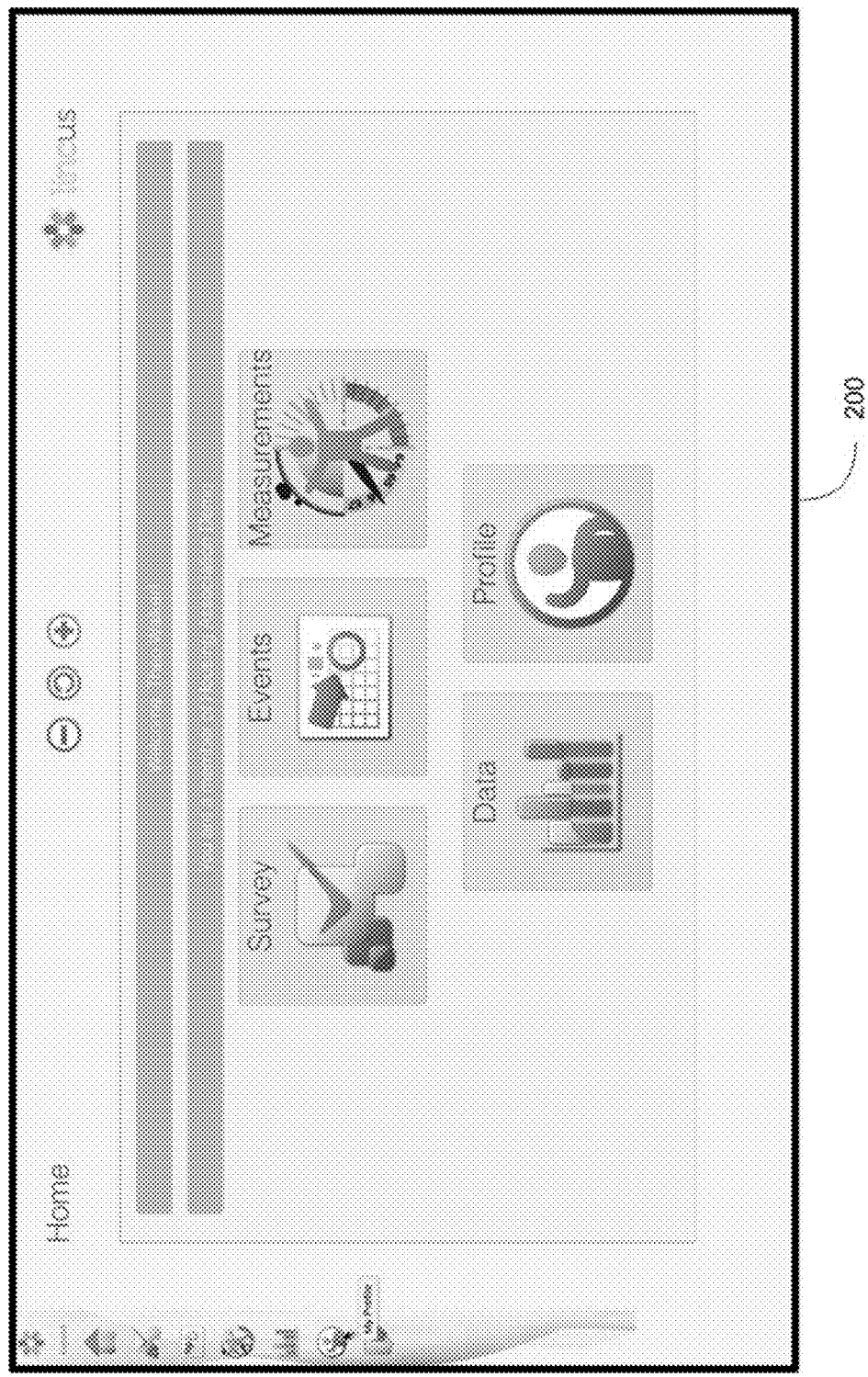
Figure 3:
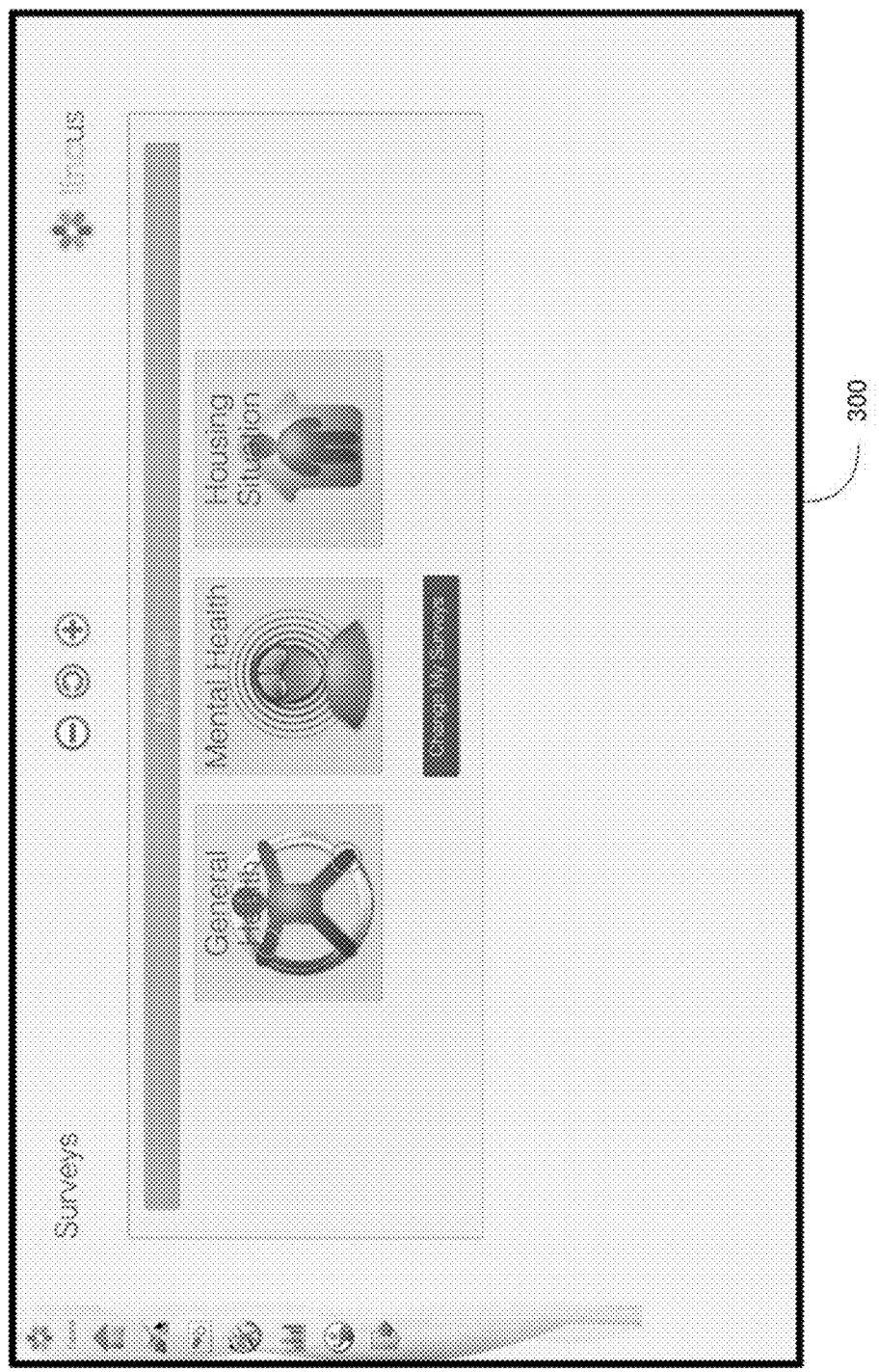
Figure 4:
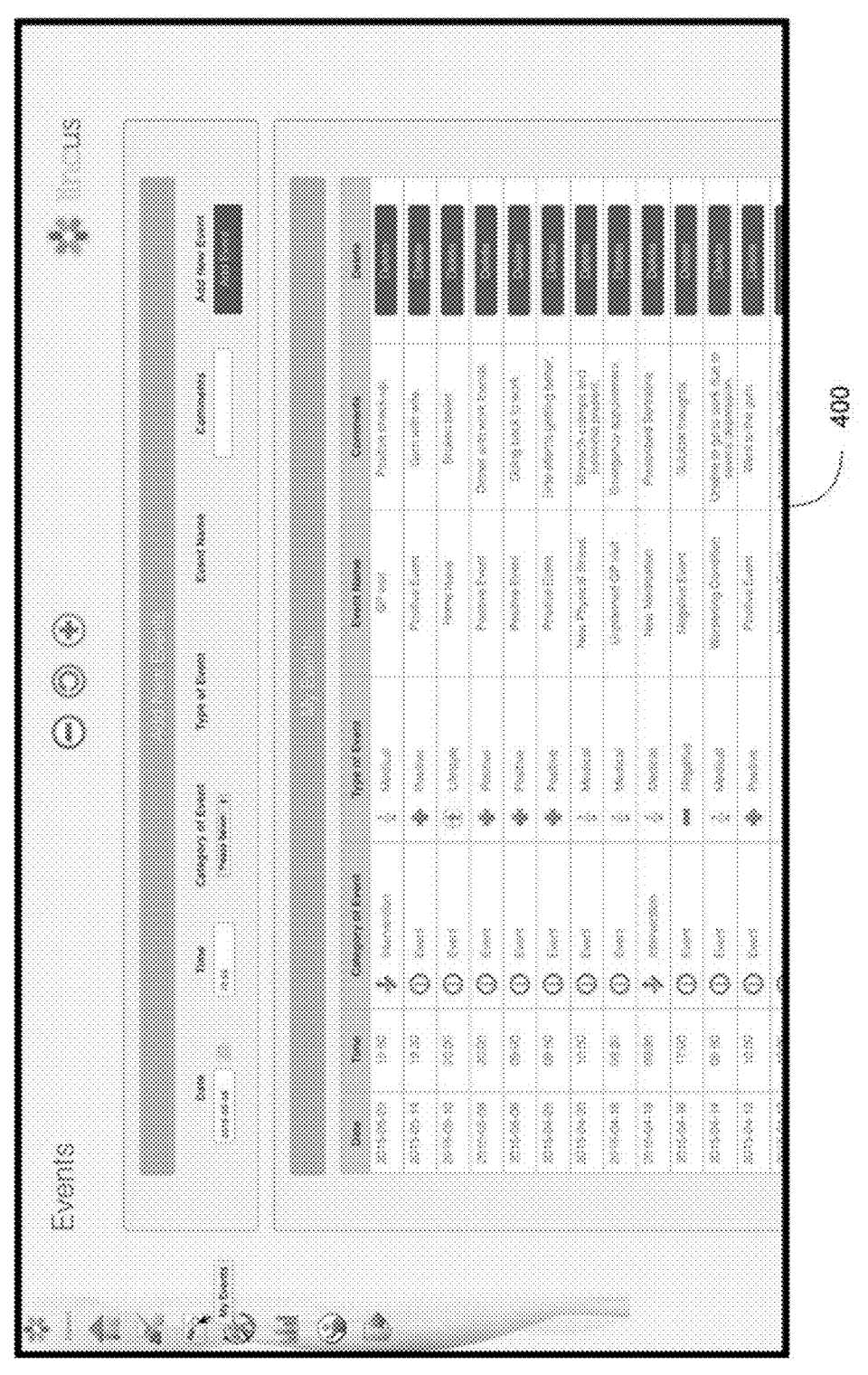
Figure 5:
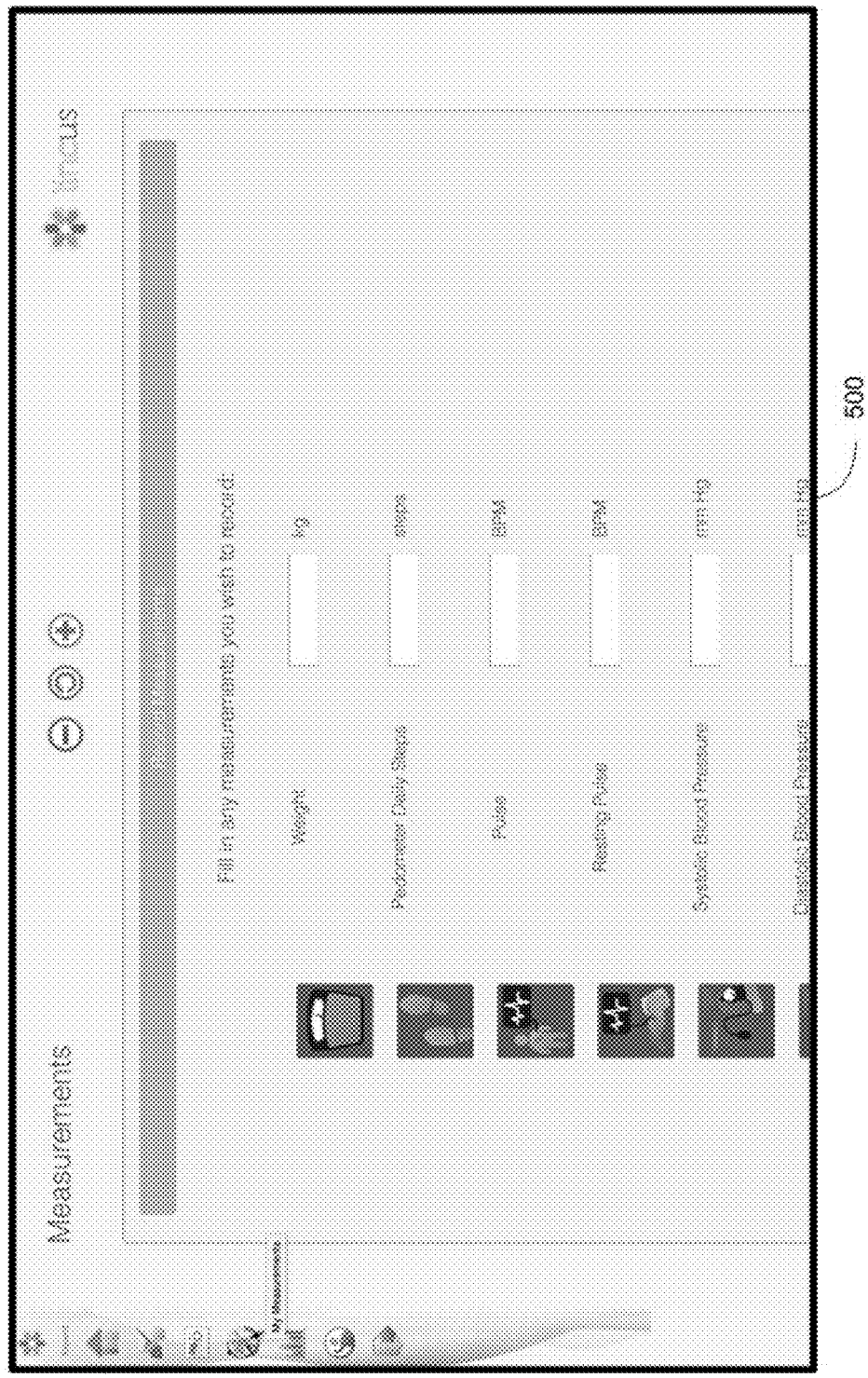
Figure 6:
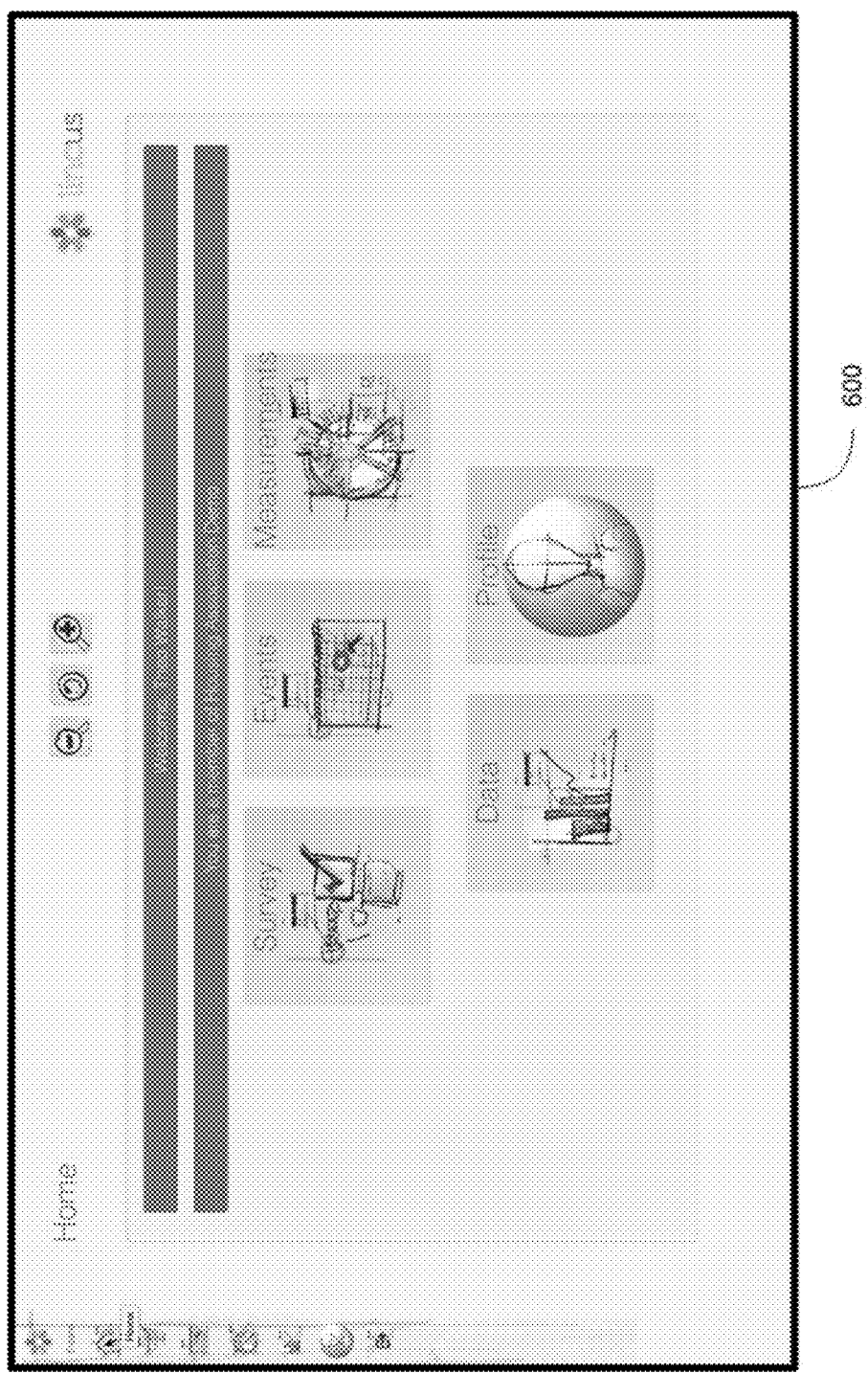
Figure 7:
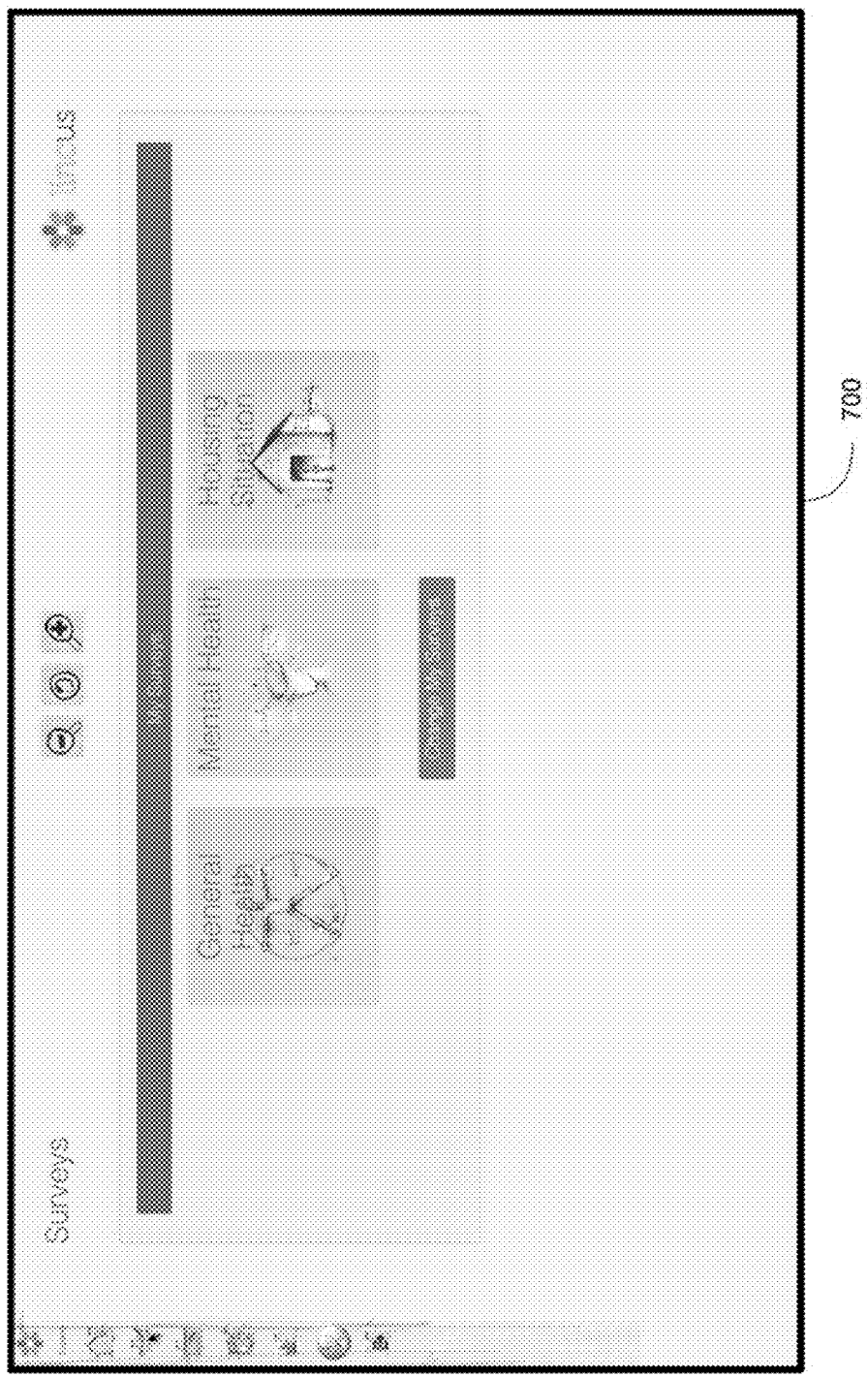
Figure 8:
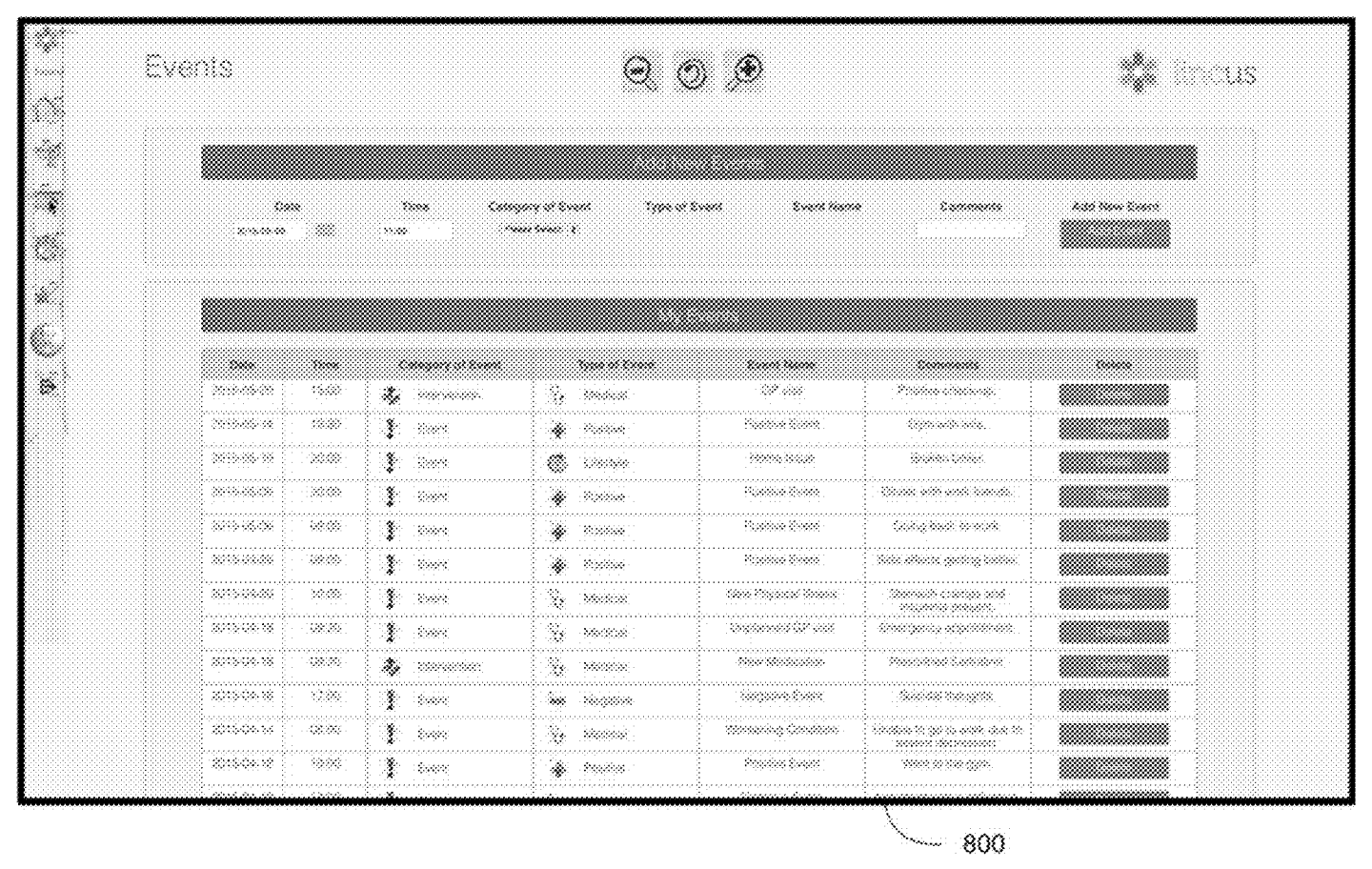
Figure 9:
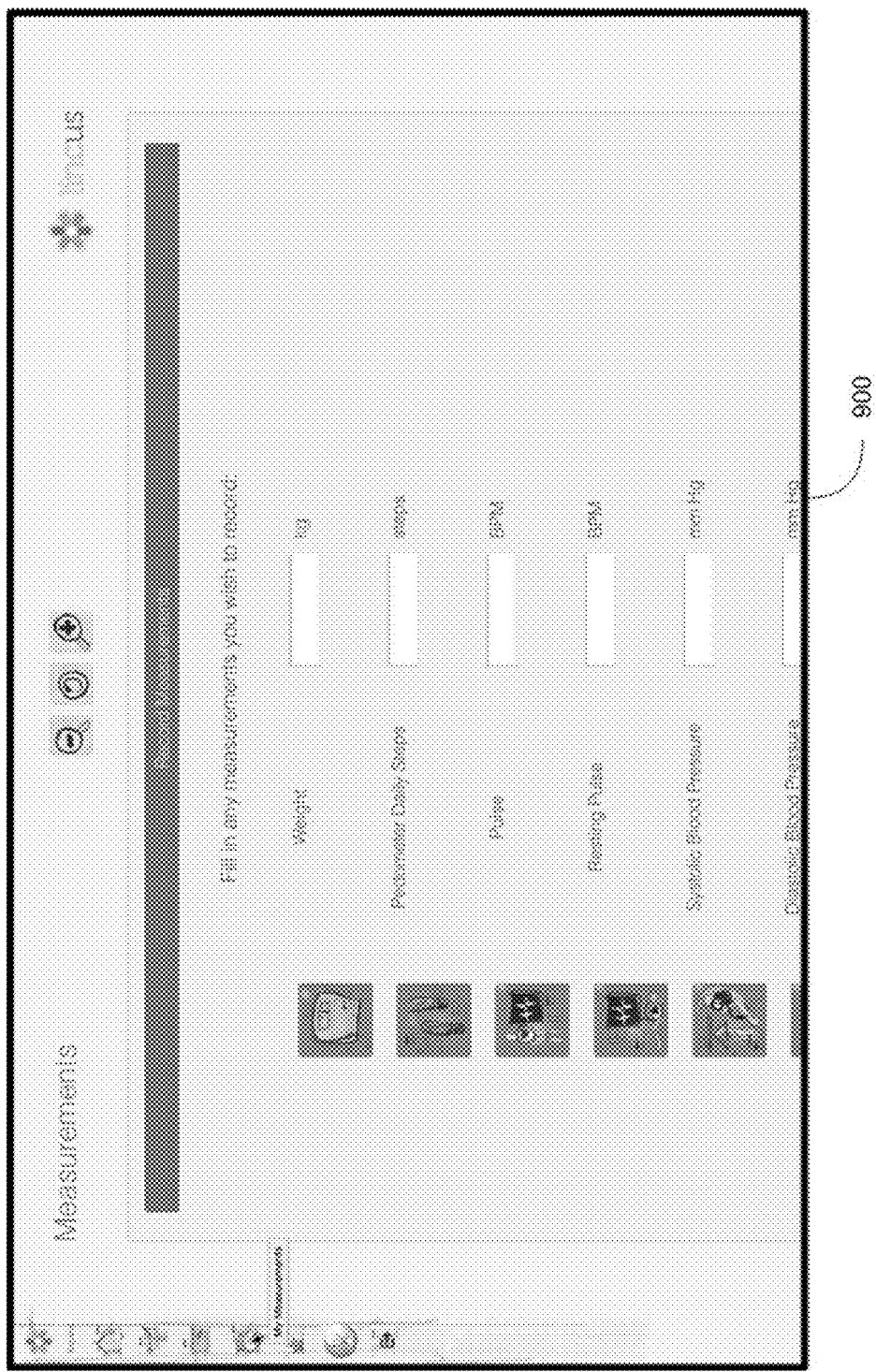
Figure 10:
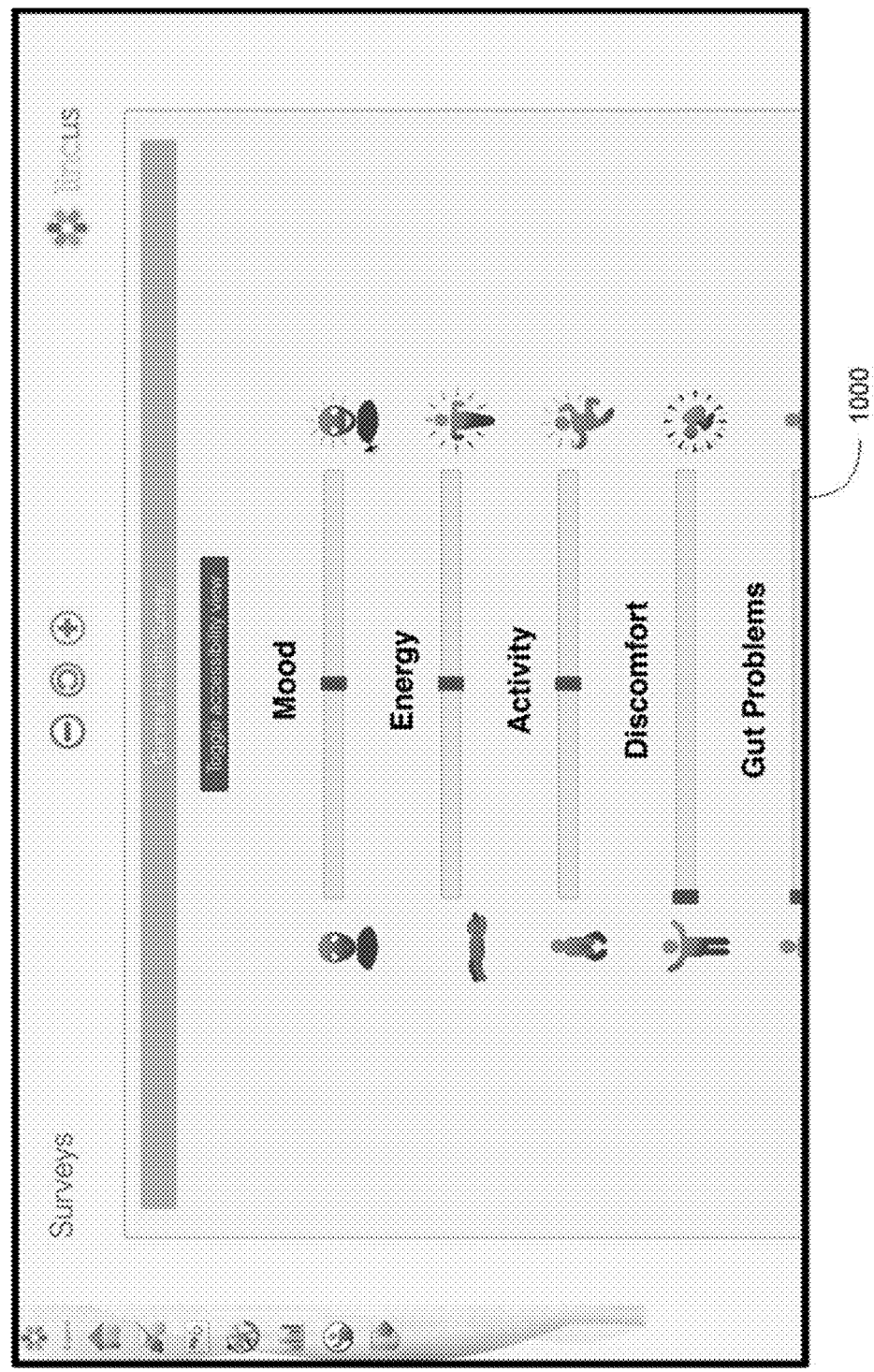
FIG. 10-14 illustrate additional skins for a "General Health Survey" page.
Figure 11:
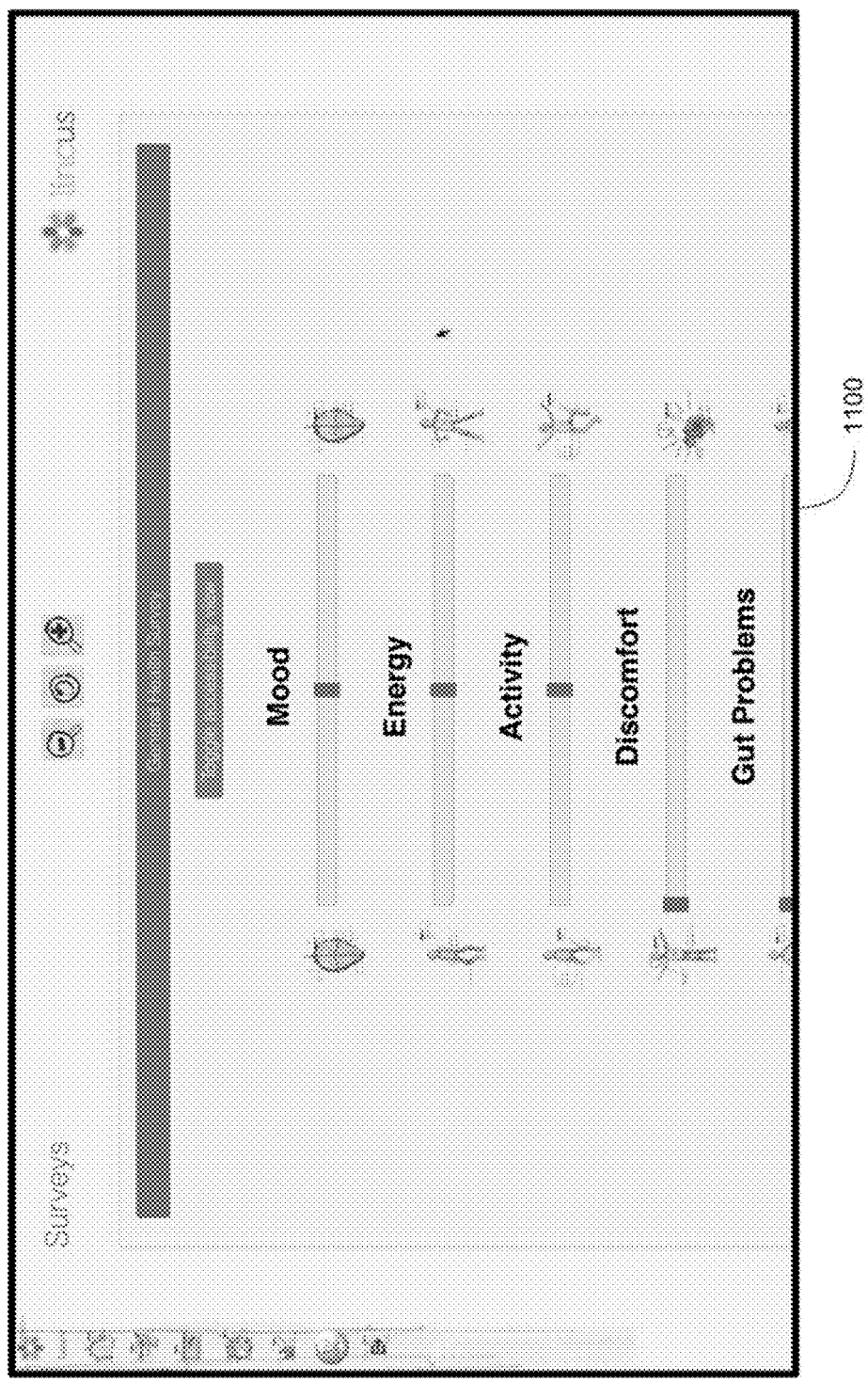
Figure 12:
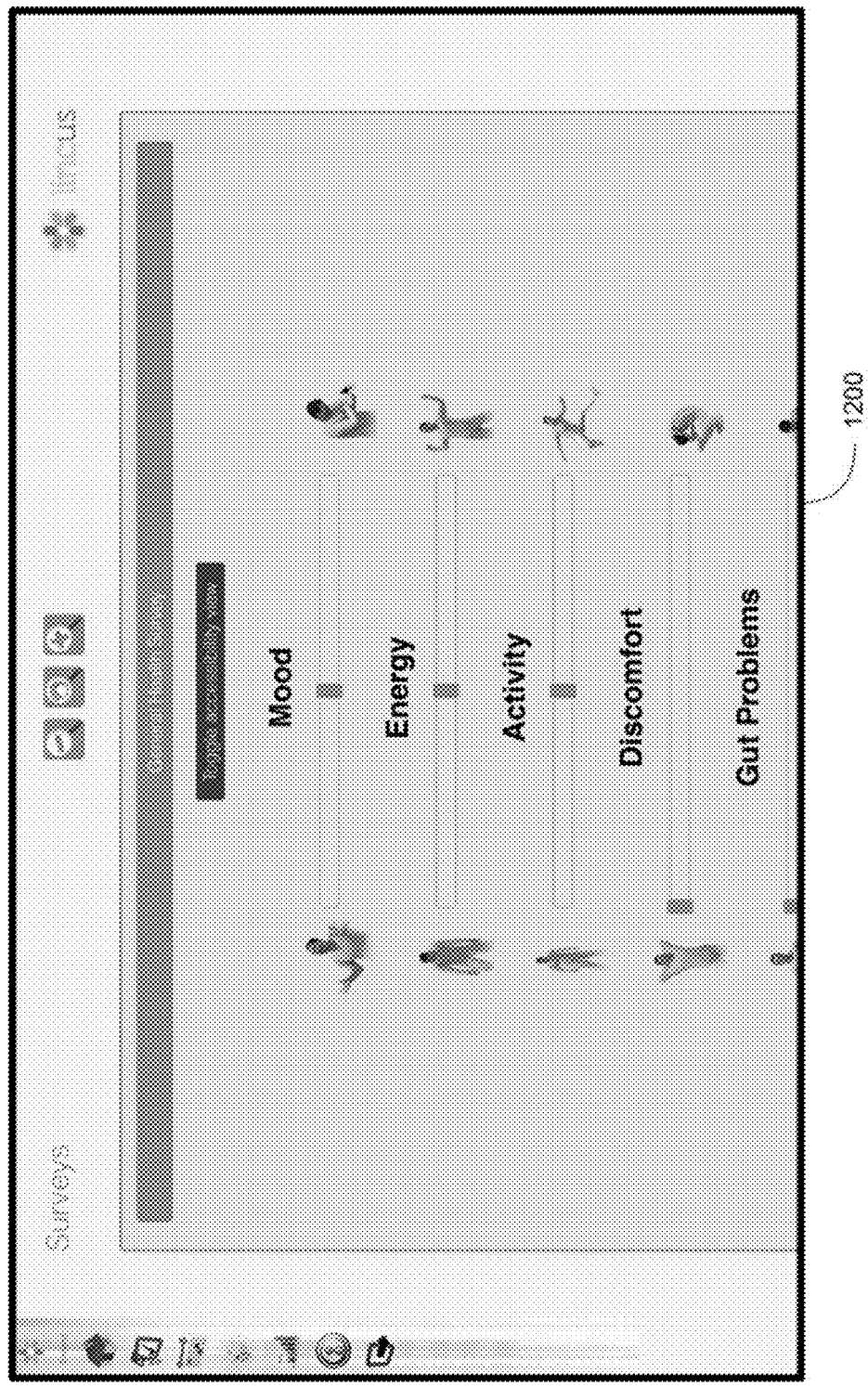
Figure 13:
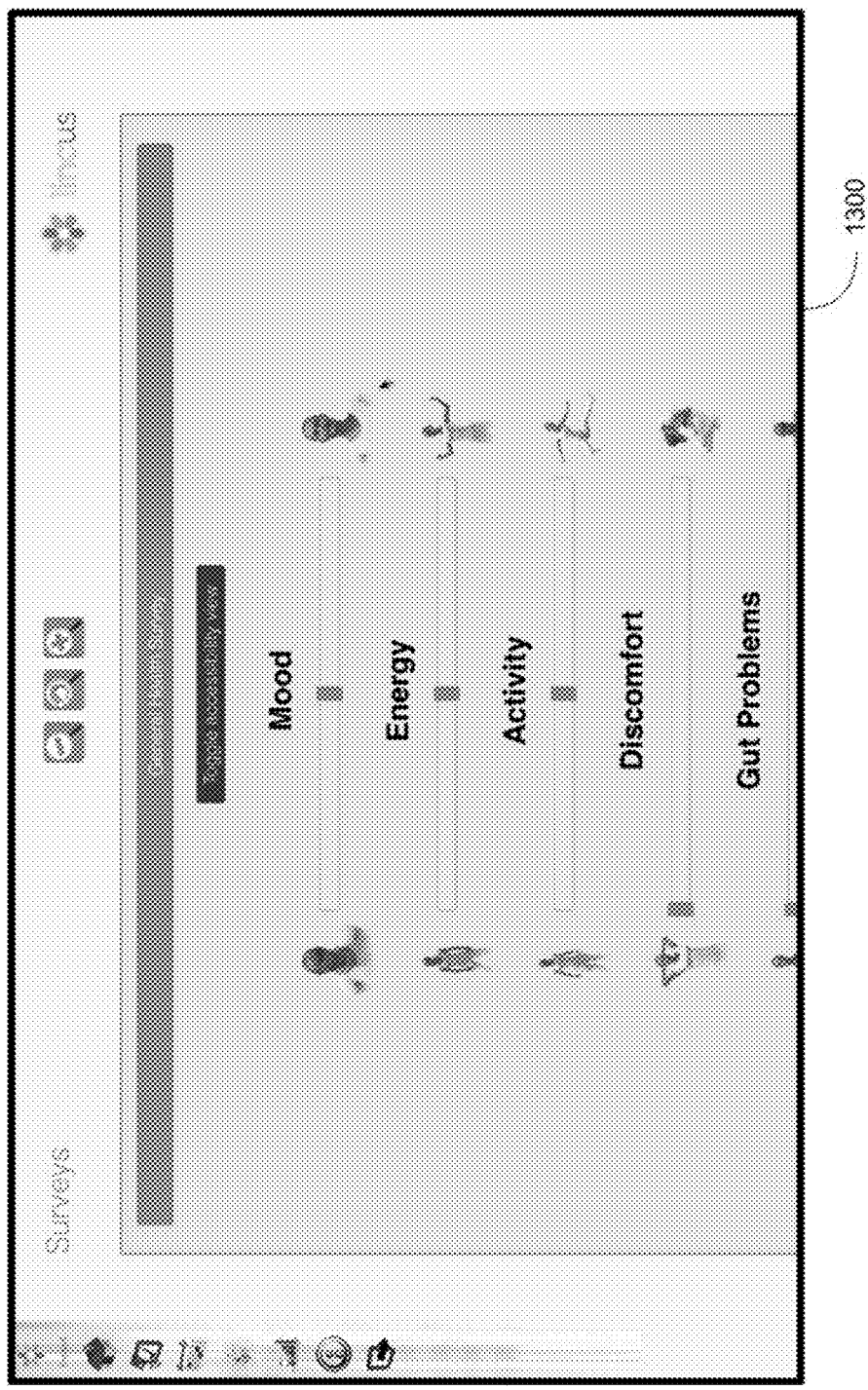
Figure 14:
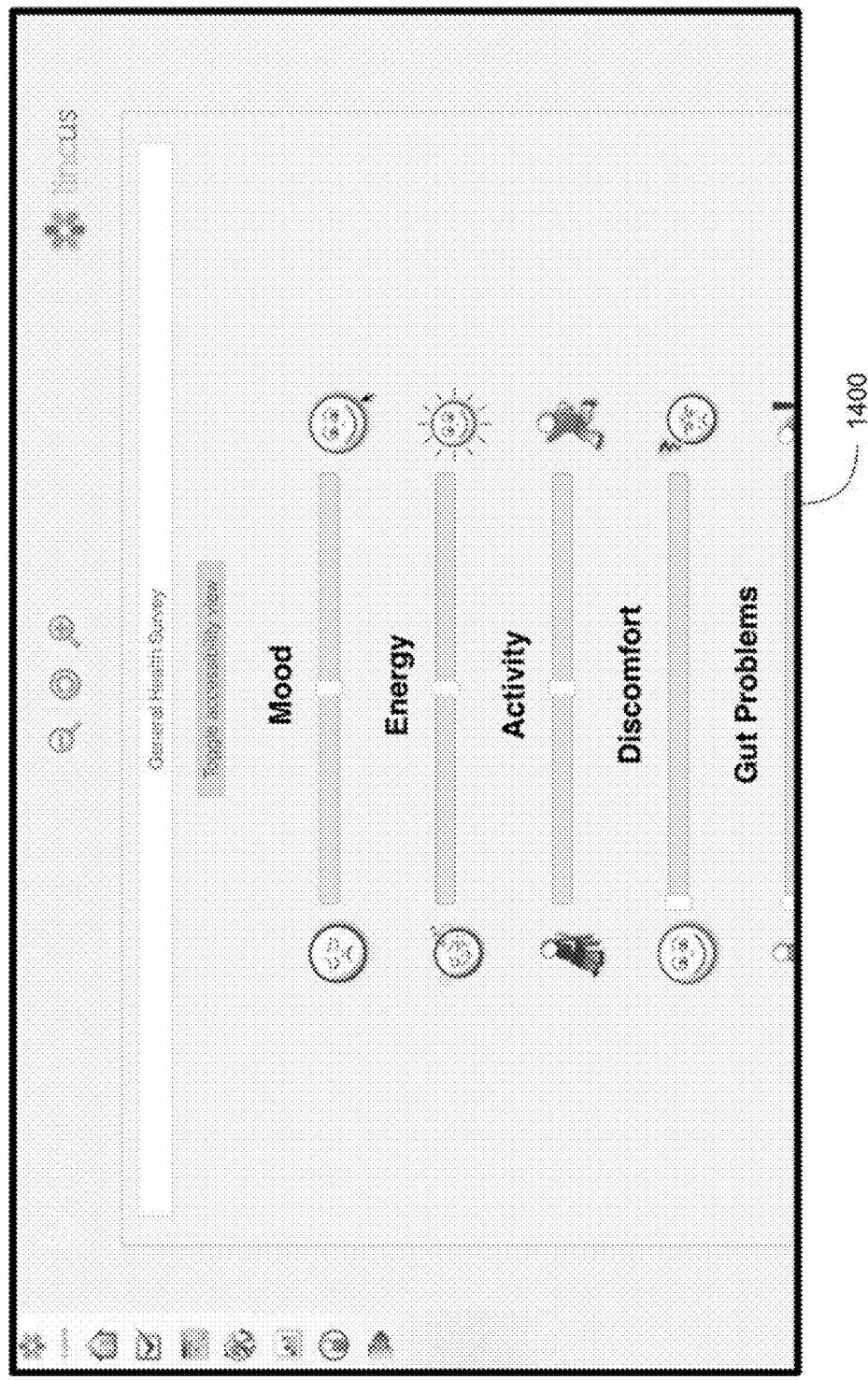

In the simplest implementations, changes in a user interface to suit personality and preferences may include changes in text type, color, size or color hues and layout of the platform. In a more complex implementation, a profile is set up with difference styled icon sets and colors, as illustrated in FIG. 1, which shows a screenshot 100 of a profile control panel. Using the profile control panel, an individual can select different user interface styles or skins for use with a web interface. Thus, for example, an individual can select an "OPL" skin, resulting in a "Home" page as seen in the screenshot 200 of FIG. 2; in a "Surveys" page as seen in the screenshot 300 of FIG. 3; in an "Events" page as seen in the screenshot 400 of FIG. 4; and in a "Measurements" page as seen in the screenshot 500 of FIG. 5. Alternatively, an individual can select a "Da Vinci" skin, resulting in a "Home" page as seen in the screenshot 600 of FIG. 6; in a "Surveys" page as seen in the screenshot 700 of FIG. 7; in an "Events" page as seen in the screenshot 800 of FIG. 8; and in a "Measurements" page as seen in the screenshot 900 of FIG. 9. Upon selection of a different skin, the code calls up the appropriate graphics database to populate the style sheet framework. The user interface will then change from the prior style to the new style. It will be appreciated that the functionality provided through each page preferably remains the same.

Addition different skins for a "General Health Survey" page are illustrated in the screenshots 1000, 1100, 1200, 1300, 1400 respectively found in FIGS. 10, 11, 12, 13, and 14.

Evaluation Prescription

Evaluation prescription and setting thresholds which is the methodology by which an individual, or group of individuals, are prescribed evaluation. Evaluation prescription can be: automated (based on the static, slow changing and fast changing features of a profile), expert prescribed (where an expert can be an individual or a group of individuals), or self-prescribed. In any of these cases, it is important that the profile is taken into account. The evaluation prescription can be made up as any combination or permutation of automated or computer driven, expert and individual prescription. The evaluation that is prescribed can be in the form of self-evaluation, wearable sensor, health or wellbeing device, environmental sensor, or traditional medical or social evaluation tools including history, physical examination, and investigation ranging from blood tests, to biopsies and to imaging carried out by devices such as MRIs or CT scanners.

To enhance self-evaluation compliance from an individual, it is helpful if evaluation is guided or prescribed by: a trusted individual, such as a specialist; or themselves; or a trusted source, such as a computer program. Before evaluation is prescribed, it is important to have a profile as to effectively prescribe self-evaluation there is background information or a profile needed so the prescription can be stratified to suit that individual's needs. A profile can be compiled as outlined above.

Automated Evaluation

Contemporary records tend to change slowly over time, however recent developments in health reporting apparatus, systems, and methods, such as those disclosed in the incorporated patent, allow for very rapid updates so there may be a rapidly evolving component of the profile that is influenced by self-reporting that, by its nature, may change the prescription of self-reporting. An example of this is the case in which someone starts to report an increasing cough—a rapidly changing variable—and we know they have a history of pneumonia—a static or slowly changing variable. Taken and considered in combination, the system by preset programmed rules will recognize that there has arisen a need to also record fatigue, nausea, sputum, sputum quality, shortness of breath, and fever. This would then be prescribed by the system so that more intensive and focused monitoring can occur for the individual so as to identify whether they need treatment, and the level of treatment. Through utilizing machine learning techniques that will learn from expert evaluation prescription, the system can self-refine and evolve over time.

Expert or Self-Evaluation Prescription

Figure 15:
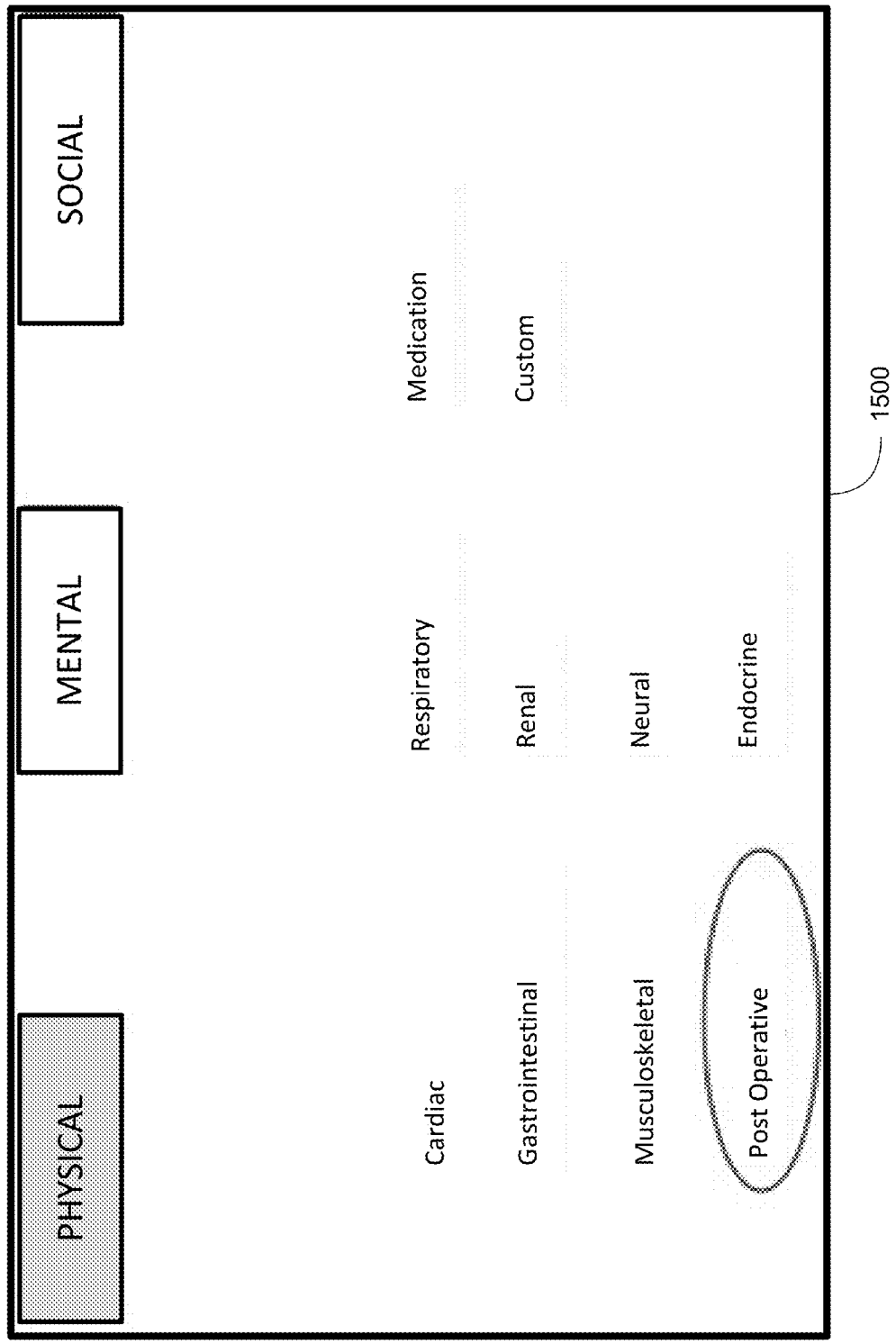
FIG. 15 schematically illustrates a dashboard for expert or self-evaluation prescription.

A dashboard 1500 for expert or self-evaluation prescription is schematically illustrated in FIG. 15. First, an individual user accesses the evaluation prescription dashboard and selects an evaluation of physical, mental, or social health. The illustrated dashboard represents the individual selecting physical health and "Post Operative" evaluation from a prepopulated list. Alternative, the individual user completes a custom form for evaluation. The categories can be represented by words, as represented in FIG. 15, by pictorial representations, or a combination of words and pictorial representations.

Figure 16:
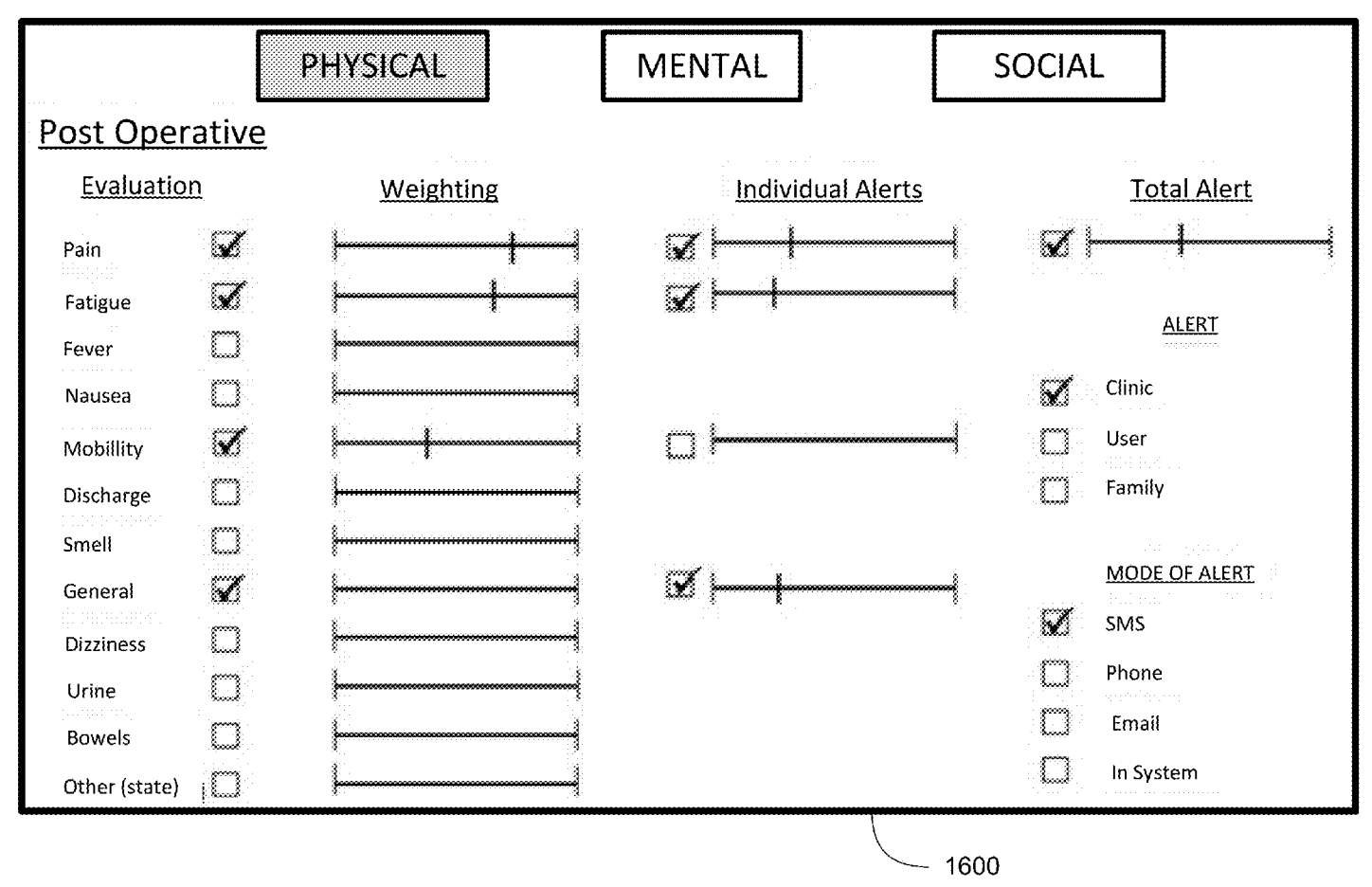

Once clicking on the selection a further screen appears where the explicit evaluation can be prescribed, for example as illustrated in FIG. 16. The user can either select a "best practice" default setting based on the profile of the individual, or a pre-saved setting from themselves or a trusted source, such as a national body, or they can self-select surveys as in the example below. The surveys are weighted evenly for impact unless the user wishes to change them. As we get more data we will decide on the weightings and use machine learning to decide (tuning) most appropriate weightings based on prior records which includes expert input. The weighting is for calculating the combined score which is for visualizing the data and decision-making including alerts. In the example below pain and fatigue have been weighted highly and mobility has been downgraded. General wellbeing has been left at neutral. The user may also set thresholds. Alert thresholds may also be set for individual surveys: this means if those metrics drop below a certain level then an alert is sent. An alert can also be set for the total combined score from the surveys. Who is alerted can be chosen from a variety of targets. In this case clinic, user and family are potentials but this is not limited and custom targets can be included. Also mode of alert can be selected, for example via SMS message.

Next a frequency and length of evaluation can be prescribed, along with the mode of reminding that an evaluation is required. Such selections are made, for example, through interfaces 1600 and 1700 as schematically represented in FIGS. 16 and 17 respectively.

Once the options are selected, the final survey text appears and pictorial representations of the surveys can be chosen from a pictorial library to further enhance accessibility, understanding and compliance.

Figure 18:
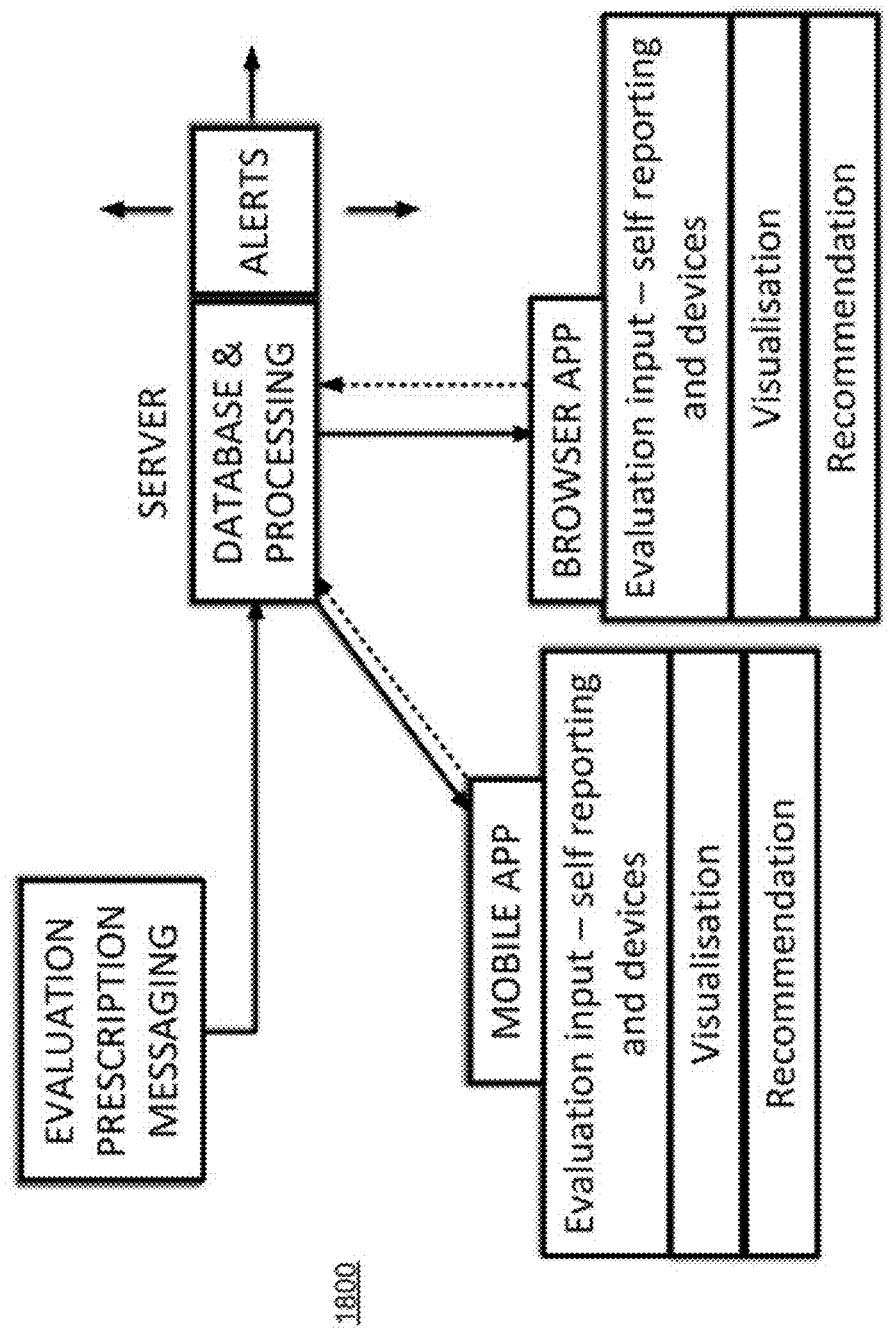
FIG. 18 illustrates an arrangement and communication flow in accordance with one or more preferred implementations.
Figure 19:
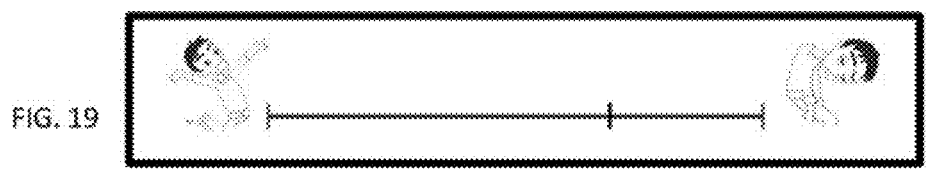
FIGS. 19-24 illustrate interface elements designed to facilitate user input regarding fatigue, anxiety, and a social life.
Figure 20:
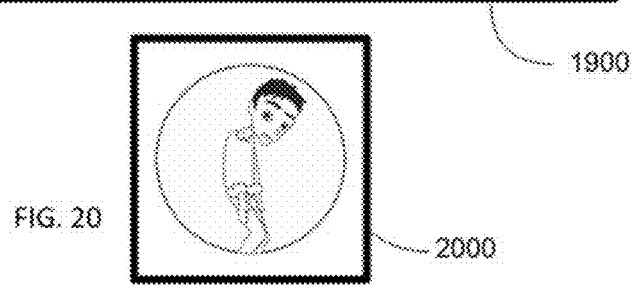
Figure 21:
Figure 22:
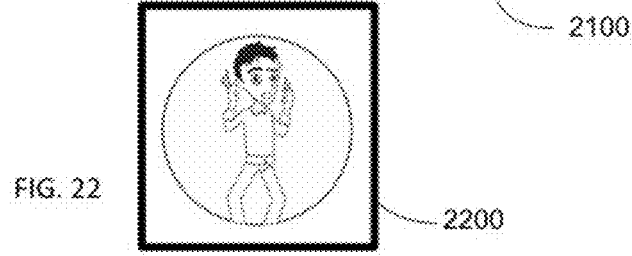
Figure 23:
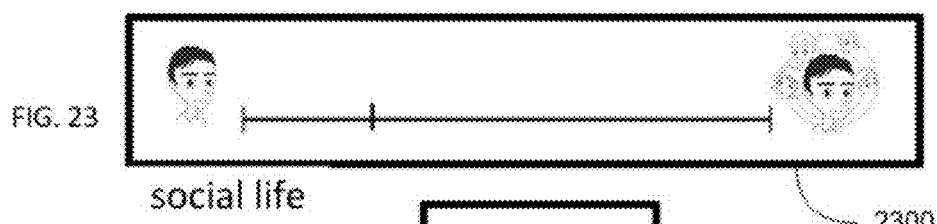
Figure 24:
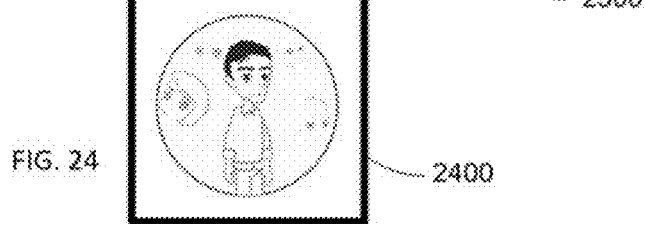

The evaluation inputs are then sent to a server where they are processed and the appropriate evaluation surveys are associated with the individual's profile. They will appear on their browser application where the data is accessed from the server, and also may be ported to a mobile application if the user has this. This arrangement 1800 and communication flow therein is represented by the components and paths schematically shown in FIG. 18. Furthermore, the alerts of FIG. 18 preferably are sent to the browser and the mobile device as well.

Over time, the evaluation in a particular use case can be accessed by all, or a select group or individual based on their evaluation prescription preferences. At the backend, the expert who prescribed the evaluation is ranked in-house. For instance, the Royal College of Surgeons or the American Heart Association will have a higher ranking with regards to weighting for system refinement than a small local charity secondary to the size, length of time in operation and international recognition of excellence of the former two organizations. Preferably, after the system has been running for a period of time, the weighting is refined based on success within the system. Target users and experts preferably report back on how accurate the alerts are and especially if one is missed. The system or an associated entity preferably provides organizations with feedback on how well their methods work compared with others.

Data Processing

Data processing includes both validation of data through cross-referencing of different evaluation sources, sentiment analysis, and alerts. Such data sources may include, for example, any of the data sources used to populate fields of the profile identified above, including traditional check box and questionnaire tools, self-evaluation, observed evaluation through a framework integrated into the system, system use, wearables, health/wellbeing devices, home and external environmental sensors, personality tests, emotional response to platform use measured by video camera or other sensors, physiological response to platform use measured by video camera or other sensors, and conventional social and health records.

Data validation in this system involves comparing related yet independently collected data. The data may be independent through time, place, individual, or method of collection. For example, if the data for a particular metric such as perceived activity level and activity level recorded by a tracker and mobility recorded by a career has similar scores then the data can be more trusted, especially when used for decision-making purposes. Conversely when there is a discrepancy such as an examination by a physician indicates severe cardiac failure and the individual reports high energy levels and activity then the data needs to be interrogated. In this case the objective examination would probably take on a higher ranking than the energy levels and activity scores though would ideally be related to other non-human such as results from investigations. In general, the data would be trusted more if all observers (clinicians+patients+care workers+family members+sensors+investigations+system usage data) were in agreement. The data for cross validation can come from multiple sources as outlined above in profile creation. Any data that is interconnected or related can be used to cross validate the entirety of the data.

This process has more purpose than simply validating the data, it can also be used for audit and investigation. Discrepancies in the data can identify certain behaviors that may be positive or negative. For example, if three advocate users who were careers were looking after an individual and one of them always scored a lot higher than the others this could be for several reasons such as: they were looking after them really well so the scores were higher; they were rigging the score to make themselves look better than they were; or they were working with the individual at a particular time of day when they always felt better. The data will not necessarily discover the cause but it will indicate there is an issue that warrants investigating, even if it is a better way of doing things.

Discrepancies in the data can also be found in certain user groups, especially once enough data is collected. For example, someone who is falsifying their data for a positive outcome such as for fiscal reward from insurance is likely to have a different data pattern over time than a typical user.

Data discrepancies can also be used to assist in communication. For example, if three different system users involved in the care of someone (e.g. a family member, a social worker and a clinician) are completing an assessment on an individual using a framework tool such as the health equalities framework and there are different outputs from the evaluation overall then the system would highlight the discrepancy and bring it to attention for discussion as the discrepancy may negatively impact on the individual's care.

Over time using machine learning principles the system will identify which data streams and types are tightly correlated and what the relationship might be. The more data collected the more robust and certain the system will be that certain patterns exist or are expected. When an unexpected pattern occurs this will be flagged up to look into the causation by such a pattern. Once discovered this will be inputted into the system, effectively tuning the system validation further.

Before the thresholds are explained another feature of the system that needs to be outlined is that of sentiment analysis. Certain scores, such as overall wellbeing, mood or social life, have positive sentiment, whereas others, such as coughing, nausea, frustration, job dissatisfaction or loneliness, have negative sentiment. Other scores follow a shape. The simplest of these to use for illustration purposes is that of temperature where too hot or too cold are negative whereas somewhere in the middle is positive. Other examples include appetite, stress (where no stress can be taken as boredom or no challenge), social interaction (where too much can be negative, just as none can be taken as negative). With sentiment assignment it is important to clarify that the sentiment shape for one person may be different for someone else and this can depend on multiple aspects in their profile that range from physical or mental diagnoses, to social circumstances to personality. For instance, an individual who is manic depressive and tends to obesity would have their most positive sentiment where appetite is low but not too low whereas for most people it would be somewhere in the middle. As such a sentiment and sentiment shape needs to be defined for everyone and then can either be manually assigned by an expert or learned over time by the system.

Alerts can be simply triggered by predefined thresholds as described above in, evaluation prescription, or they can be triggered by trending of single or combined streams, or by the data following a known or learned pattern. Predefined threshold alerts are straight forward in that a user will define at what point, or points, an alert or alerts are triggered and who will be alerted and by what means. Alerts can take on varying levels of intensity and can be messaged and represented in different ways. For example: a score of 5 might trigger a yellow alert that will notify a close family member by email and system alert; a score of 4 may trigger an amber alert that will notify a close family member by email, SMS, and system alert, and also a neighbor by SMS, and system alert. A score of 3 may trigger a red alert that will ring both the neighbor and two family members and email a social worker and the medical clinic; whereas a score of 2 or less will trigger a black alert that will ring, email, SMS, and system alert everyone on the list potentially including emergency services. For all of the alert systems a closed loop is created where the target for the alert needs to acknowledge both that the message has been received, and if appropriate what is being done about it, the intervention. The intervention is then added into the system and used for further analysis to look at the efficacy of that intervention. Any time an alert is triggered this is taken as an event and the system will analyze the patterns leading up to certain events on both an individual and a population basis.

Trending alerts will trigger the same system described above though will do so on the basis of the amount of fall in score or combined scores over a unit of time. For instance, a fall of 20% over 2 weeks may not trigger an alert yet a fall of 10% in one day may trigger a yellow alert and 20% in 2 days may trigger an amber alert, with 15% in 2 days triggering a yellow alert and 15% or 20% in a day triggering amber and red alerts, respectively.

More complex than the above alerts are patterned alerts. These occur when a combination of metrics trend or threshold in a certain way. Patterned alerts are one of the reasons for selecting weighting on the initial evaluation prescription. Weighting is relevant in this setting as illustrated by the example of an individual who has a history of heart failure. In this individual, cough, shortness of breath, and fatigue would carry more relative weighting than in someone with diabetes and no history of heart failure. A social example where more than one user can be involved would be in the situation where an individual who had a history of domestic violence and, high job dissatisfaction scores, and was hungover (together a risk for a violent event) was at the time co-located with their partner who was angry and tired (which would amplify the situation even more and make a violent event more likely). Another combined user medical example would be in the situation where someone has symptoms of a flu-like illness and were meeting with a family member who has a history of severe respiratory illness that sometimes required hospitalization. In all of the above examples if an alert is triggered, received and acknowledged an action can be taken to decrease the likelihood of a negative outcome occurring. These are examples that can be programmed into the system however other examples might not be so clear and the above examples might require different weighting or sentiment or thresholds for an individual's situation or a group situation. In this case, the system will learn through retrospective analysis of the correlations amongst data streams leading up to certain events that an event is more of less likely and can therefore encourage a certain behavior or action by a positive alert or vice versa. As more data is inputted into the system, the utility of the feature will be enhanced.

Visualization

Visualization of the data from the system is important for conveying information. In the case of self-evaluation data, it is important to ensure that the data is fed back in such a way that it represents what the individual really meant. Visualization of evaluation data preferably is provided with a focus on self-evaluation.

Three examples of this are illustrated in FIGS. 19-24, in which an individual inputs physical data regarding fatigue, mental data regarding anxiety, and social data regarding current social life. The data is input for fatigue by sliding the marker between the extremes, as shown in the user interface control 1900 of FIG. 19, with the output being displayed to the user in an interface 2000 of FIG. 20. Similarly, the data is input for anxiety by sliding the marker between the extremes, as shown in the user interface control 2100 of FIG. 21, with the output being displayed to the user in an interface 2200 of FIG. 22; and the data is input for social life by sliding the marker between the extremes, as shown in the user interface control 2300 of FIG. 23, with the output being displayed to the user in an interface 2400 of in FIG. 24.

Figure 25:
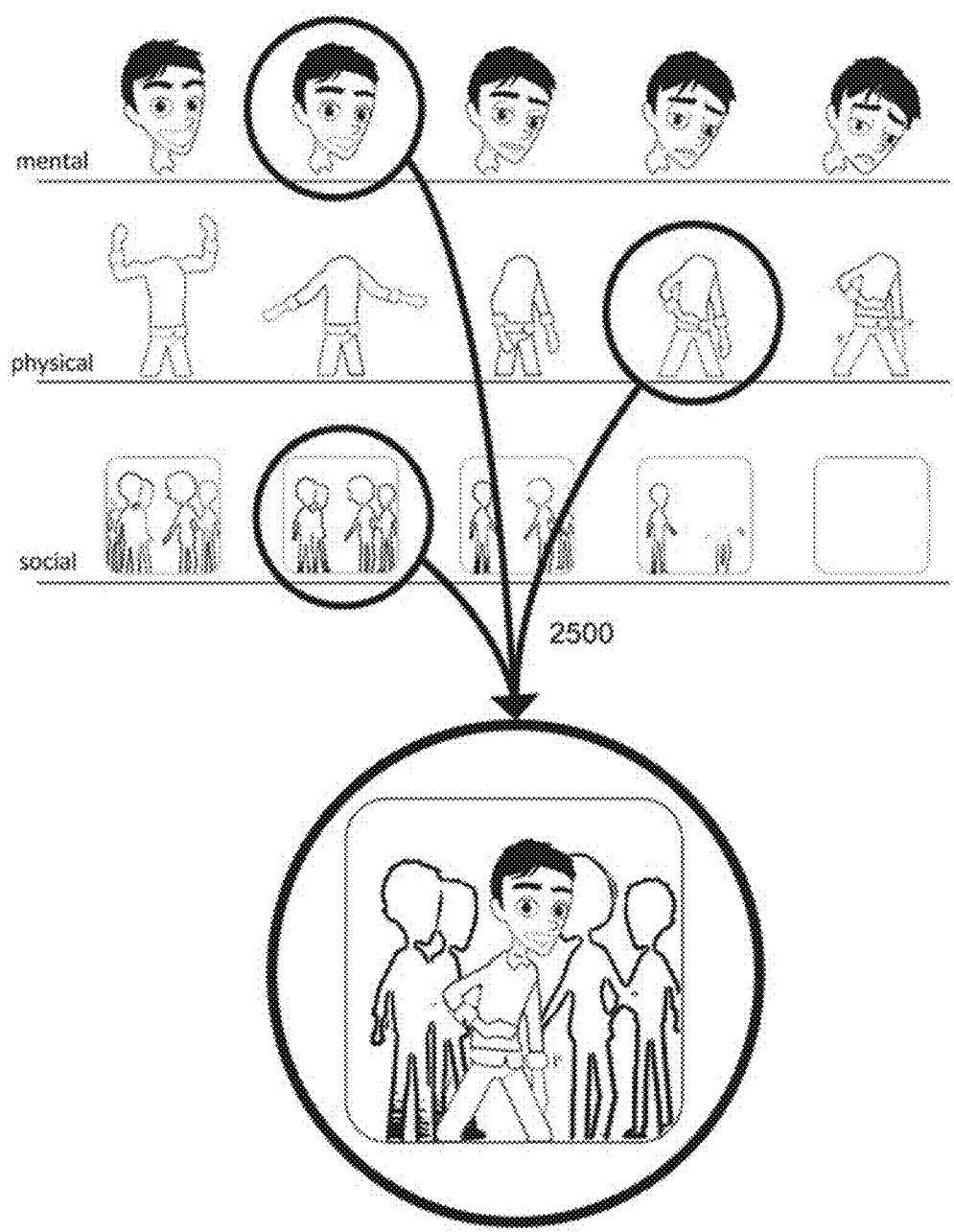
FIG. 25 illustrates a flow for selecting different parts of a composite image to be displayed which combine to depict mental, physical, and social states.

Taking this further, a methodology to quantify the combination of physical, mental and social outputs is provided that utilizes quantified, stepped pictorial representations. This methodology is schematically represented, for example, by the flow 2500 seen in FIG. 25 for selecting different parts of a composite image to be displayed as output to a user via an interface, similar to the output displayed in each of FIGS. 20, 22, and 24. In FIG. 25, variable mental (from the shoulders up); physical (from the neck down); and social (the surrounding environment) images are selected based on different input received from the user, whereby depictions of physical, mental and social health status are combined into one picture in one field of view.

Figure 26:
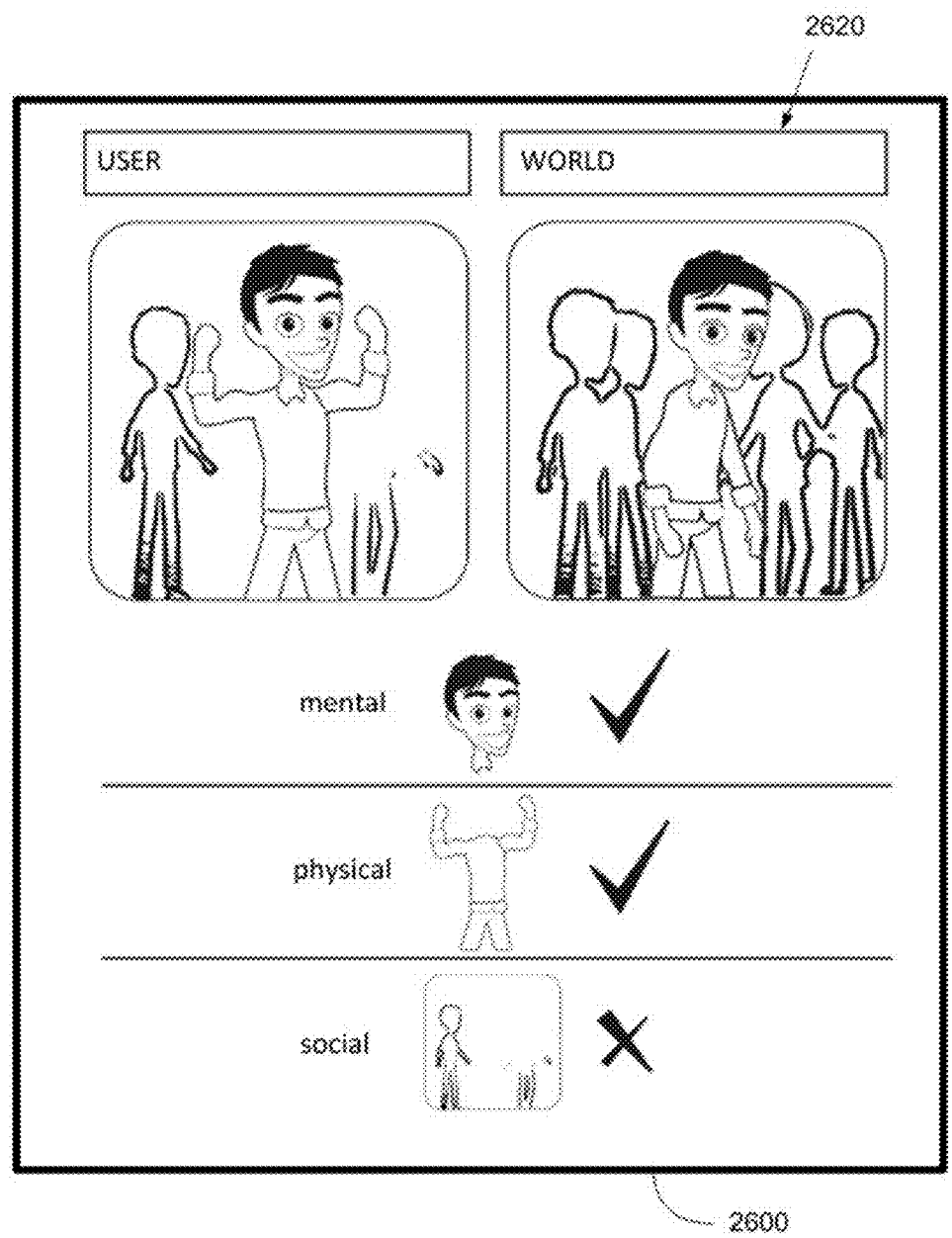
FIG. 26 illustrates an exemplary interface depicting both a user's composite image and a composite output representative of all users in the world.
Figure 27:
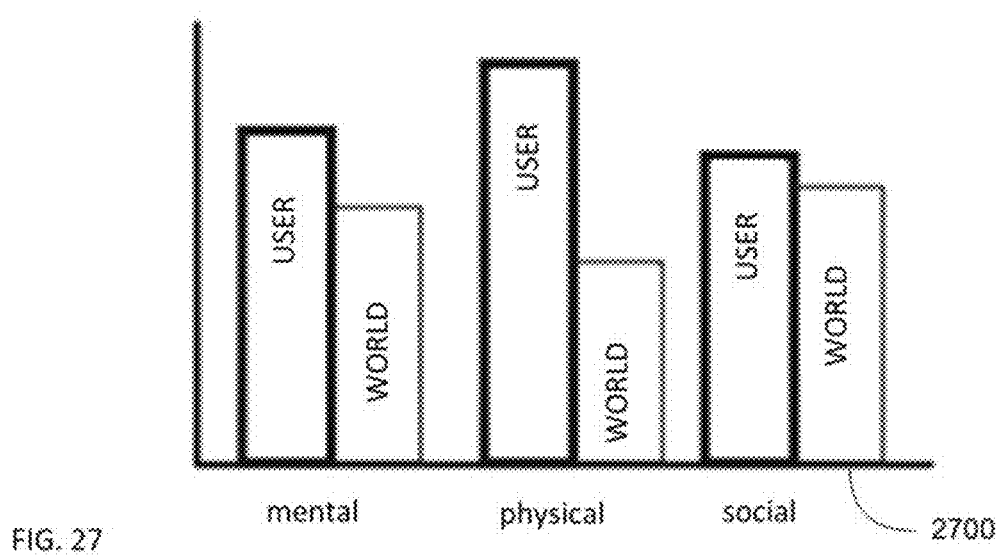
FIG. 27 illustrates an exemplary bar graph displaying bars for both a particular user and all users.
Figure 28:
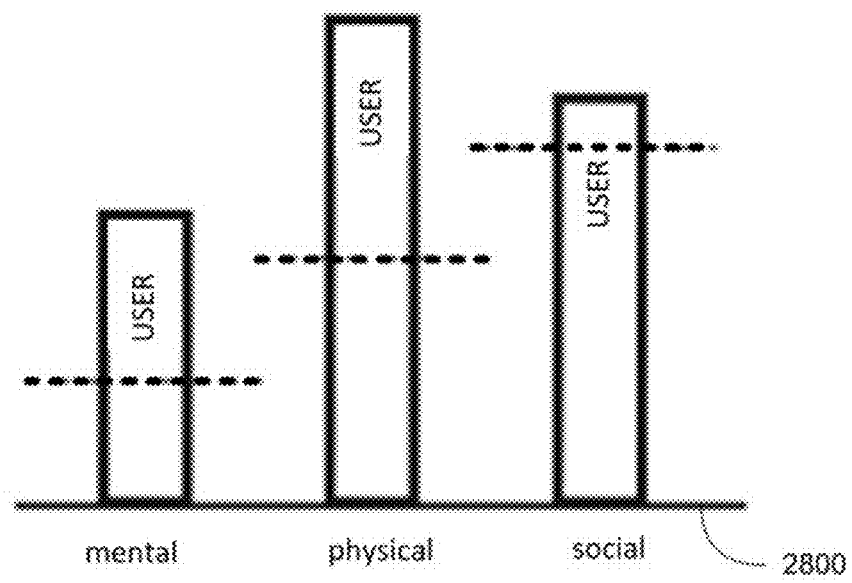
FIG. 28 illustrates an exemplary bar graph displaying a bar for a particular user and a corresponding threshold line for all users.

In similar regard, FIG. 26 illustrates a screenshot 2600 of an interface that may be displayed to a user showing the actual component images that are used in the composite output that is displayed to the user. The interface 2600 further compares the user's composite output to a composite output representative of all users of in the world, seen in FIG. 26 at 2620. FIG. 27 illustrates a bar graph 2700 for both the user and the world for making comparison; and FIG. 28 illustrates a user bar graph 2800 with thresholds representing the world for making comparison. This comparison can change over time. The purpose of this is to both to better communicate the holistic health status, which can come from multiple data sources as described above, and not necessarily self-evaluation only; and also to improve engagement with the platform.

Figure 29:
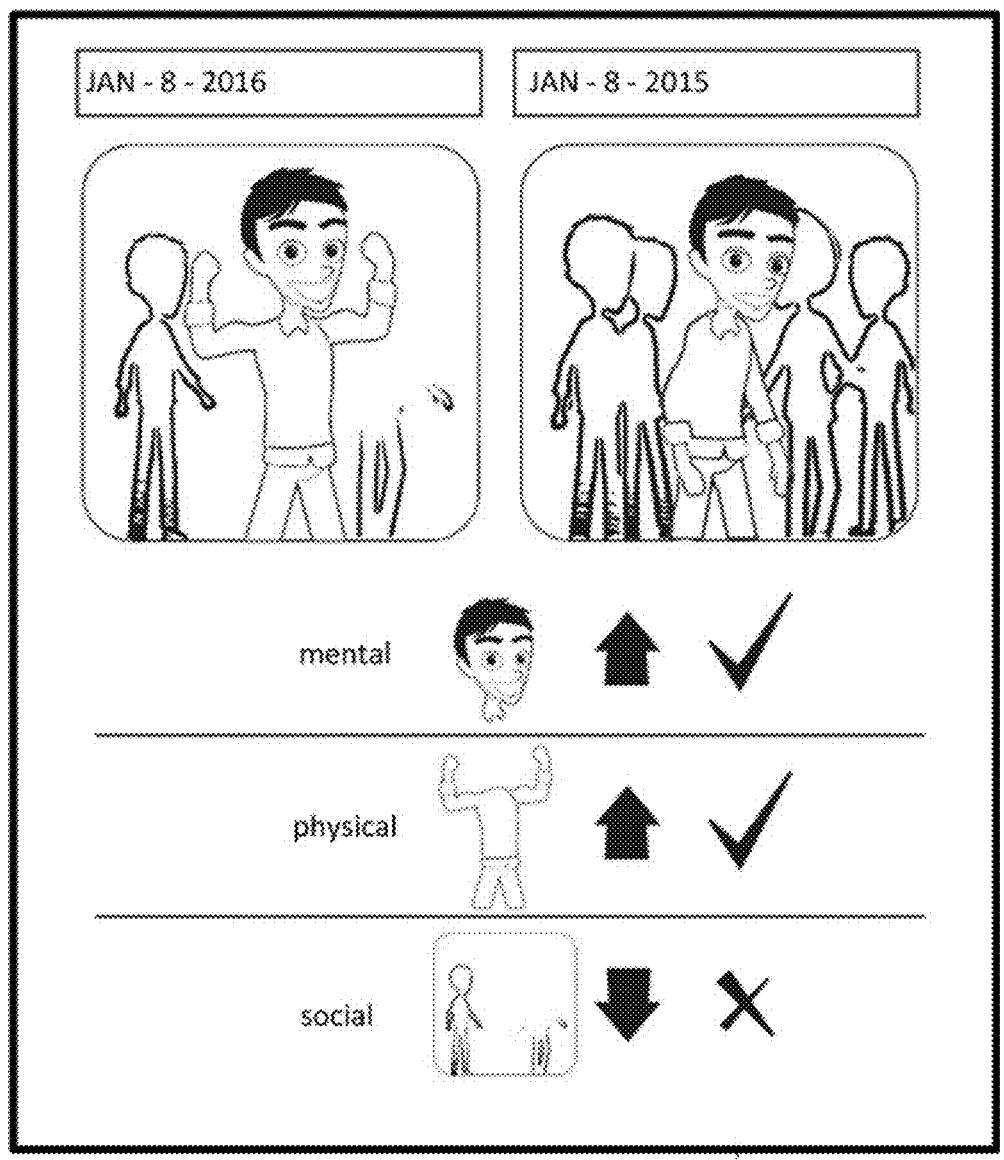
FIG. 29 illustrates an exemplary interfacing depicting a user's composite image at two times.

FIG. 29 illustrates a screenshot 2900 of a user interface similar to that of FIG. 26, but wherein instead of showing a comparison of the user to the word, the comparison shown is to the user at a different time. The output on the left is for the user on Jan. 8, 2016; the output on the right in comparison is for the user on Jan. 8, 2015.

Figure 29A:
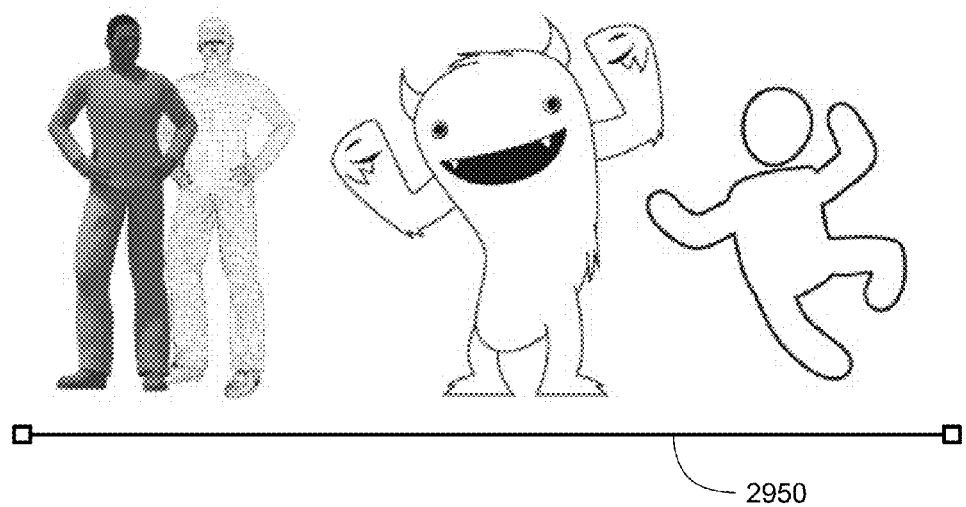
FIG. 29A illustrates that avatars may be more human like or more abstract.
Figure 30:
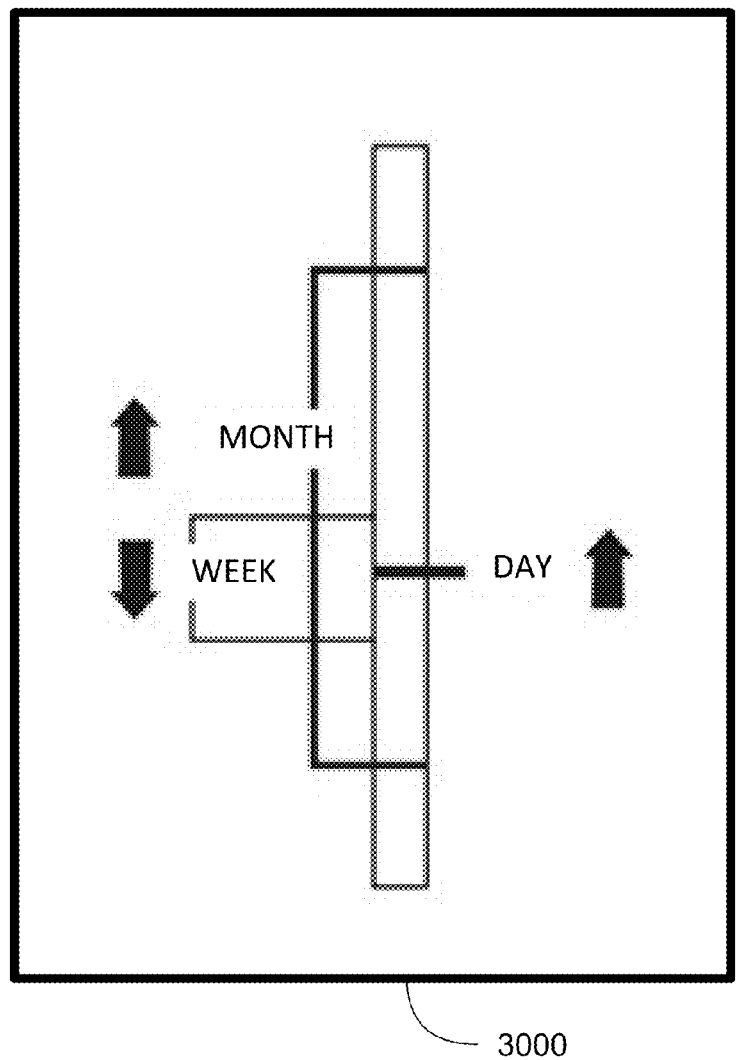
FIG. 30 illustrates an exemplary user interface demonstrating how trending and ranges of health status for an individual can be shown over time.
Figure 31:
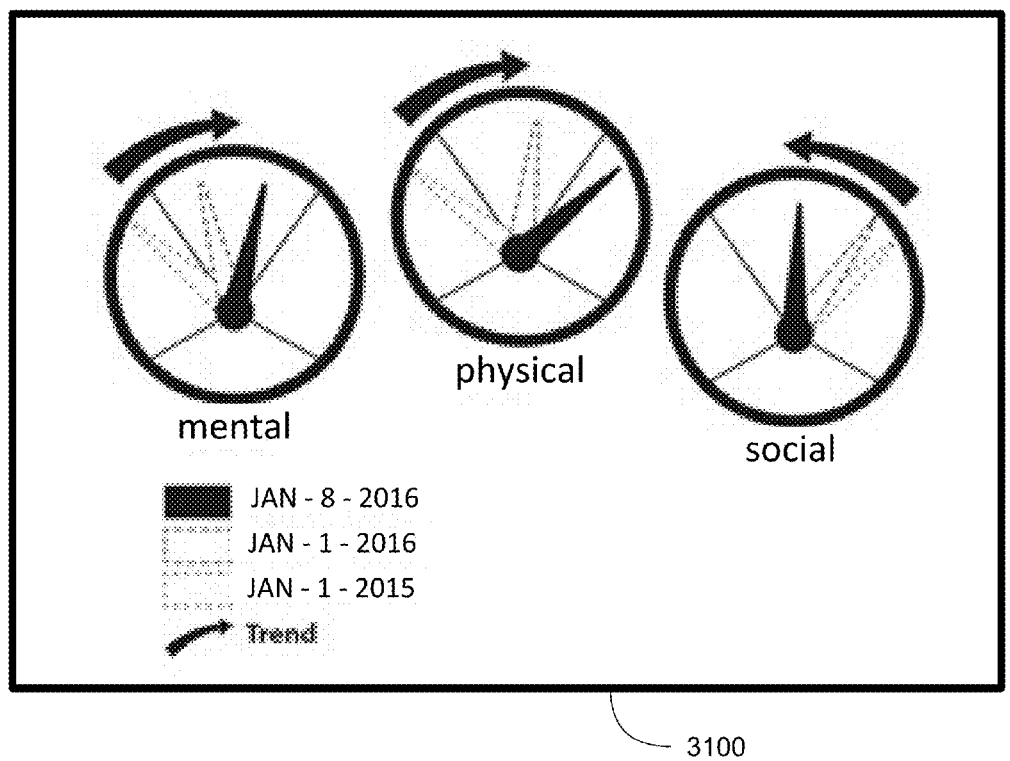
FIG. 31 illustrates an exemplary user interface including gauges.

It will further be appreciating that the avatar of the depictions may range from range from being human like to being abstract, as represented in the spectrum 2950 of avatars shown in FIG. 29A. Trending and ranges of health status for an individual also can be shown over time as seen in the visual representation of user interface 3000 of FIG. 30, and in the gauges of user interface 3100 of FIG. 31. Arrows can change size, shape, texture or color to illustrate different degrees or rates of trending and the impact this might have on overall health status. Such visualization methods also can be used to manually configure, by adjusting the value of trending and absolute values, evaluation prescription alert settings, or be used to show combined alerts and when they might be activated.

Recommendation Methodology

The recommendation methodology links directly to the analysis methods that will influence the profile components, static (rarely), slow change (occasionally), and rapid change (ongoing and dynamic). From the profile we get the individual's overall holistic health status now. This includes events, interventions and past history, which includes data patterns preceding and following events and interventions. Recommendations can have many different forms from reception of an alert that may have a dropdown of a list of potential actions with the top one being the most preferred, an example of which would be when an individual has a fall, they know that the target is close and has a free calendar and the options could be (in descending order): visit and check now, make a phone call, ring a neighbor, visit and check in 1-3 hours, text a neighbor, or ignore. Either option or by not responding for a given period of time would send out other alerts to either state the situation is in hand, or has still not been resolved.

Other recommendations could take the form of advice or education material on how best to deal with a certain condition or combination of conditions that related directly to an individual's profile. The methodology for this would be to create a file log for where the material can be found such as a url or other link. The file log would then be meta-tagged with relevant data that could be secondarily weighted. These would include things such as: trust, based on expert scores or where the data originated from (national body as opposed to a friend's recommendation); relevance for certain medical conditions, personality types, ability (such as to complete an exercise or a task such as cooking), and available budget; prior rating of the material by external users or users of the system internally; recommendation type and subtype (such as exercise, resistance exercise); language; cultural aspects (such as cultural style or accent of the presentation); and ease of understanding.

The recommendation engine would then populate a list of metatags based of the profile that would relate to factors such as highest ranked priorities, or active issues, and past use of, and rating of recommendations. These metatags would be then used to search the content database and then retrieve in rank order recommendations. The recommendations could be combined or grouped in categories such as: physical, mental, social; nutrition, activity, general; specific to a condition or conditions; now, today, this week, this month. The recommendations could also be used to meet user, expert or system defined goals such as goals that would be prescribed in a goal module of the system for: activity; weight loss; time out; time at work or reintroduction to employment; education and training; rehabilitation; or mental, physical or social performance.

Recommendations could be made by review by experts, users, or combination thereof. The recommendation reviews also could be tagged by an expert reviewer; grouped expert reviewers, such as those from an academic or industrial organization; or grouped expert users, such as those with specific physical, social, or mental health profiles. These recommended user group reviews could then be matched to users who had preference or a predicted preference for such recommended reviewed content.

Mobile Implementation

A preferred mobile implementation in accordance with one or more aspects and features of the invention now is described with reference to FIGS. 32-76. There are male and female icons sets for five surveys, fifteen questions in the application that covers physical (first question), mental (second question); and social (third question) inquiries relating to health and wellbeing. As seen in each user interface of FIGS. 32-76, the upper image relates to the input being received via the slider control for the question being addressed. There are three positions on each slider control for each question being addressed, as illustrated in these figures. These images are pulled from a library of twenty graduated images.

Figure 79:
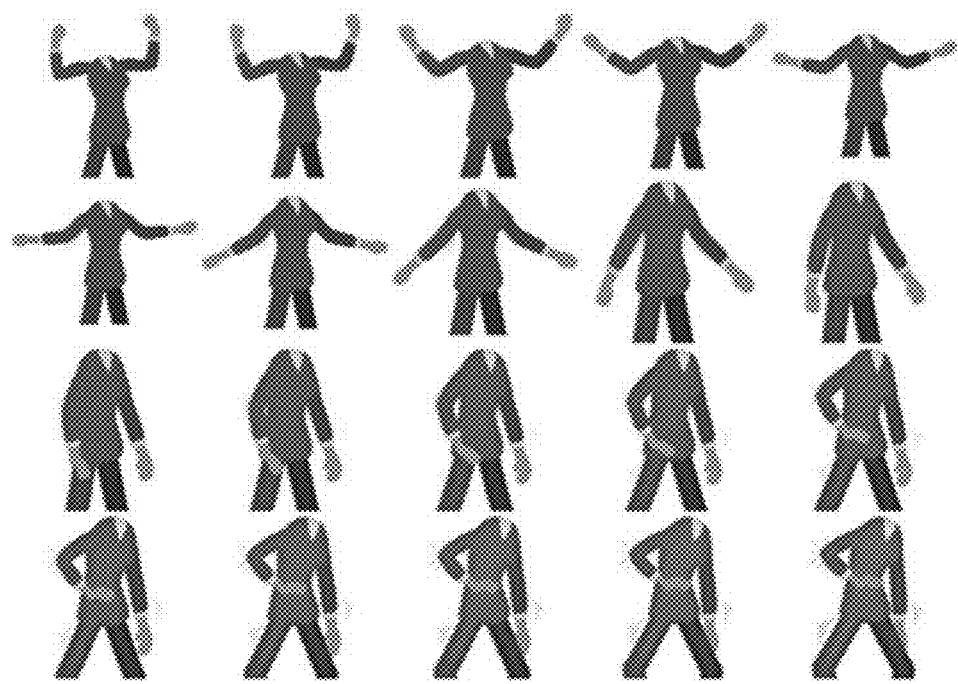
FIG. 79 shows twenty graduated images for physical health and wellbeing.
Figure 80:
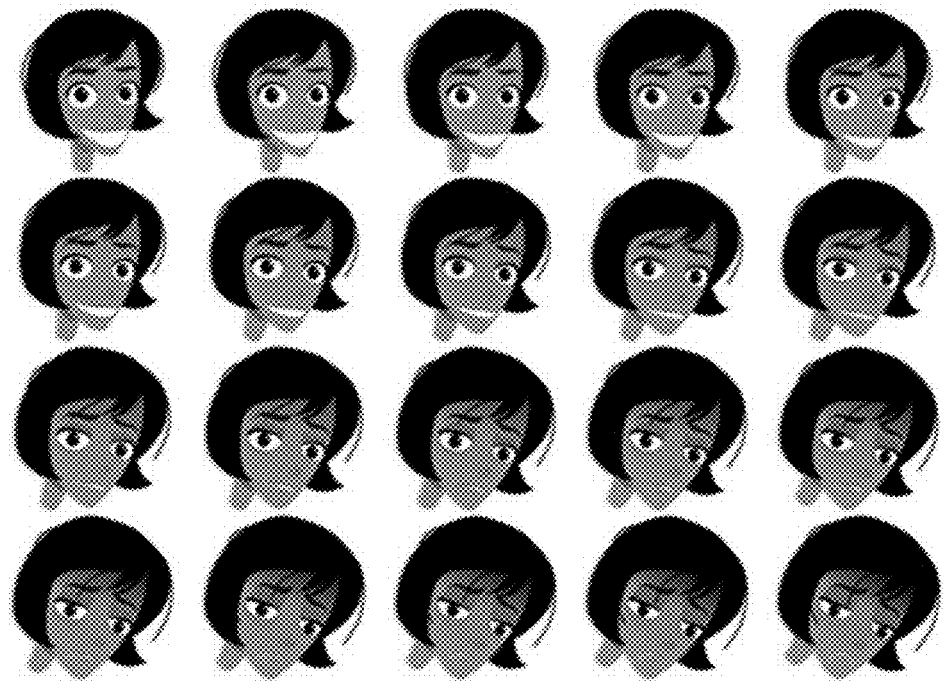
FIG. 80 shows twenty graduated images for mental health and wellbeing.
Figure 81:
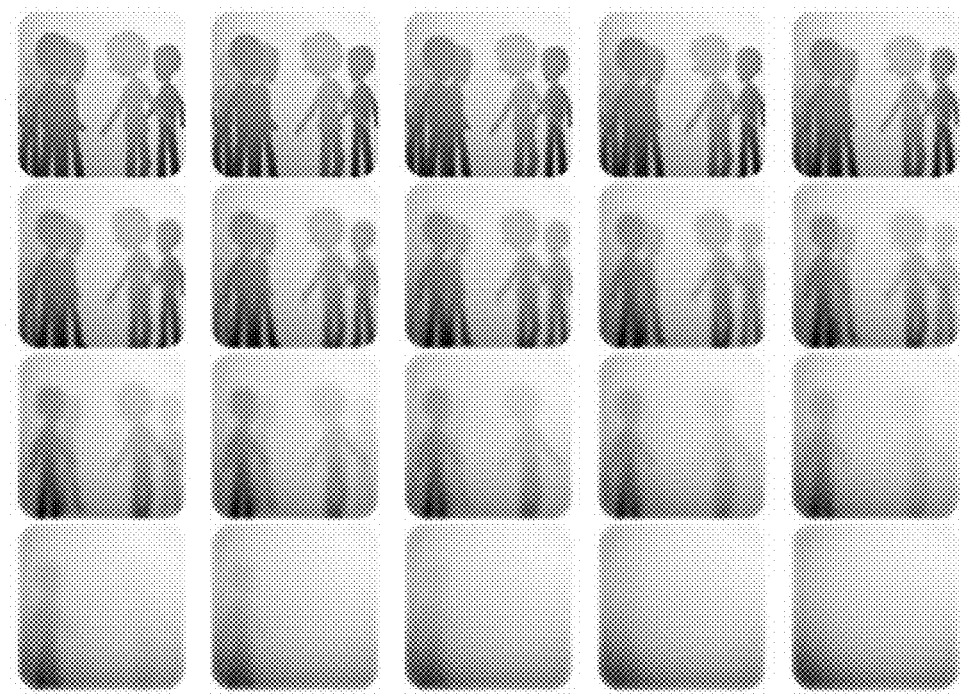
FIG. 81 shows twenty graduated images for social health and wellbeing.

For example, FIG. 79 shows twenty graduated images for physical health and wellbeing beginning in the upper left corner, proceeding across the row from left to right, and proceeding downward at the end of each row, with the lower right corner (worst) representing the extreme opposite to the upper left corner (best) of the array 7900 of images. Similarly, FIG. 80 shows twenty graduated images for mental health and wellbeing beginning in the upper left corner, proceeding across the row from left to right, and proceeding downward at the end of each row, with the lower right corner (worst) representing the extreme opposite to the upper left corner (best) of the array 8000 of images; and FIG. 81 shows twenty graduated images social health and wellbeing beginning in the upper left corner, proceeding across the row from left to right, and proceeding downward at the end of each row, with the lower right corner (worst) representing the extreme opposite (worst) to the upper left corner (best) of the array 8100 of images.

The lower portion of each slider control is composed of a range from low to high and a slider therebetween. Depending on the question and the point on the slider that is selected, the picture above changes, as can be seen, for example, in the nine depictions of the user interface 3200.

Figure 32:
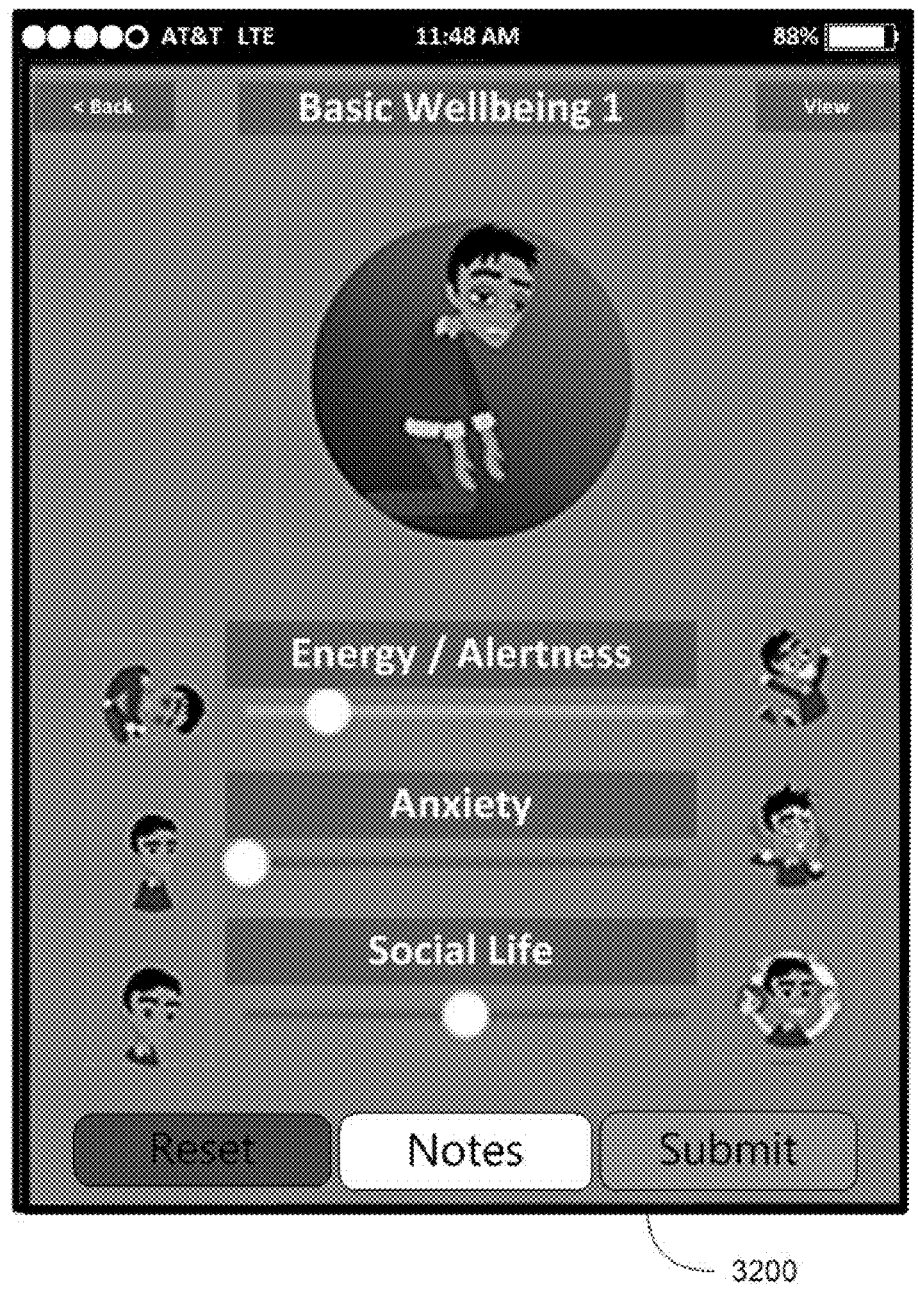
FIG. 32 illustrates a user interface in which user input regarding energy is being received by sliding the slider control for "Energy/Alertness" to the position as illustrated therein.

Thus, FIG. 32 illustrates a user interface 3200 in which user input regarding energy is being received by sliding the slider control for "Energy/Alertness" to the position as illustrated therein.

Figure 33:
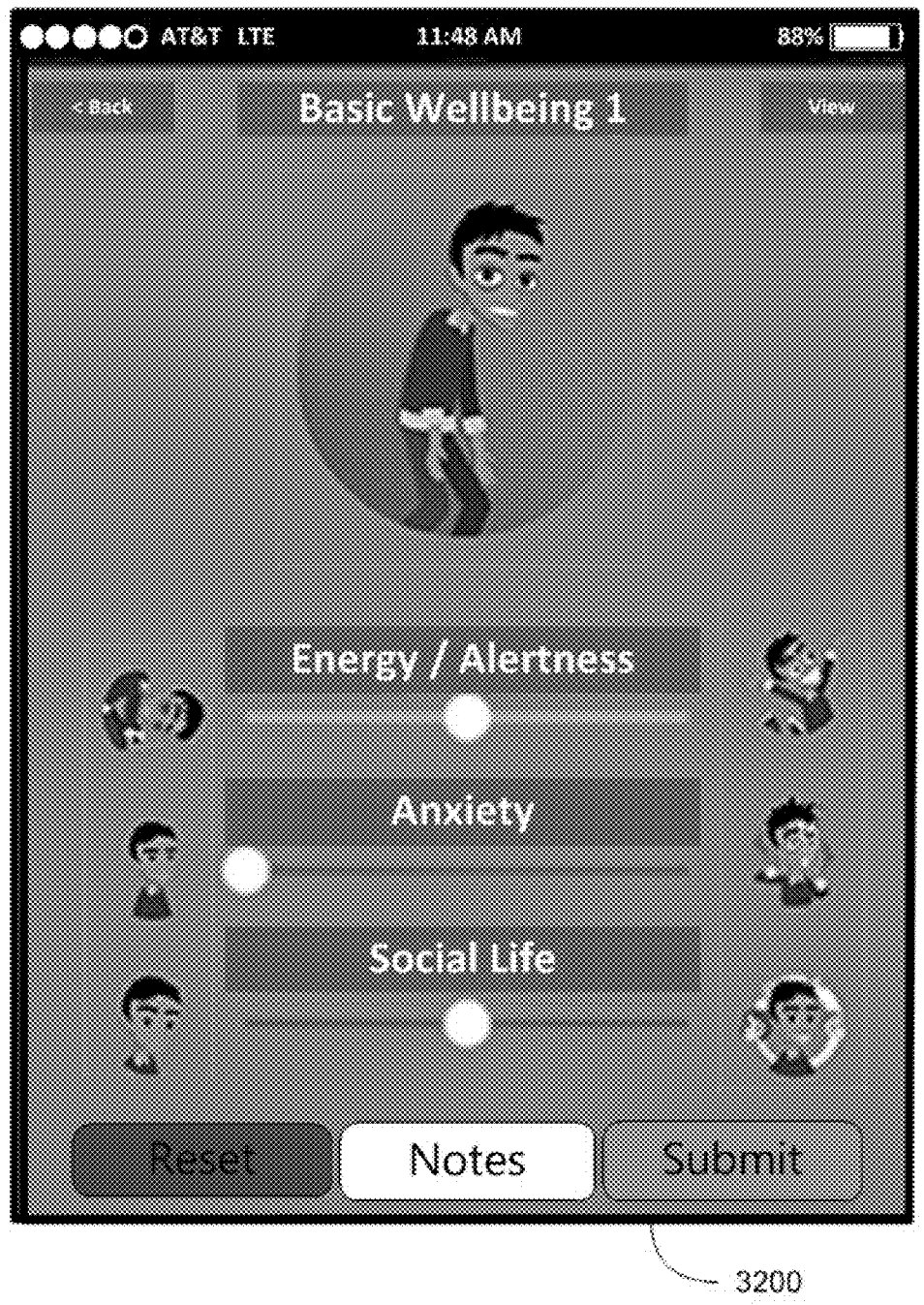
FIGS. 33-34 each illustrates the user interface of FIG. 32, in which user input regarding energy is being received by sliding the slider control for "Energy/Alertness" to a new position as illustrated.

FIG. 33 illustrates the same user interface 3200 in which user input regarding energy is being received by sliding the slider control for "Energy/Alertness" to a new position as illustrated therein.

Figure 34:
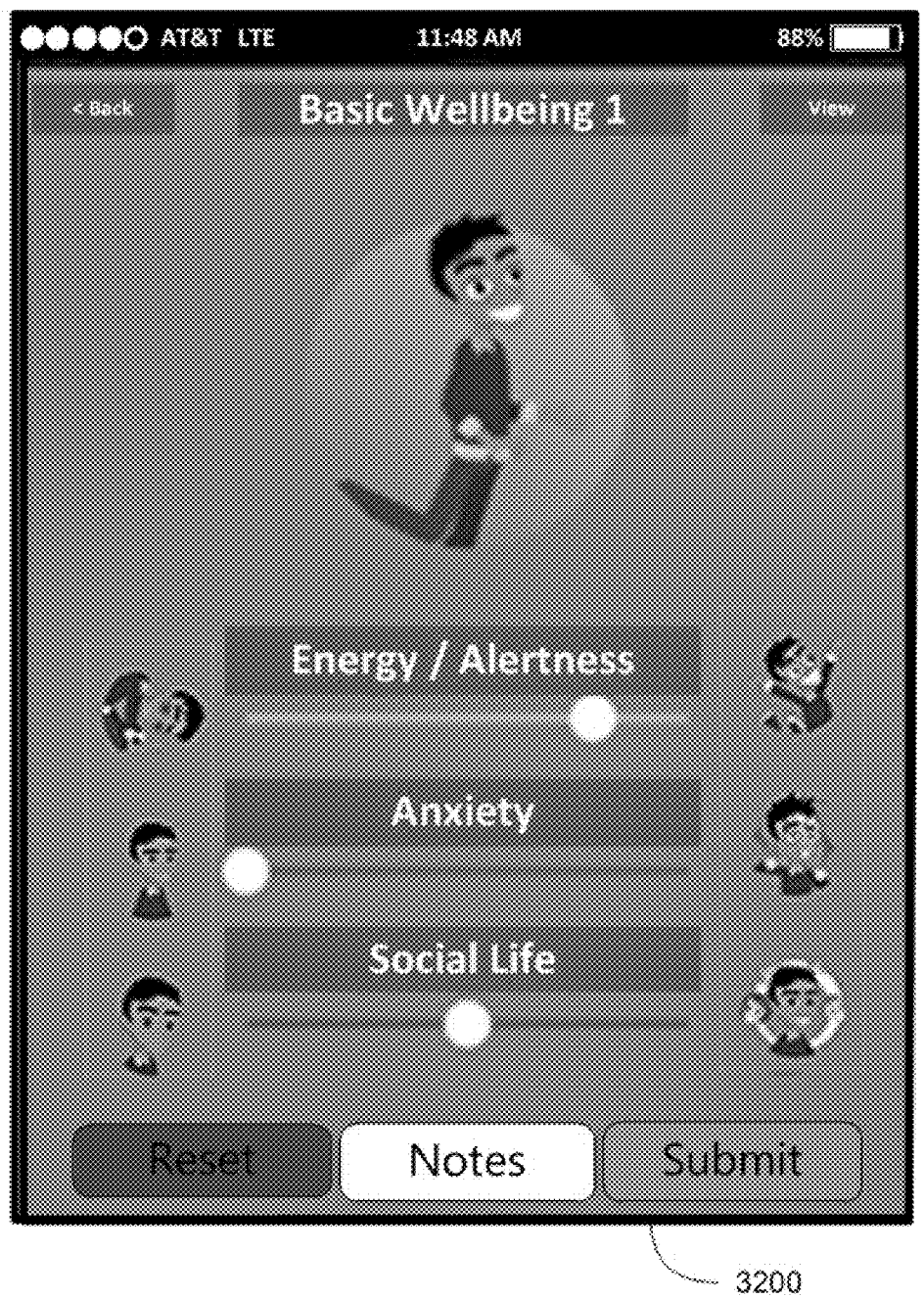

FIG. 34 illustrates the same user interface 3200 in which user input regarding energy is being received by sliding the slider control for "Energy/Alertness" to a new position as illustrated therein.

Figure 35:
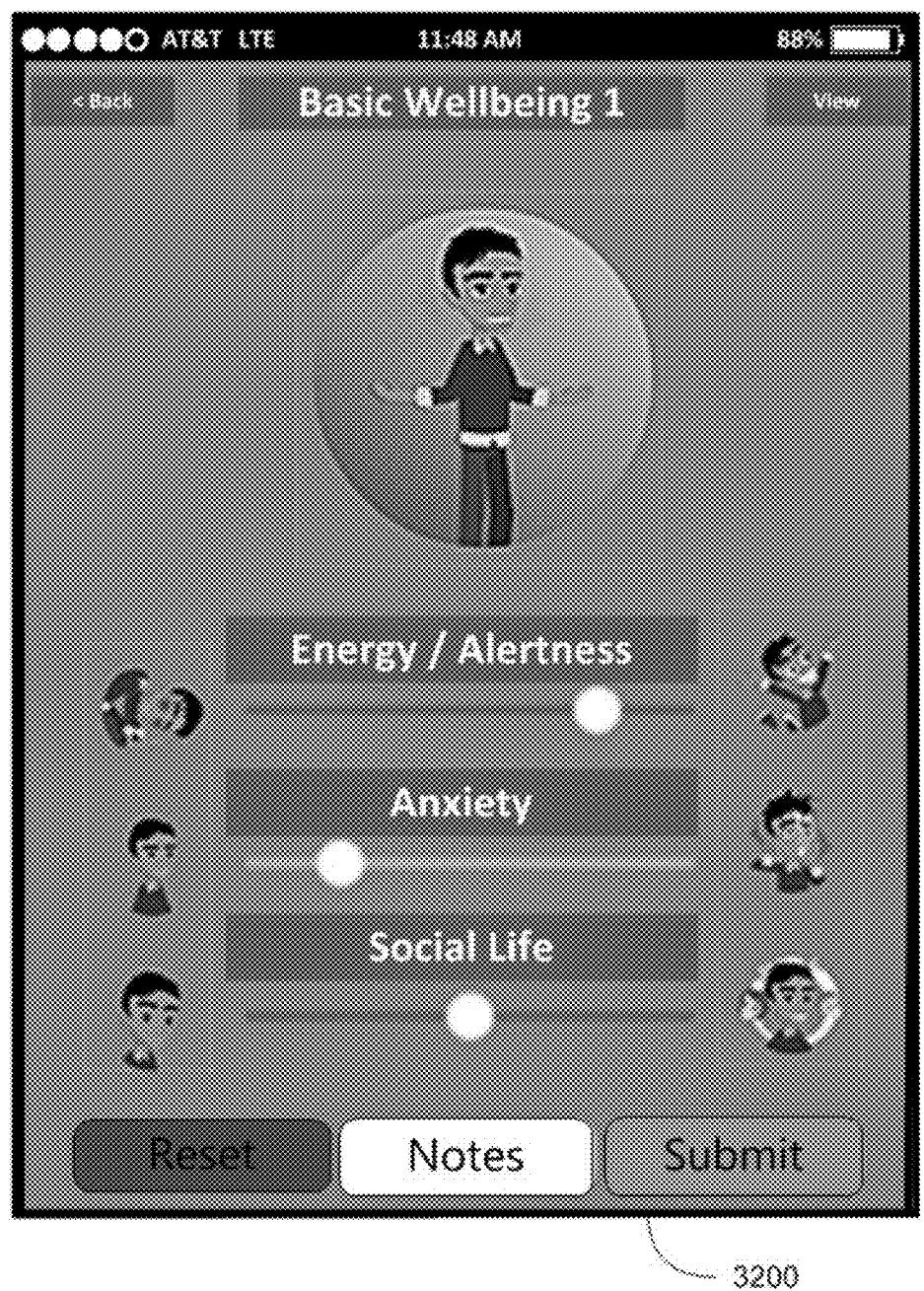
FIG. 35 illustrates the user interface of FIG. 32, in which user input regarding anxiety is being received by sliding the slider control for "Anxiety" to a position as illustrated therein.

FIG. 35 illustrates the same user interface 3200 in which user input regarding anxiety is being received by sliding the slider control for "Anxiety" to a position as illustrated therein.

Figure 36:
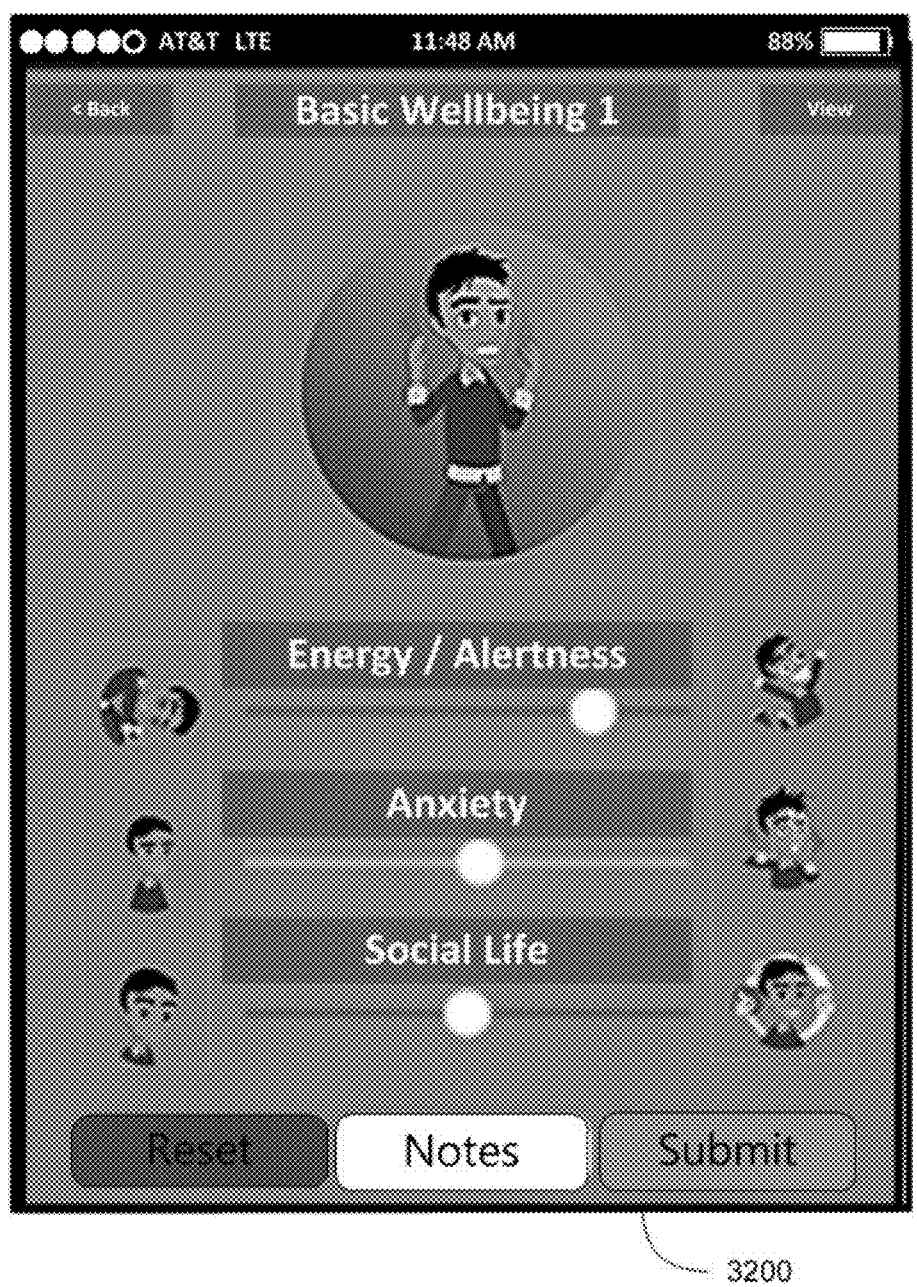
FIGS. 36-37 each illustrates the user interface of FIG. 32, in which user input regarding anxiety is being received by sliding the slider control for "Anxiety" to a new position as illustrated therein.

FIG. 36 illustrates the same user interface 3200 in which user input regarding anxiety is being received by sliding the slider control for "Anxiety" to a new position as illustrated therein.

Figure 37:
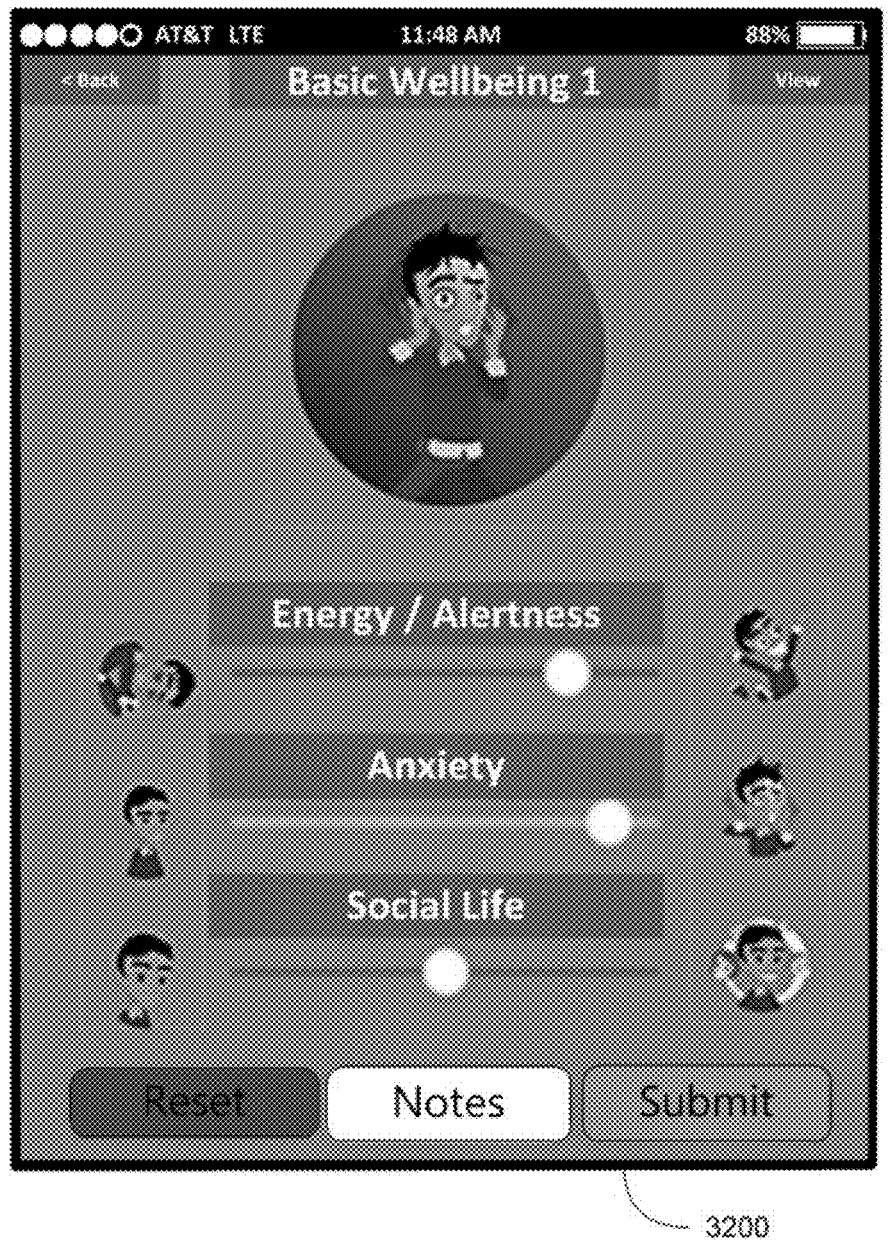

FIG. 37 illustrates the same user interface 3200 in which user input regarding anxiety is being received by sliding the slider control for "Anxiety" to a new position as illustrated therein.

Figure 38:
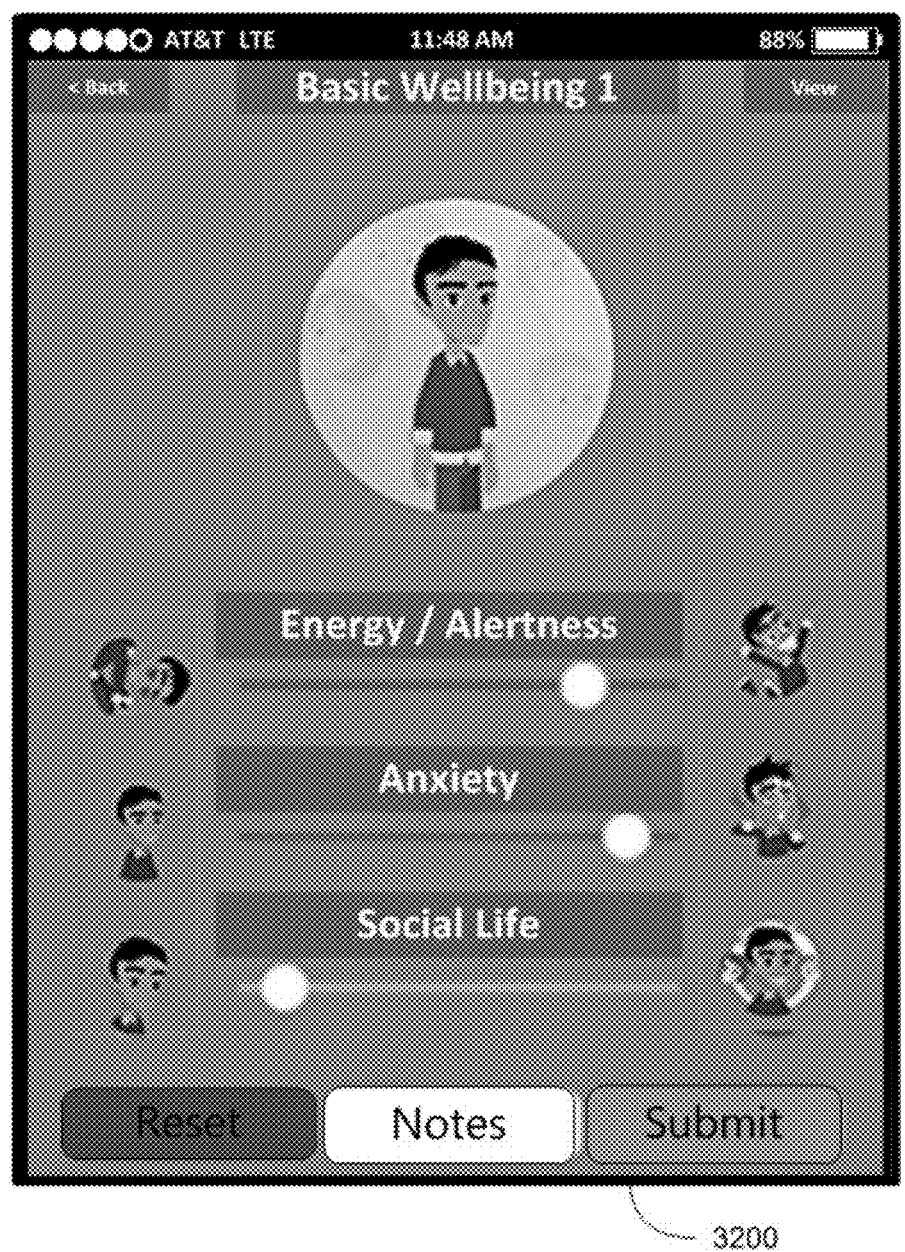
FIG. 38 illustrates the user interface of FIG. 32, in which user input regarding social life is being received by sliding the slider control for "Social Life" to a position as illustrated therein.

FIG. 38 illustrates the same user interface 3200 in which user input regarding social life is being received by sliding the slider control for "Social Life" to a position as illustrated therein.

Figure 39:
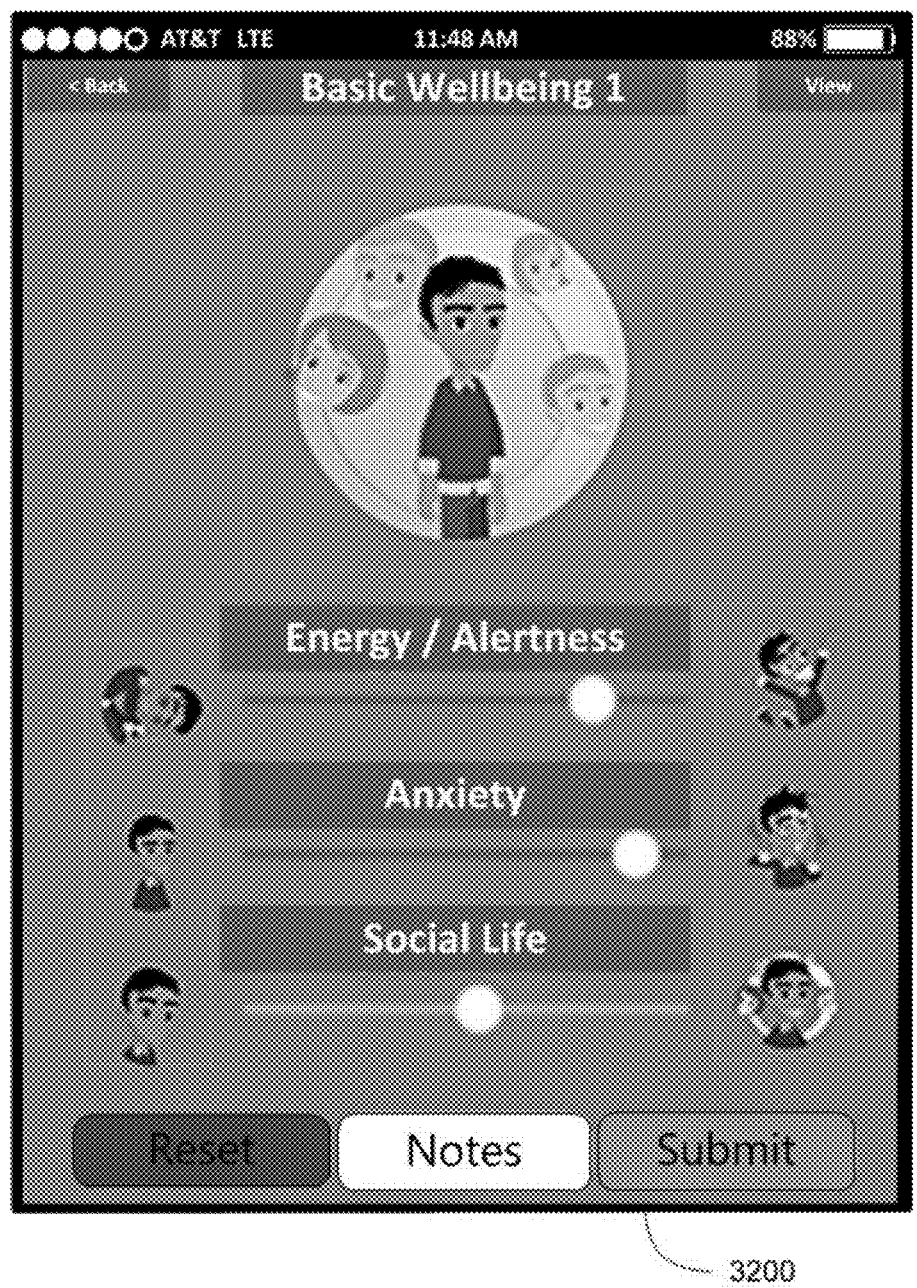
FIGS. 39-40 illustrates the user interface of FIG. 32, in which user input regarding social life is being received by sliding the slider control for "Social Life" to a new position as illustrated therein.

FIG. 39 illustrates the same user interface 3200 in which user input regarding social life is being received by sliding the slider control for "Social Life" to a new position as illustrated therein.

Figure 40:
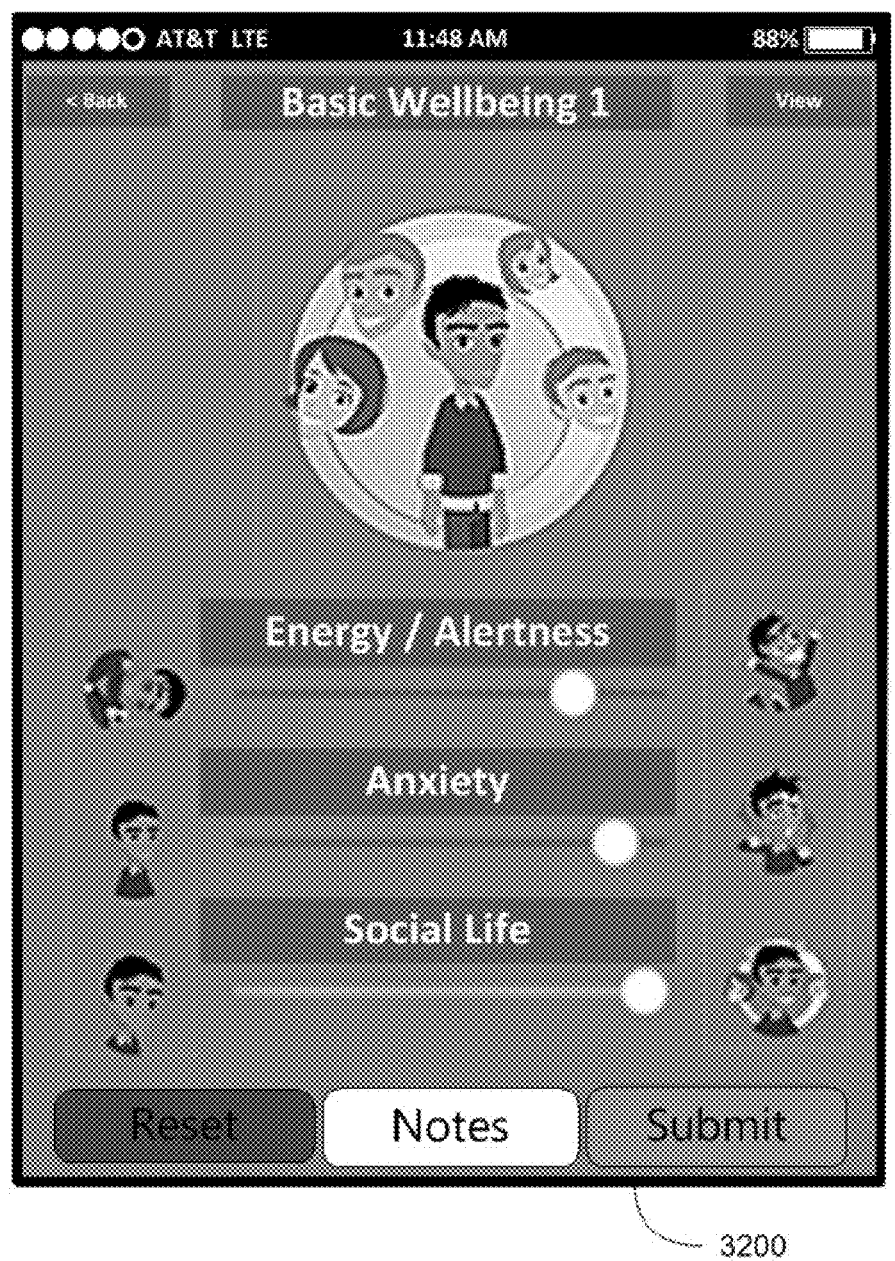

FIG. 40 illustrates the same user interface 3200 in which user input regarding social life is being received by sliding the slider control for "Social Life" to a new position as illustrated therein.

Figure 41:
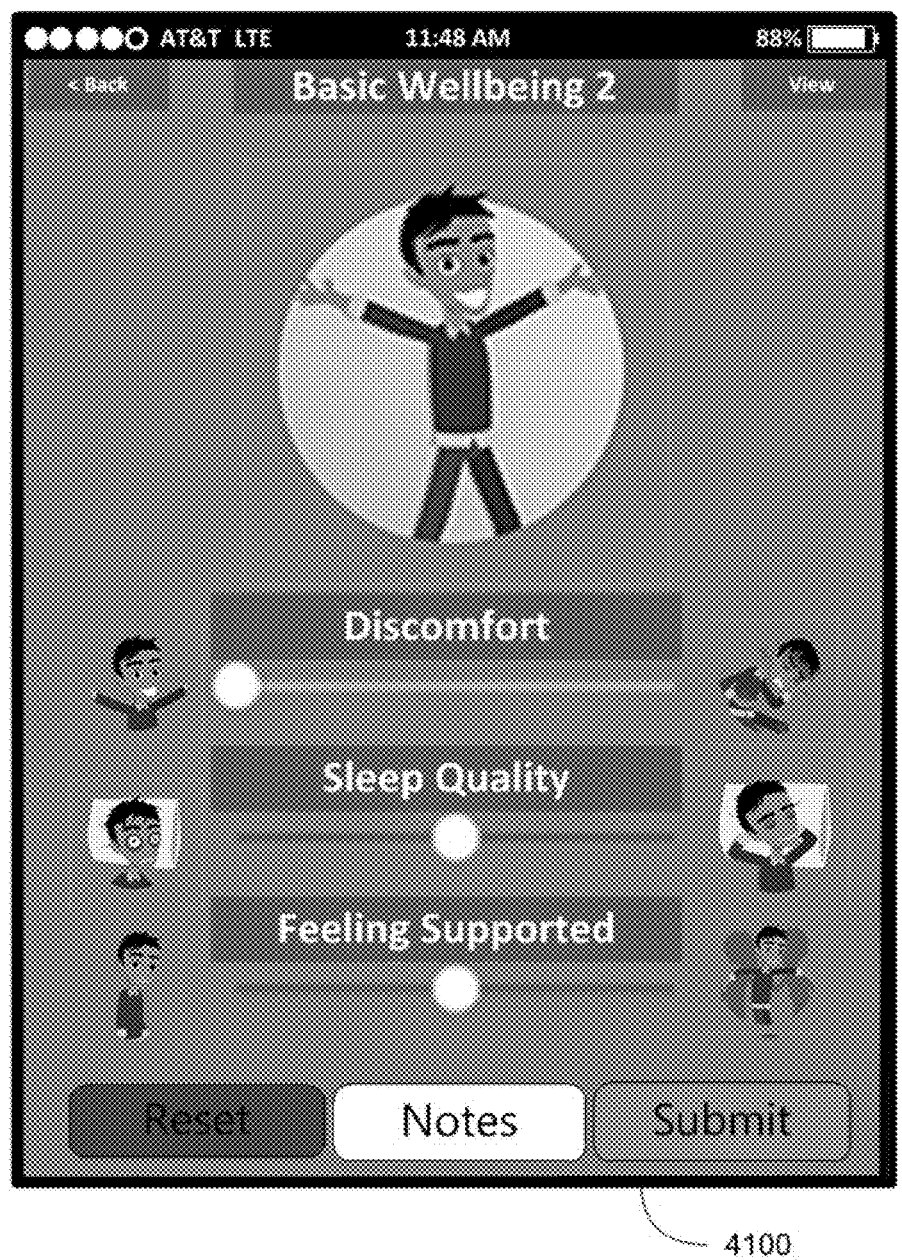
FIG. 41 illustrates a user interface in which user input regarding discomfort is being received by sliding the slider control for "Discomfort" to the position as illustrated therein.

FIG. 41 illustrates a user interface 4100 in which user input regarding discomfort is being received by sliding the slider control for "Discomfort" to the position as illustrated therein.

Figure 42:
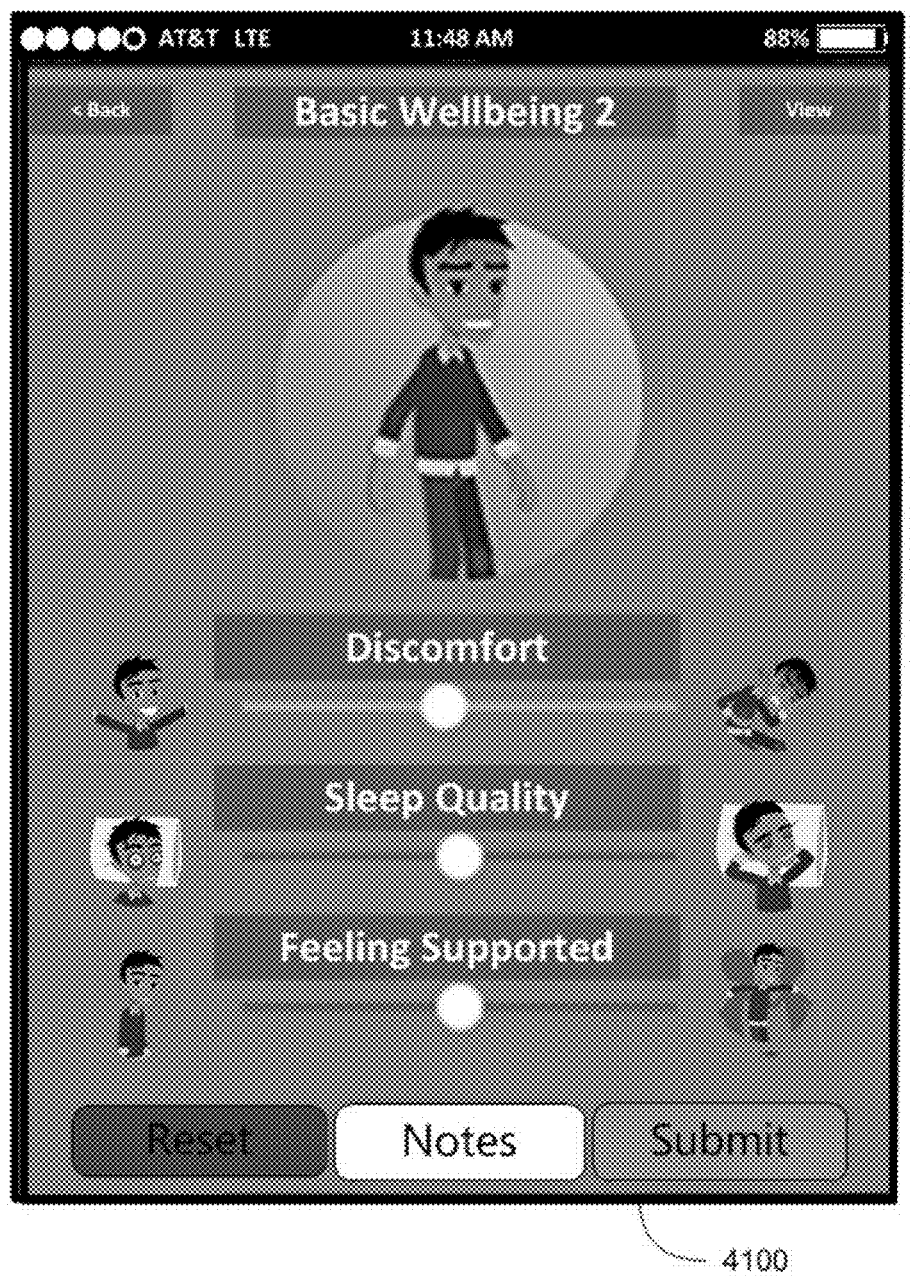
FIGS. 42-43 each illustrates the user interface of FIG. 41 in which user input regarding discomfort is being received by sliding the slider control for "Discomfort" to a new position as illustrated therein.

FIG. 42 illustrates the same user interface 4100 in which user input regarding discomfort is being received by sliding the slider control for "Discomfort" to a new position as illustrated therein.

Figure 43:
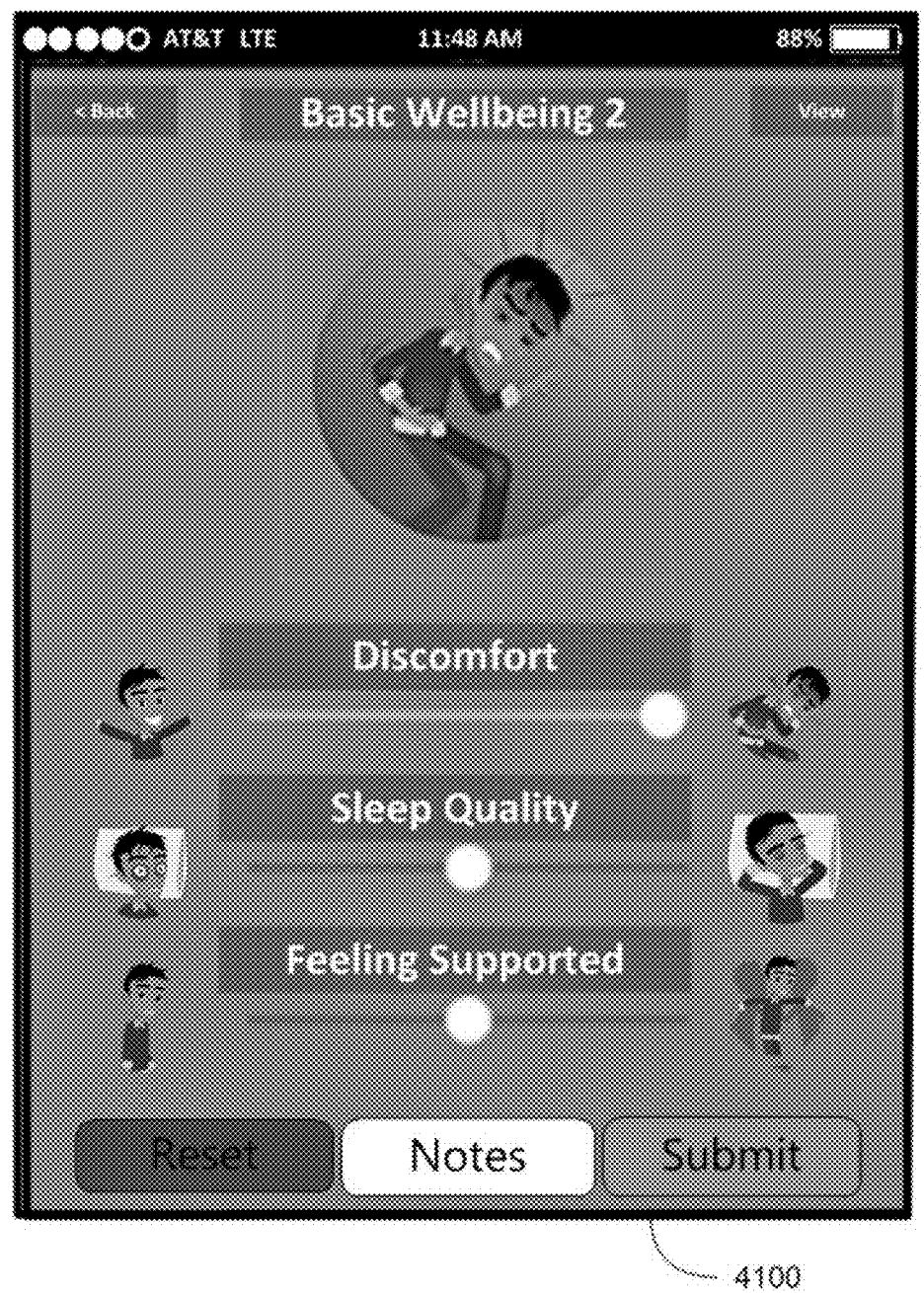

FIG. 43 illustrates the same user interface 4100 in which user input regarding discomfort is being received by sliding the slider control for "Discomfort" to a position as illustrated therein.

Figure 44:
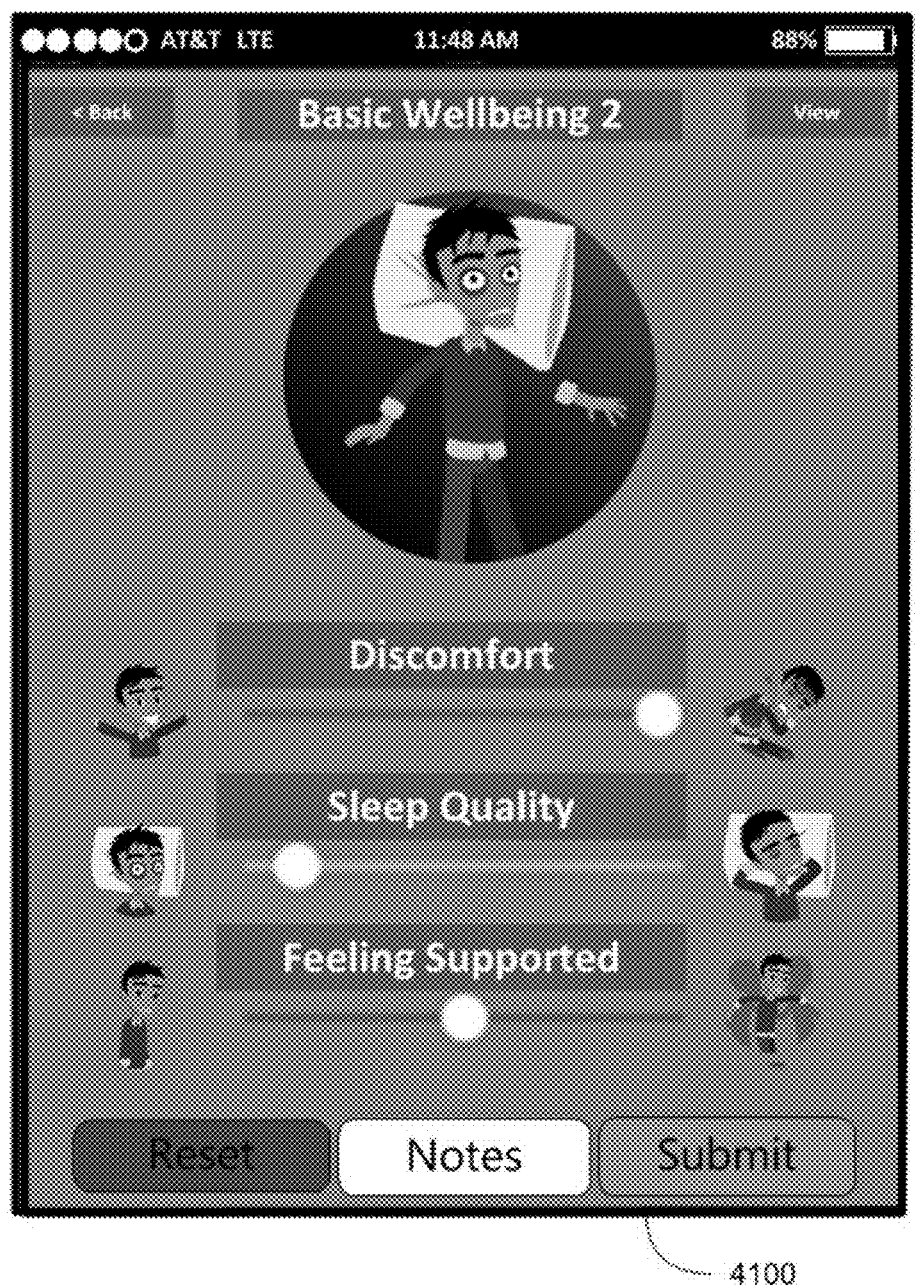
FIG. 44 illustrates the user interface of FIG. 41 in which user input regarding sleep comfort is being received by sliding the slider control for "Sleep Comfort" to a new position as illustrated therein.

FIG. 44 illustrates the same user interface 4100 in which user input regarding sleep comfort is being received by sliding the slider control for "Sleep Comfort" to a new position as illustrated therein.

Figure 45:
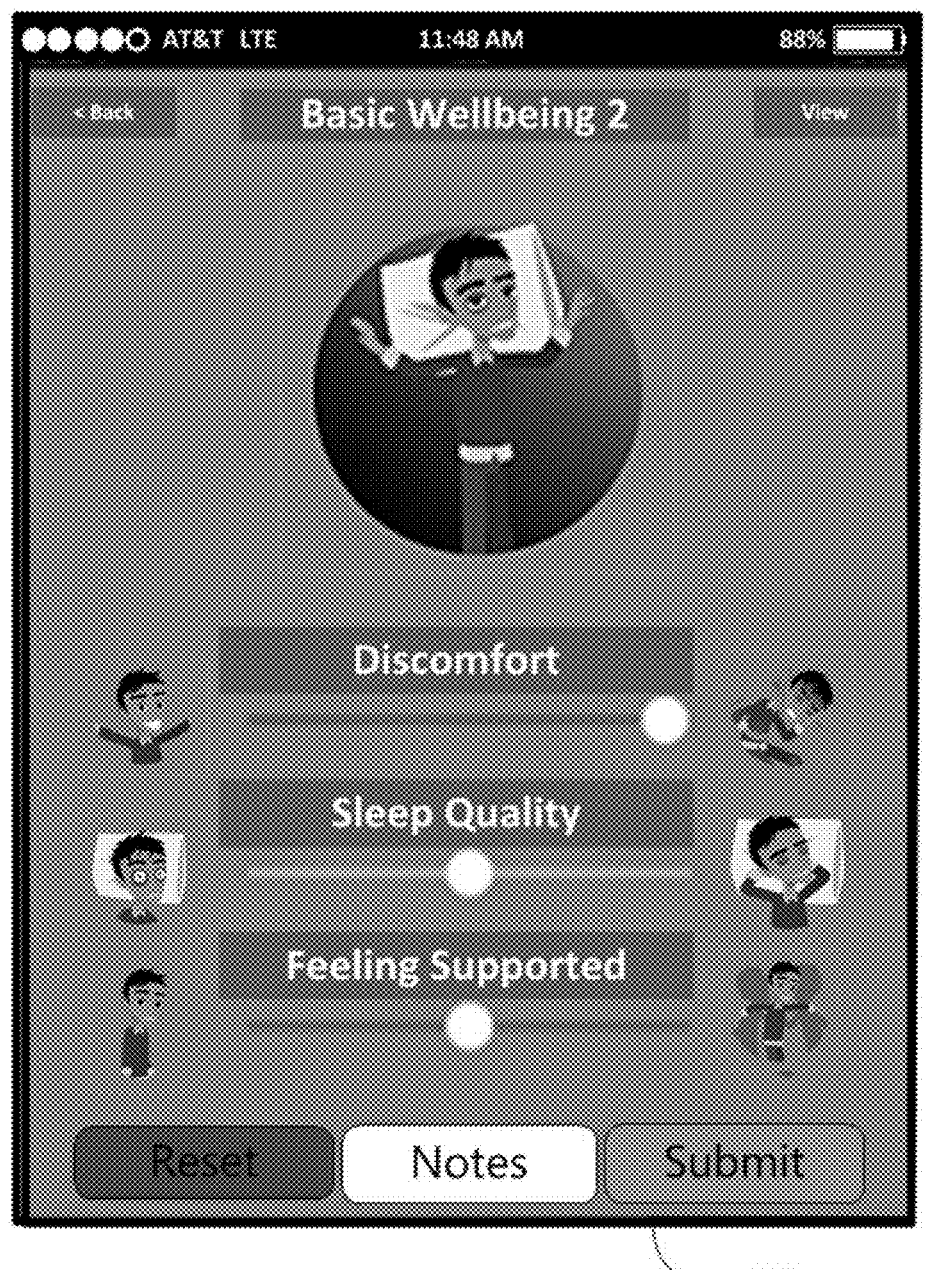
FIGS. 45-46 each illustrates the user interface of FIG. 44 in which user input regarding sleep comfort is being received by sliding the slider control for "Sleep Comfort" to a new position as illustrated therein.

FIG. 45 illustrates the same user interface 4100 in which user input regarding sleep comfort is being received by sliding the slider control for "Sleep Comfort" to a new position as illustrated therein.

Figure 46:
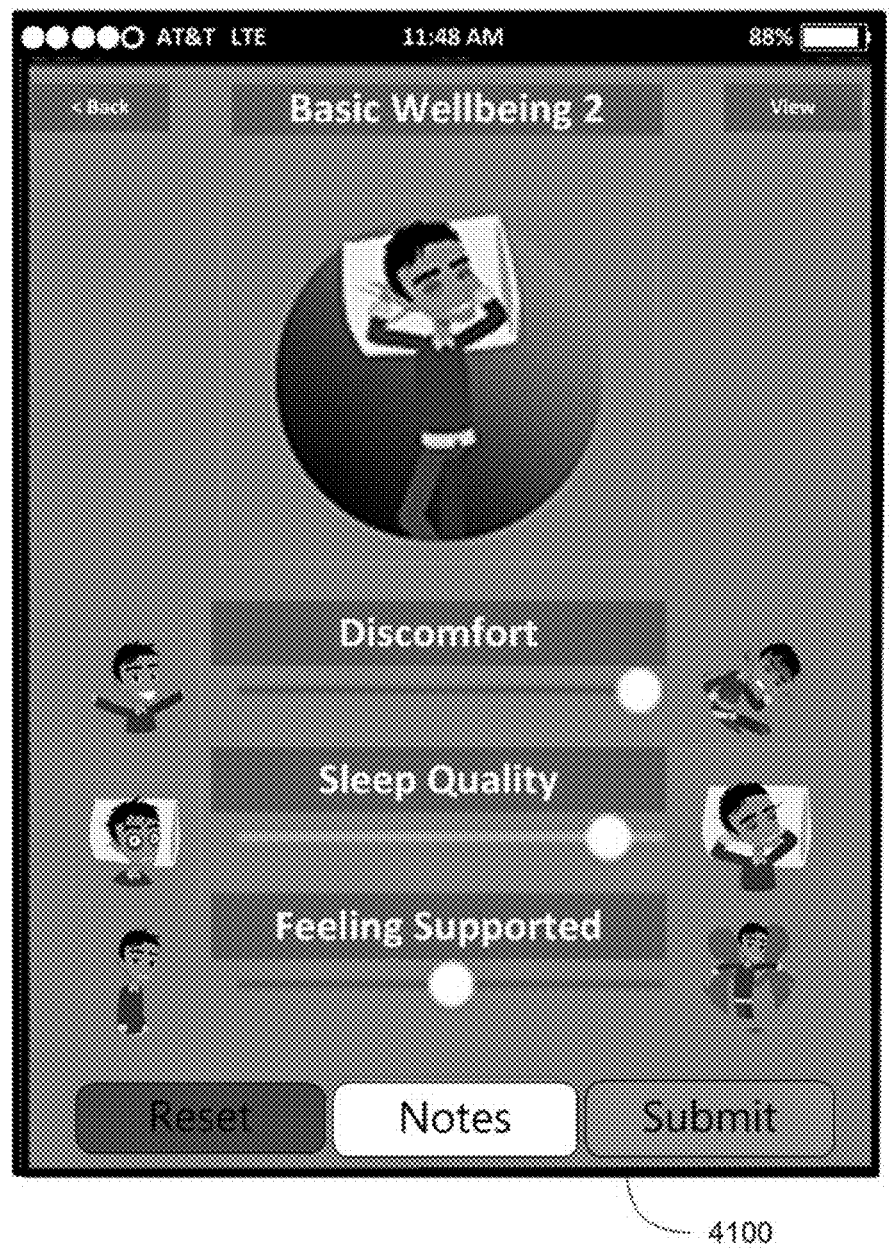

FIG. 46 illustrates the same user interface 4100 in which user input regarding sleep comfort is being received by sliding the slider control for "Sleep Comfort" to a position as illustrated therein.

Figure 47:
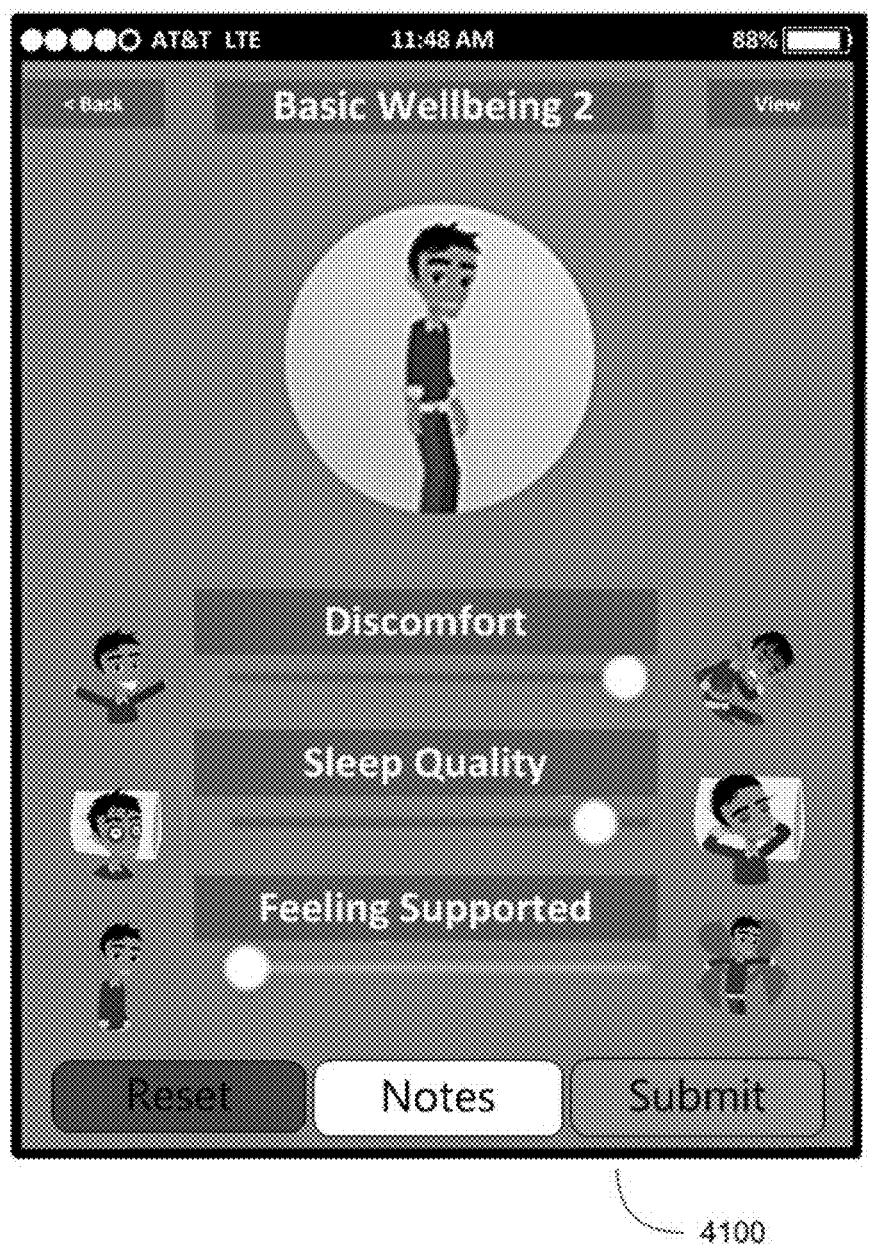
FIG. 47 illustrates the user interface of FIG. 41 in which user input regarding feeling supported is being received by sliding the slider control for "Feeling Supported" to a new position as illustrated therein.

FIG. 47 illustrates the same user interface 4100 in which user input regarding feeling supported is being received by sliding the slider control for "Feeling Supported" to a new position as illustrated therein.

Figure 48:
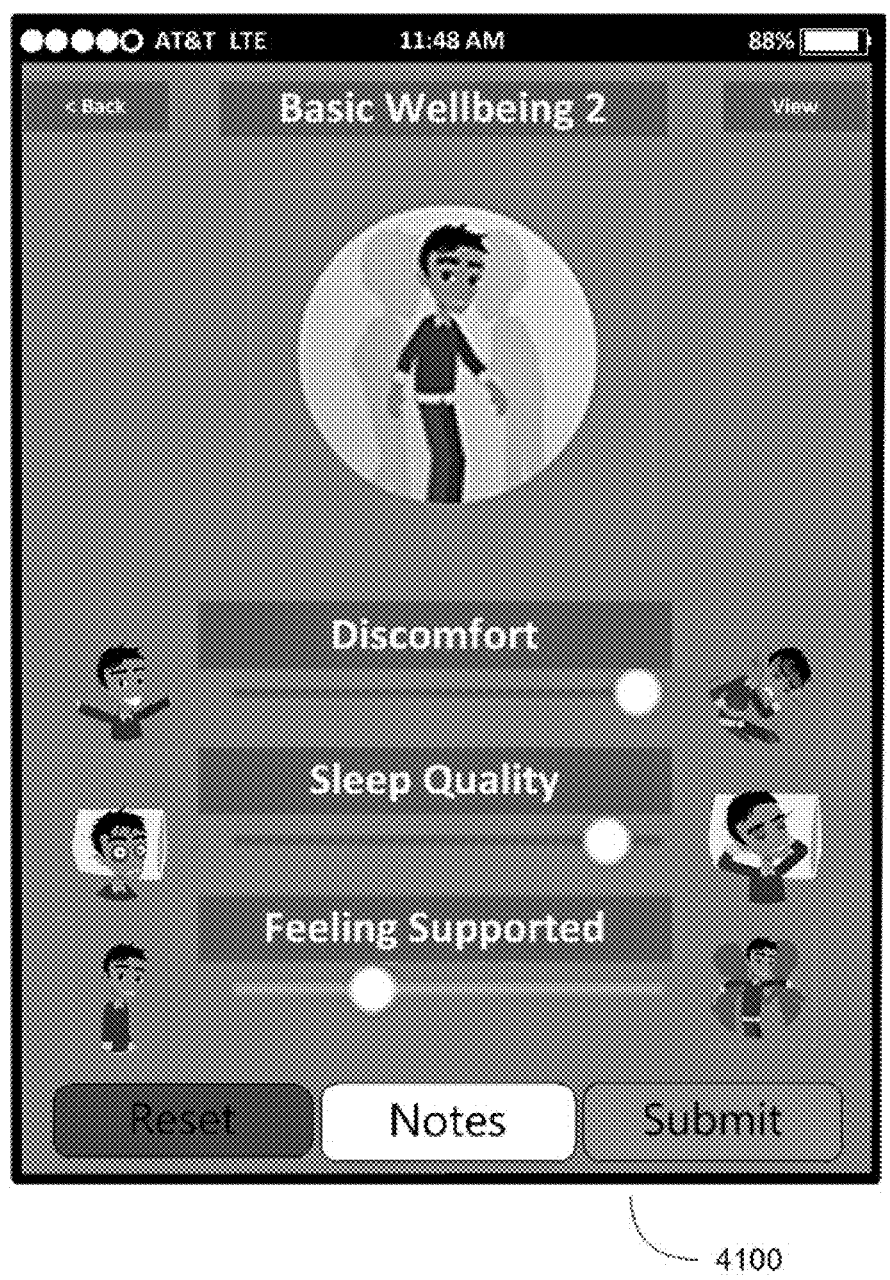
FIGS. 48-49 each illustrates the user interface of FIG. 47 in which user input regarding feeling supported is being received by sliding the slider control for "Feeling Supported" to a new position as illustrated therein.

FIG. 48 illustrates the same user interface 4100 in which user input regarding feeling supported is being received by sliding the slider control for "Feeling Supported" to a new position as illustrated therein.

Figure 49:
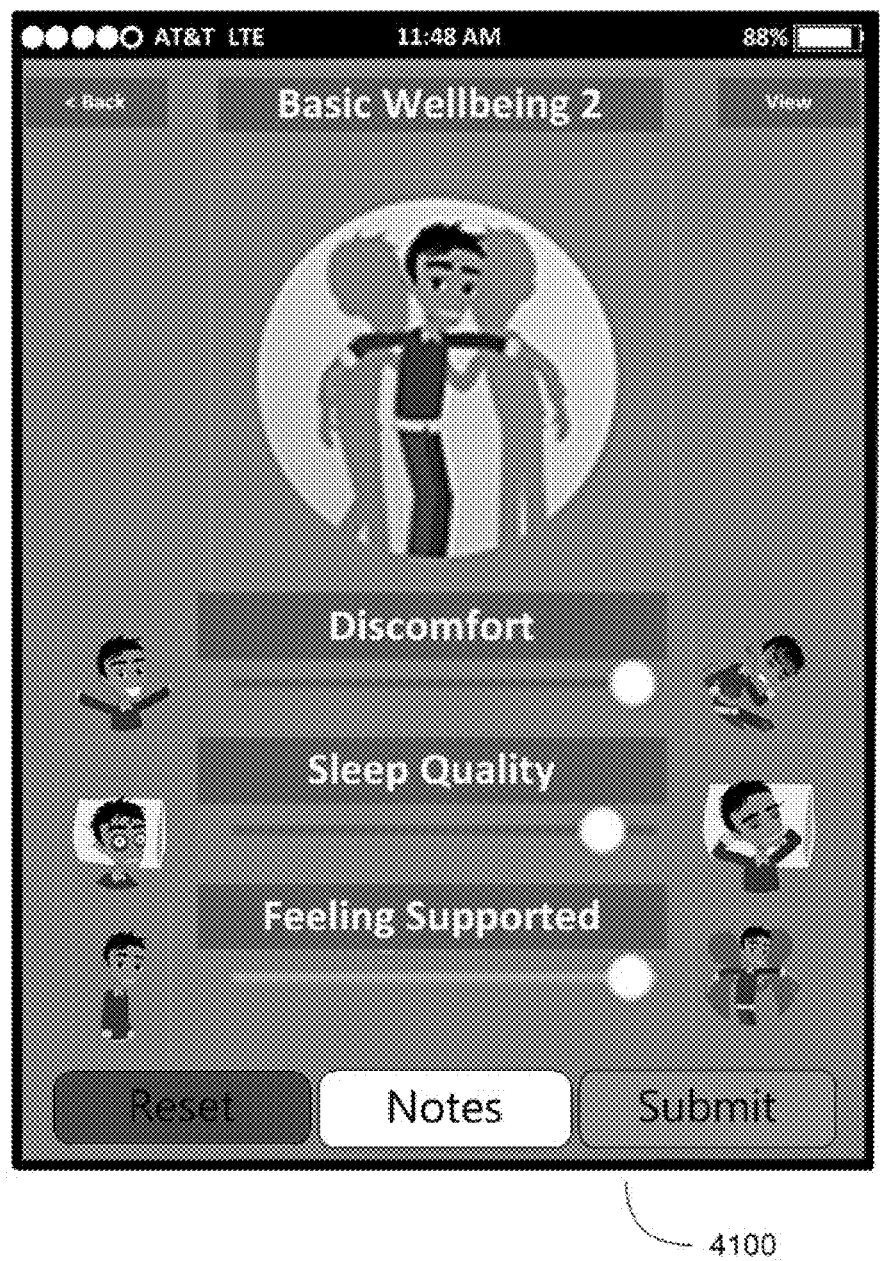

FIG. 49 illustrates the same user interface 4100 in which user input regarding sleep feeling supported is being received by sliding the slider control for "Feeling Supported" to a position as illustrated therein.

Figure 49A:
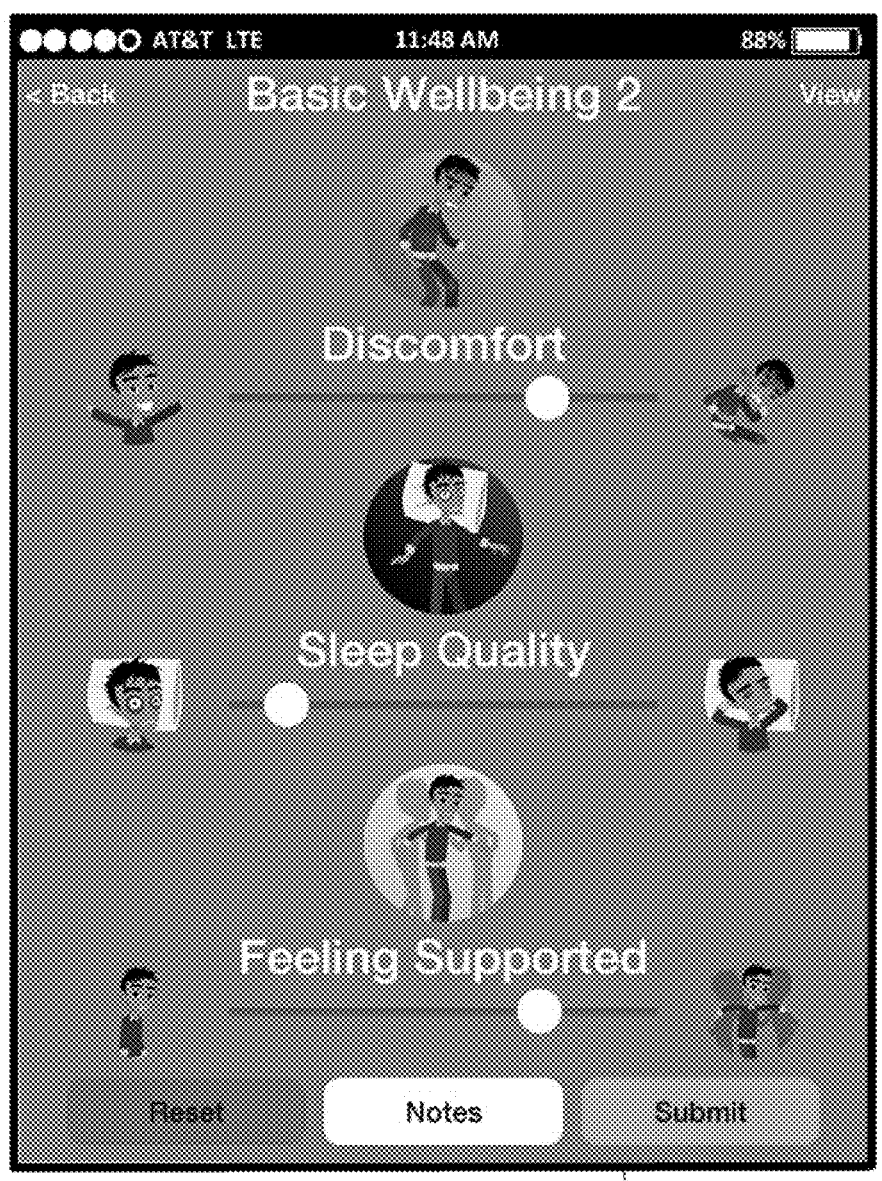
FIG. 49A illustrates an alternative user interface in which user input regarding all three of discomfort, sleep quality, and feeling supported is being received by sliding the respective slider controls to the respective positions as illustrated therein.

FIG. 49A is illustrates an alternative user interface 4950 in which user input regarding all three of discomfort, sleep quality, and feeling supported is being received by sliding the respective slider controls to the respective positions as illustrated therein, with each respective output being shown in the interface 4950. This screenshot further illustrates the separately alteration that is enabled in the interface regarding each metric, which is seen for example by the activation of the slider for "Discomfort"; as such the individual can review all three inputs in one interface and alter or update them as necessary or desired.

Figure 50:
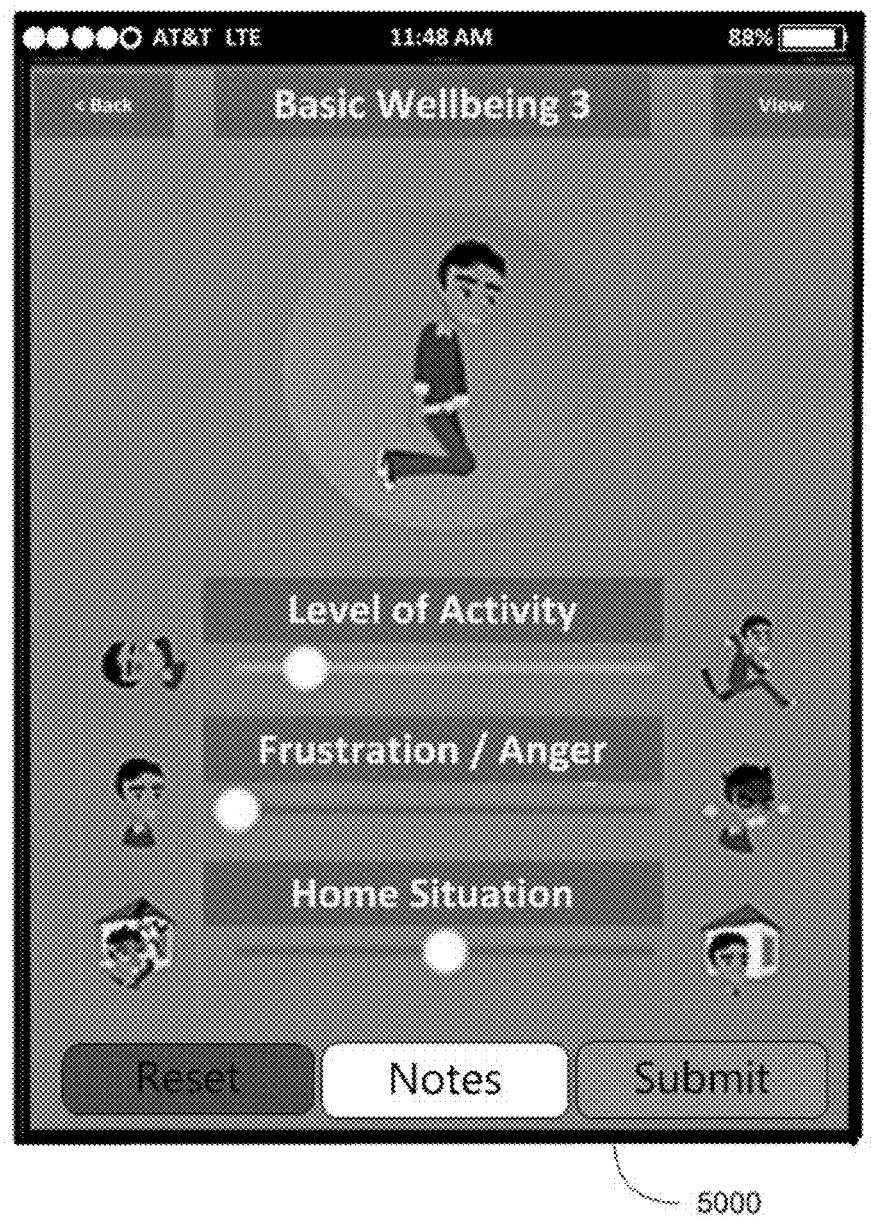
FIG. 50 illustrates a user interface in which user input regarding a level of activity is being received by sliding the slider control for "Level of Activity" to a position as illustrated therein.

FIG. 50 illustrates a user interface 5000 in which user input regarding a level of activity is being received by sliding the slider control for "Level of Activity" to a position as illustrated therein.

Figure 51:
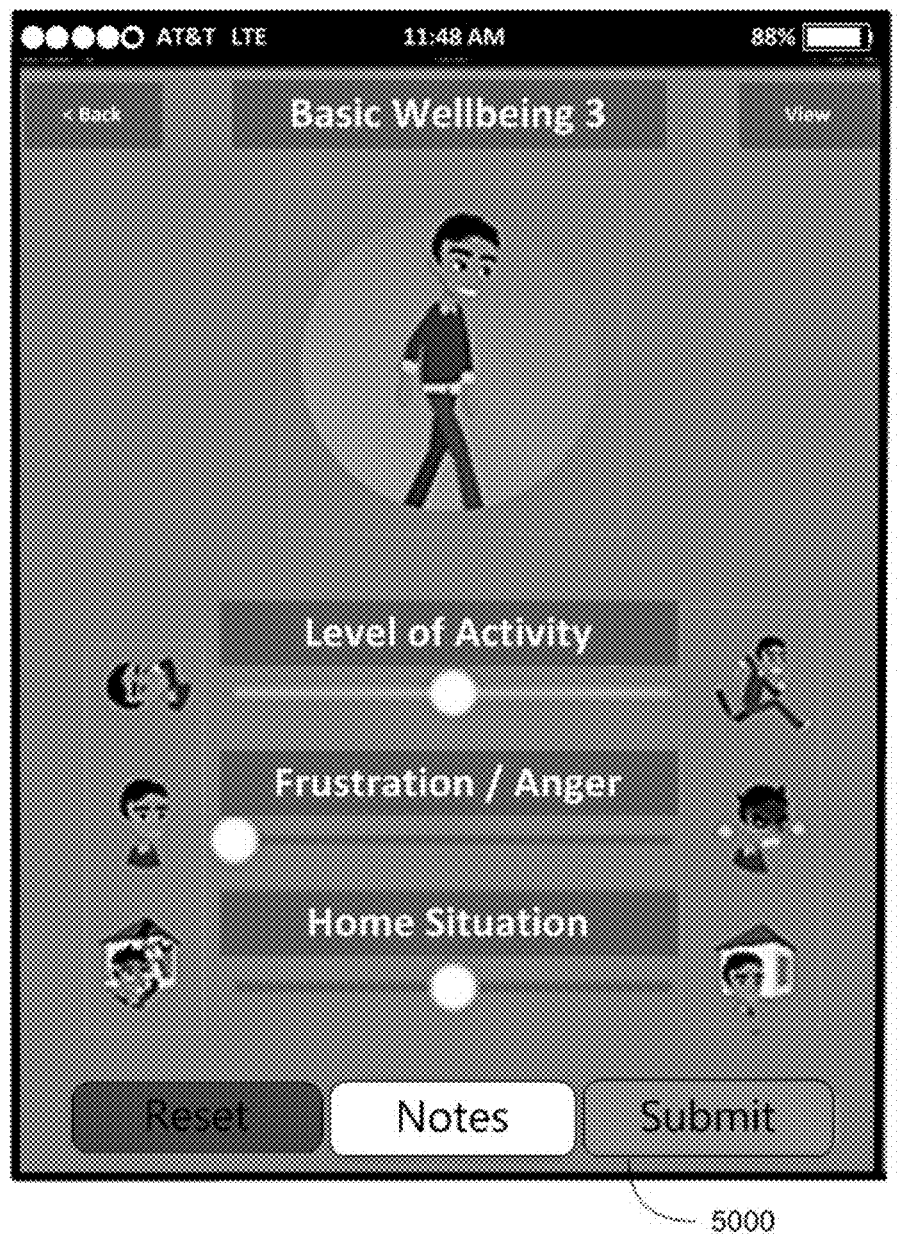
FIGS. 51-52 each illustrates the user interface of FIG. 50 in which user input regarding a level of activity is being received by sliding the slider control for "Level of Activity" to a new position as illustrated therein.

FIG. 51 illustrates the same user interface 5000 in which user input regarding a level of activity is being received by sliding the slider control for "Level of Activity" to a new position as illustrated therein.

Figure 52:
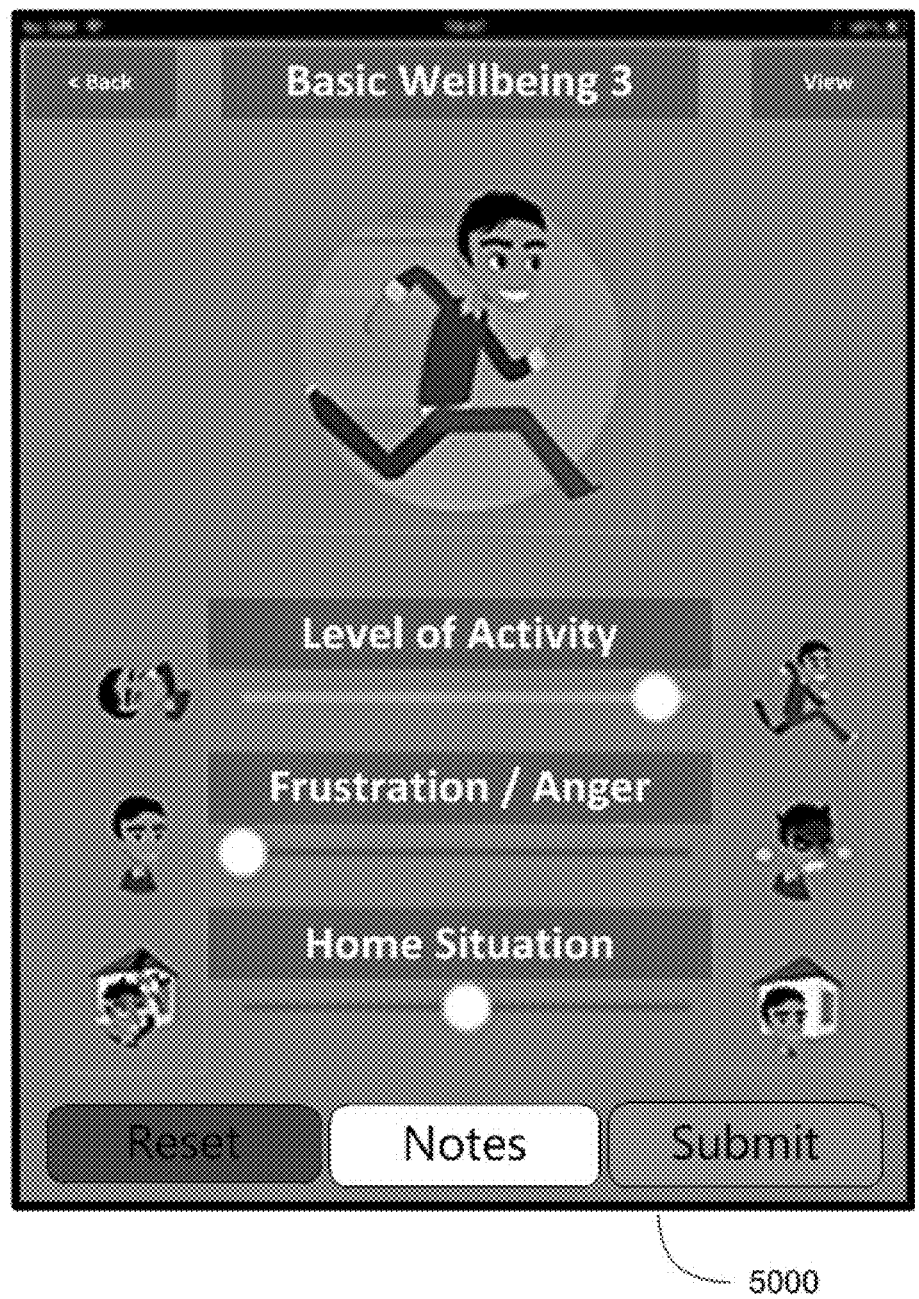

FIG. 52 illustrates the same user interface 5000 in which user input regarding a level of activity is being received by sliding the slider control for "Level of Activity" to a position as illustrated therein.

Figure 53:
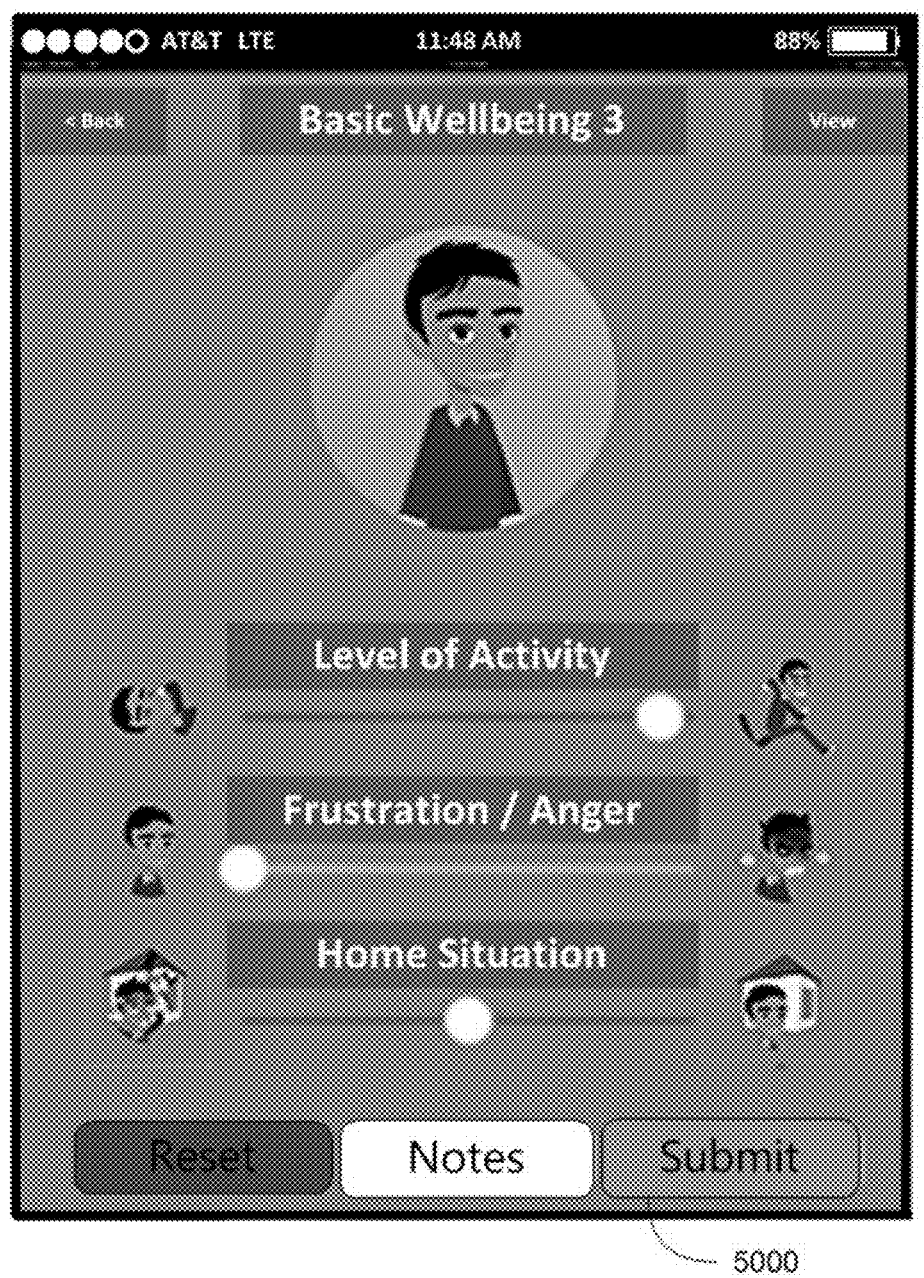
FIG. 53 illustrates the user interface of FIG. 50 in which user input regarding a degree of frustration or anger is being received by sliding the slider control for "Frustration/Anger" to a position as illustrated therein.

FIG. 53 illustrates the same user interface 5000 in which user input regarding a degree of frustration or anger is being received by sliding the slider control for "Frustration/Anger" to a position as illustrated therein.

Figure 54:
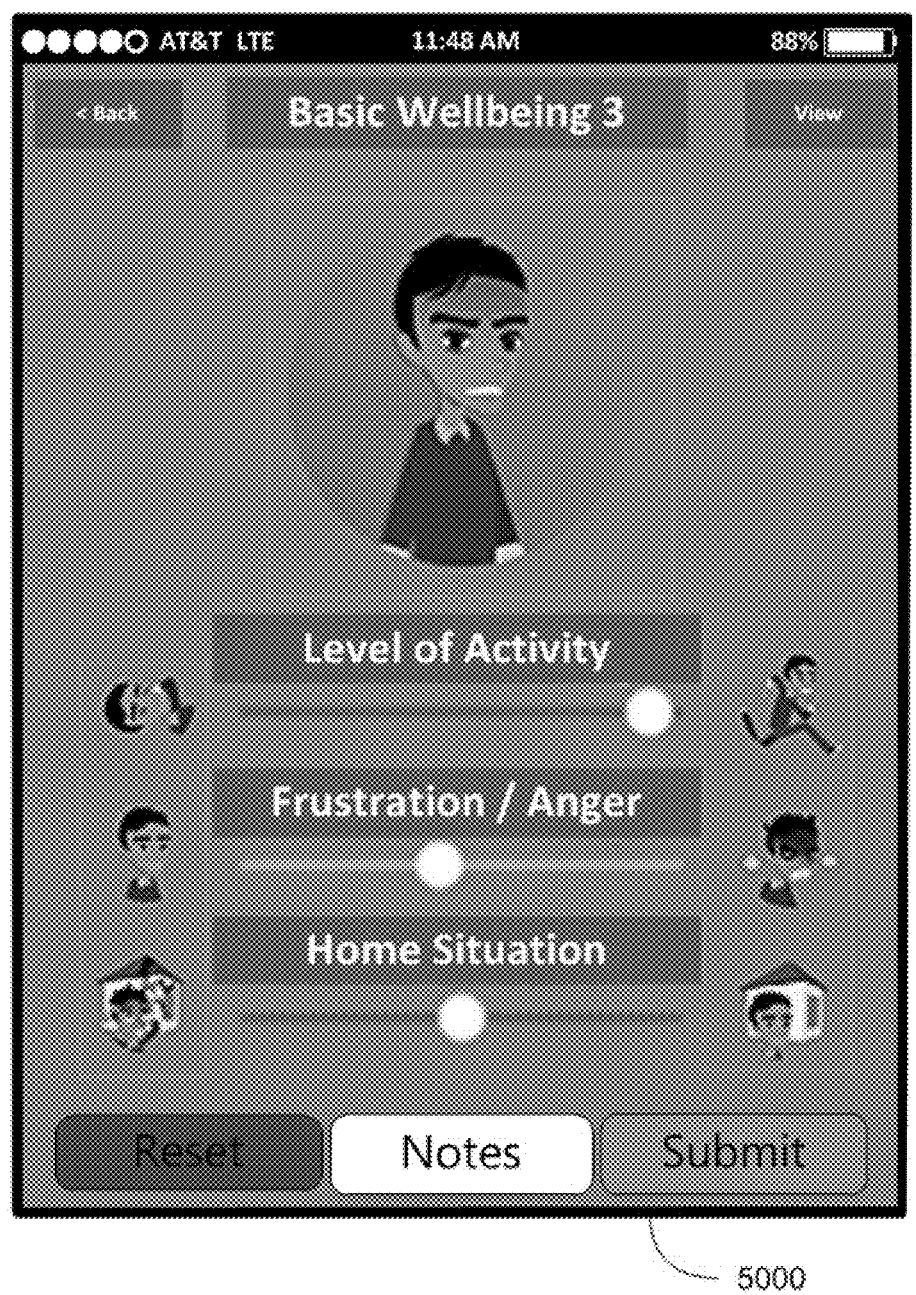
FIGS. 54-55 each illustrates the user interface of FIG. 53 in which user input regarding a degree of frustration or anger is being received by sliding the slider control for "Frustration/Anger" to a new position as illustrated therein.

FIG. 54 illustrates the same user interface 5000 in which user input regarding a degree of frustration or anger is being received by sliding the slider control for "Frustration/Anger" to a new position as illustrated therein.

Figure 55:
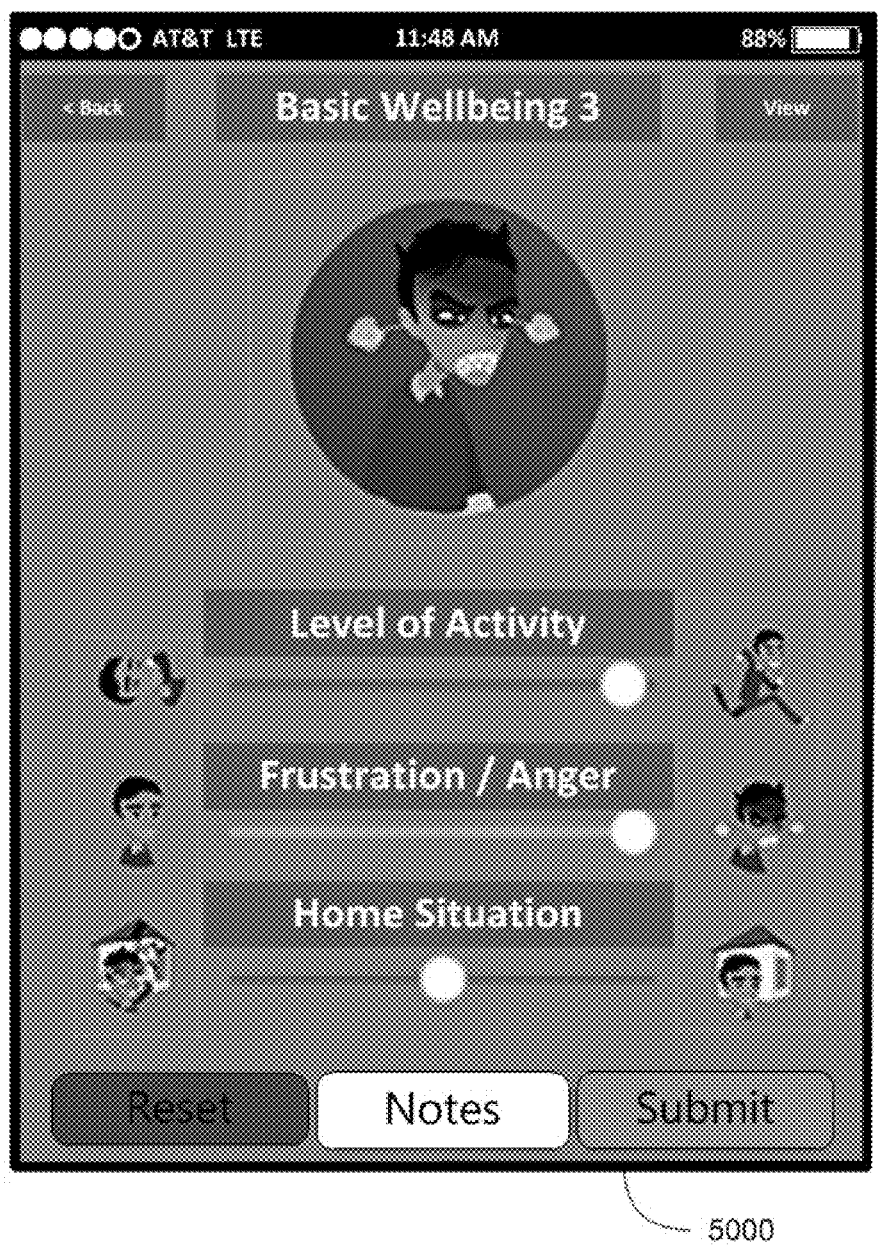

FIG. 55 illustrates the same user interface 5000 in which user input regarding a degree of frustration or anger is being received by sliding the slider control for "Frustration/Anger" to a position as illustrated therein.

Figure 56:
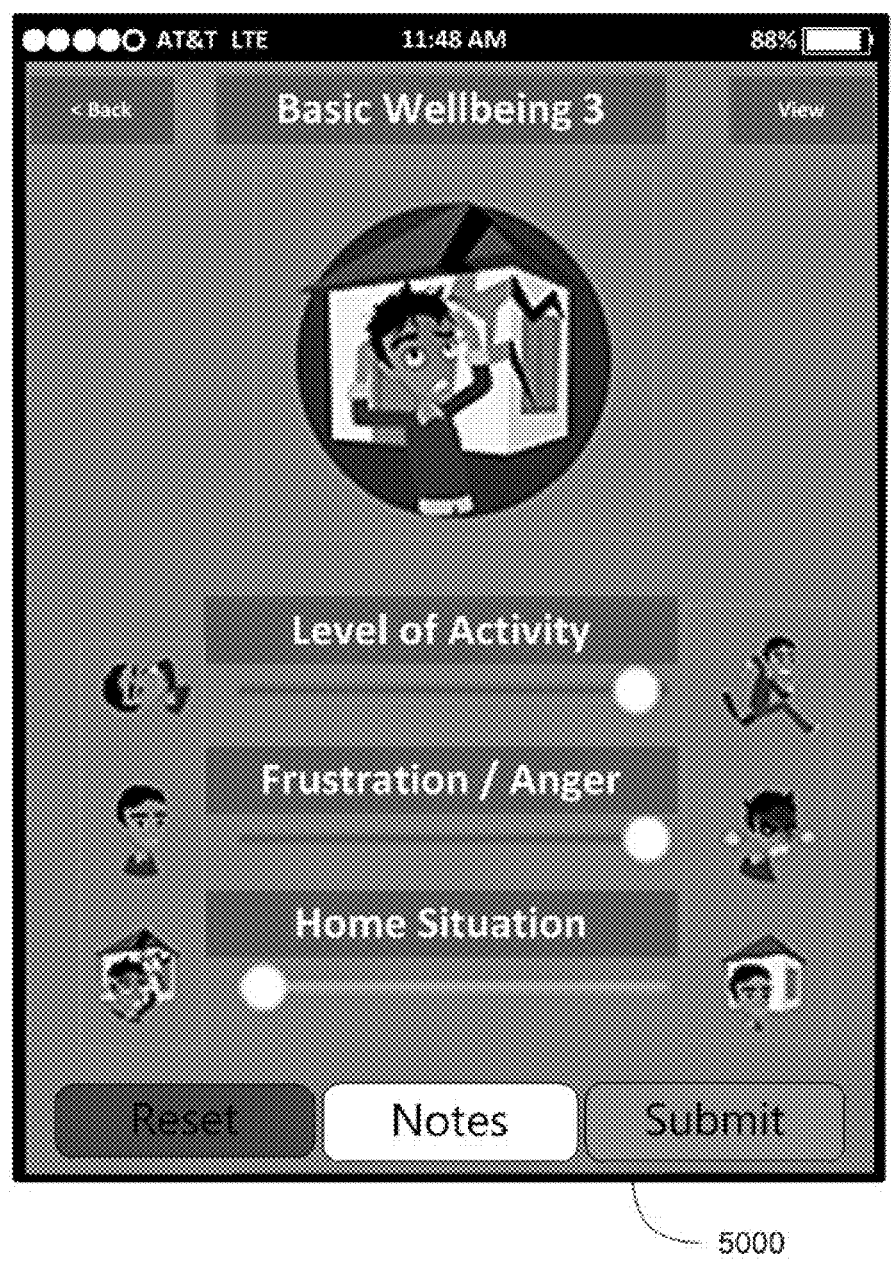
FIG. 56 illustrates the user interface of FIG. 50 in which user input regarding a user's home situation is being received by sliding the slider control for "Home Situation" to a position as illustrated therein.

FIG. 56 illustrates the same user interface 5000 in which user input regarding a user's home situation is being received by sliding the slider control for "Home Situation" to a position as illustrated therein.

Figure 57:
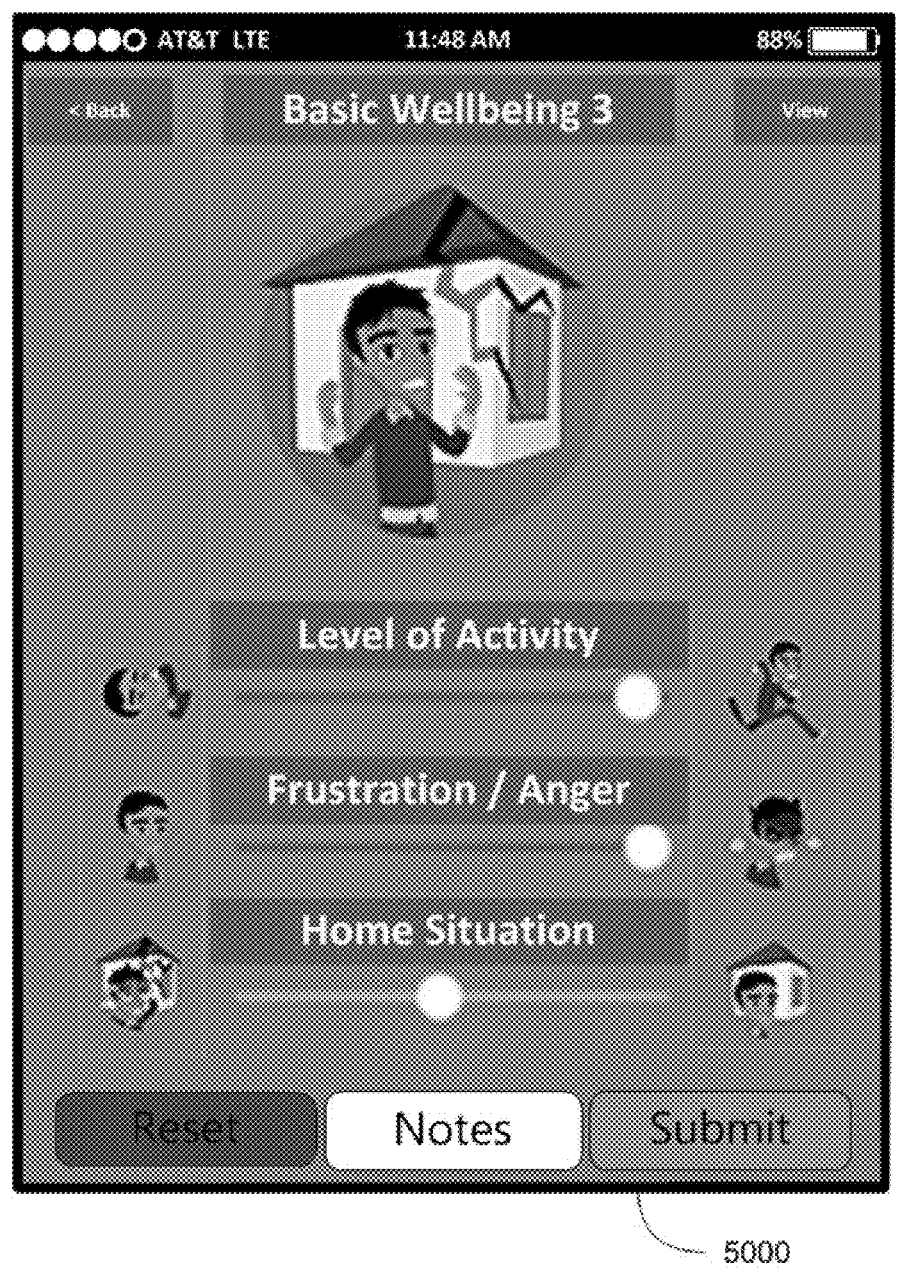
FIGS. 57-58 each illustrates the user interface of FIG. 56 in which user input regarding a user's home situation is being received by sliding the slider control for "Home Situation" to a new position as illustrated therein.

FIG. 57 illustrates the same user interface 5000 in which user input regarding a user's home situation is being received by sliding the slider control for "Home Situation" to a new position as illustrated therein.

Figure 58:

FIG. 58 illustrates the same user interface 5000 in which user input regarding a user's home situation is being received by sliding the slider control for "Home Situation" to a position as illustrated therein.

Figure 59:
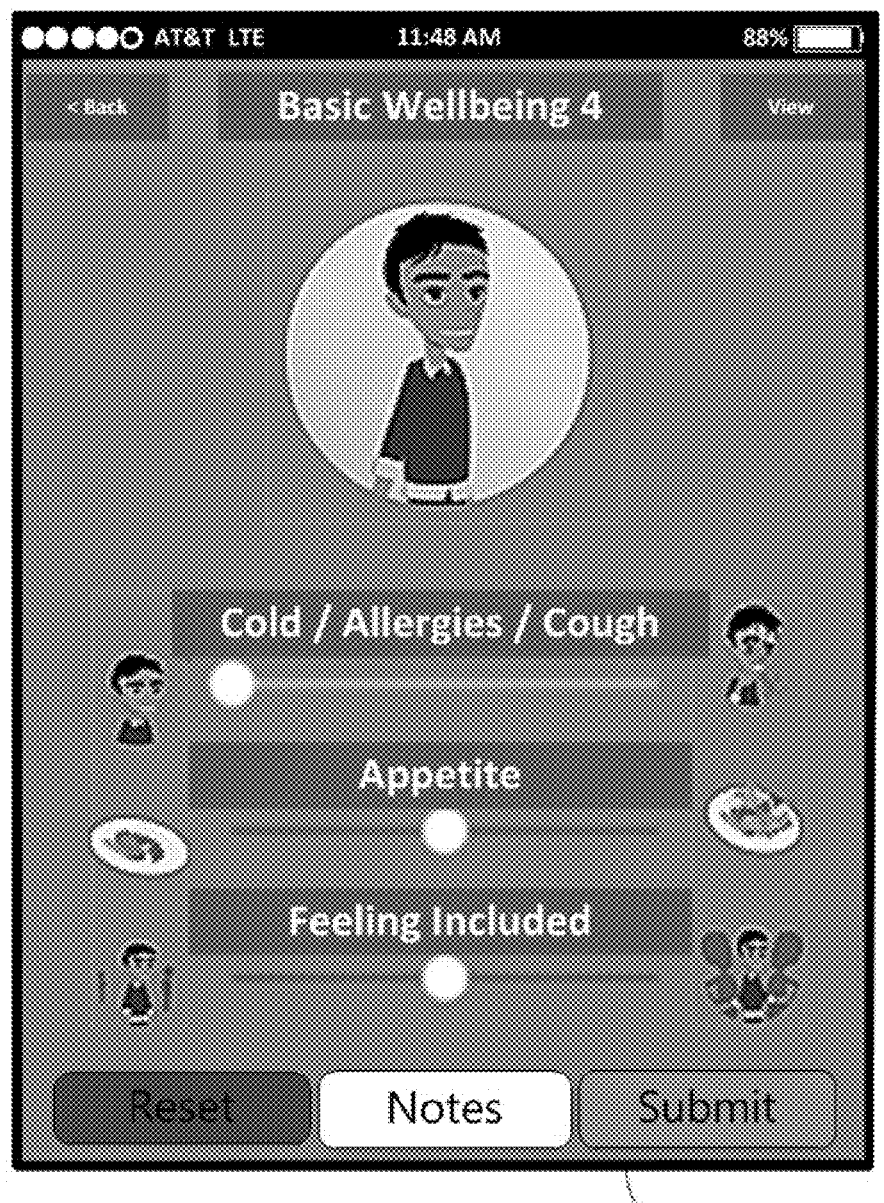
FIG. 59 illustrates a user interface 5900 in which user input regarding a user's cold, allergies, or cough is being received by sliding the slider control for "Cold/Allergies/Cough" to a position as illustrated therein.

FIG. 59 illustrates a user interface 5900 in which user input regarding a user's cold, allergies, or cough is being received by sliding the slider control for "Cold/Allergies/Cough" to a position as illustrated therein.

Figure 60:
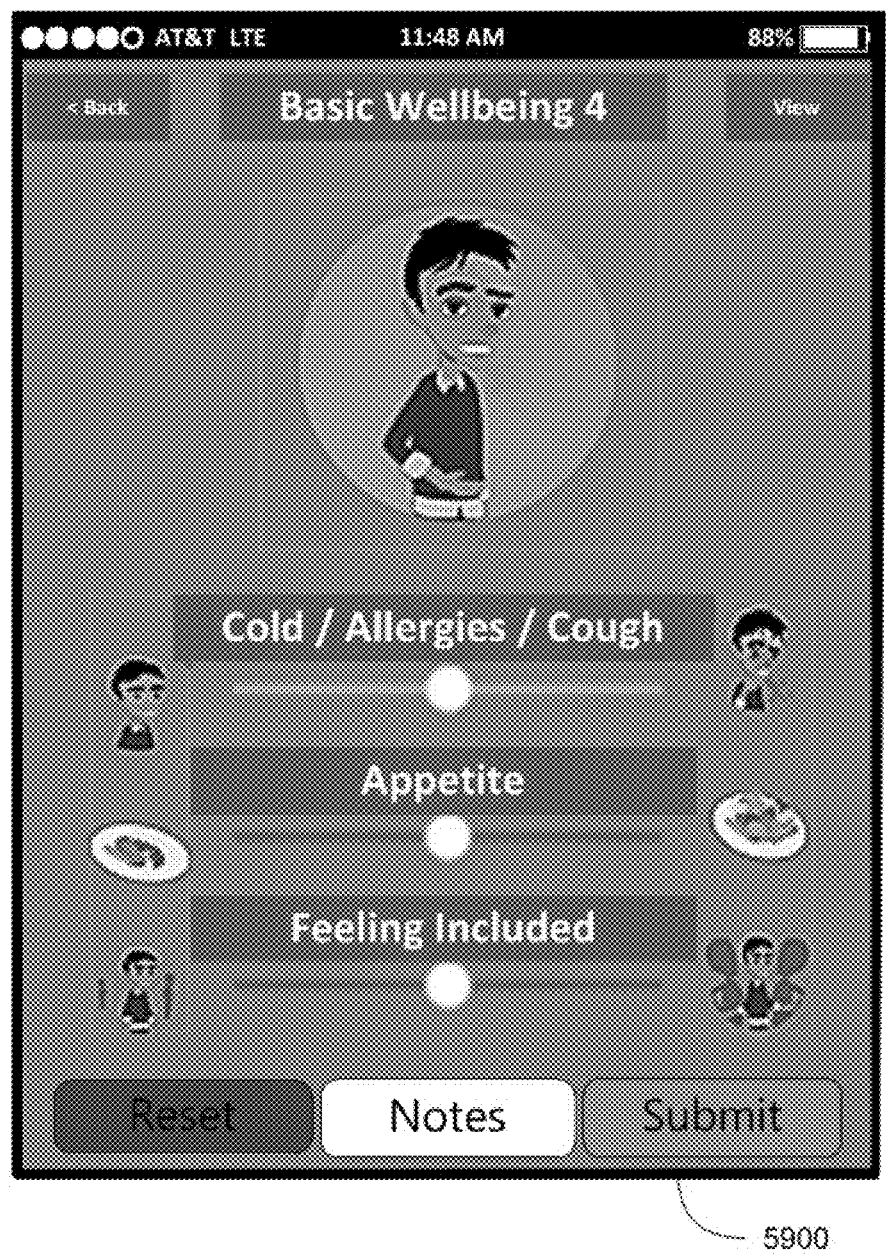
FIGS. 60-61 each illustrates the user interface of FIG. 59 in which user input regarding a user's cold, allergies, or cough is being received by sliding the slider control for "Cold/Allergies/Cough" to a new position as illustrated therein.

FIG. 60 illustrates the same user interface 5900 in which user input regarding a user's cold, allergies, or cough is being received by sliding the slider control for "Cold/Allergies/Cough" to a new position as illustrated therein.

Figure 61:
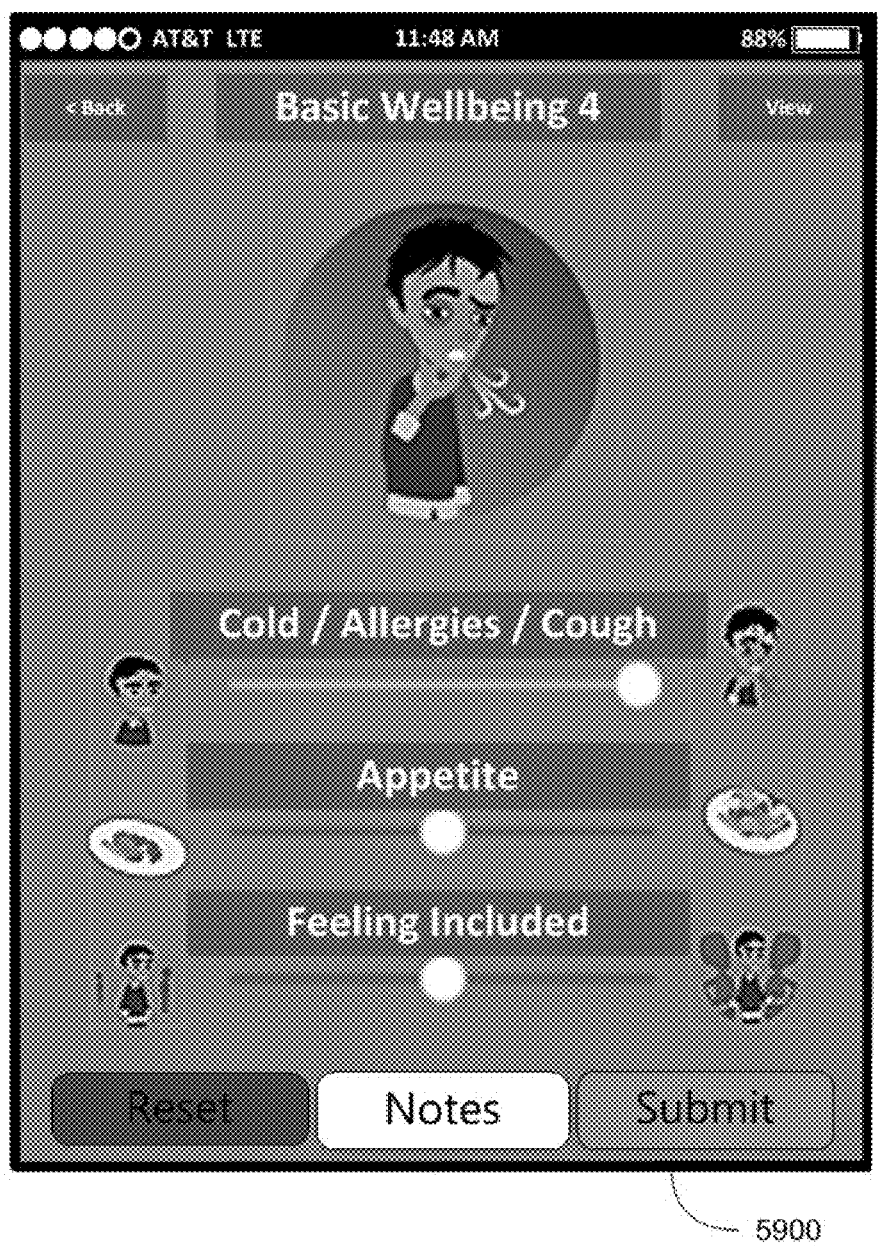

FIG. 61 illustrates the same user interface 5900 in which user input regarding a user's cold, allergies, or cough is being received by sliding the slider control for "Cold/Allergies/Cough" to a new position as illustrated therein.

Figure 62:
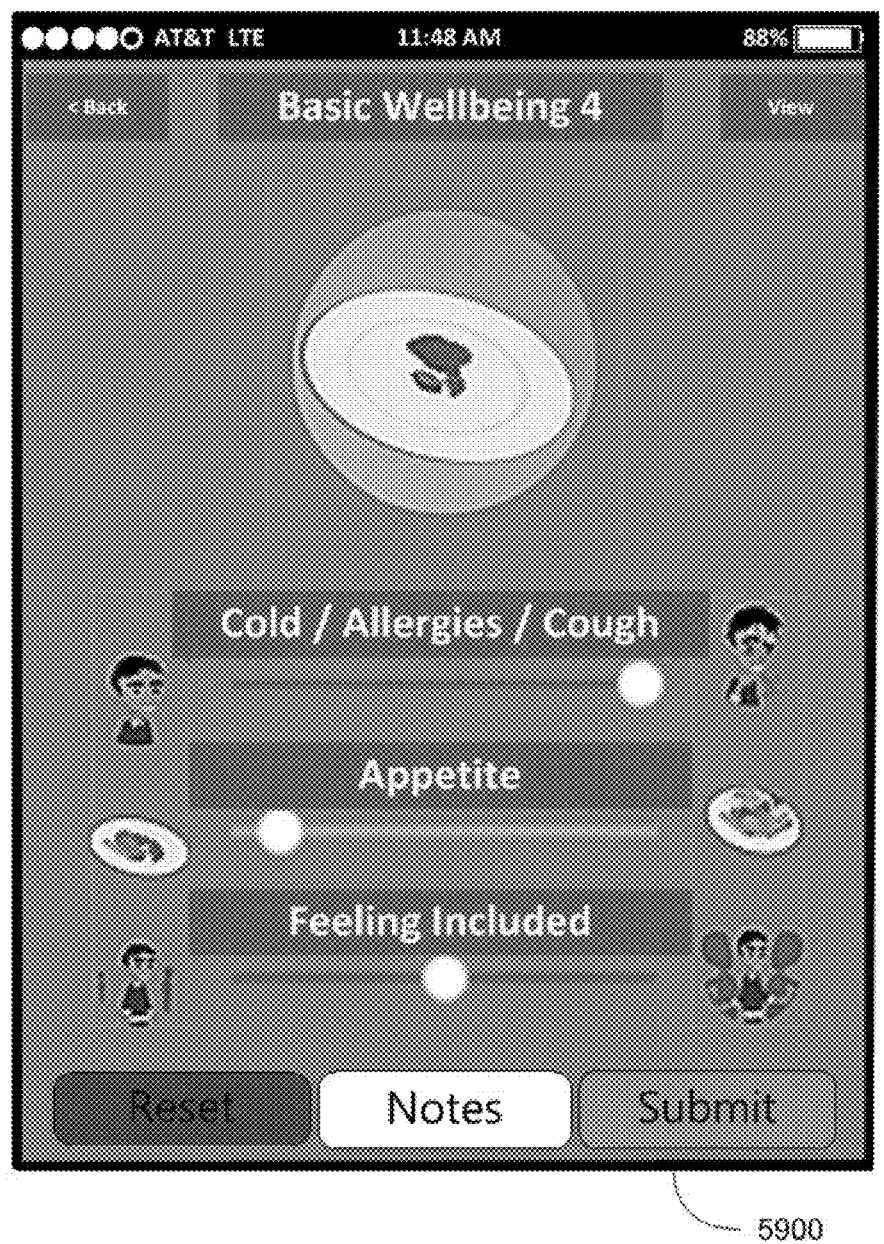
FIG. 62 illustrates the user interface of FIG. 59 in which user input regarding a level of a user's appetite is being received by sliding the slider control for "Appetite" to a position as illustrated therein.

FIG. 62 illustrates the same user interface 5900 in which user input regarding a level of a user's appetite is being received by sliding the slider control for "Appetite" to a position as illustrated therein.

Figure 63:
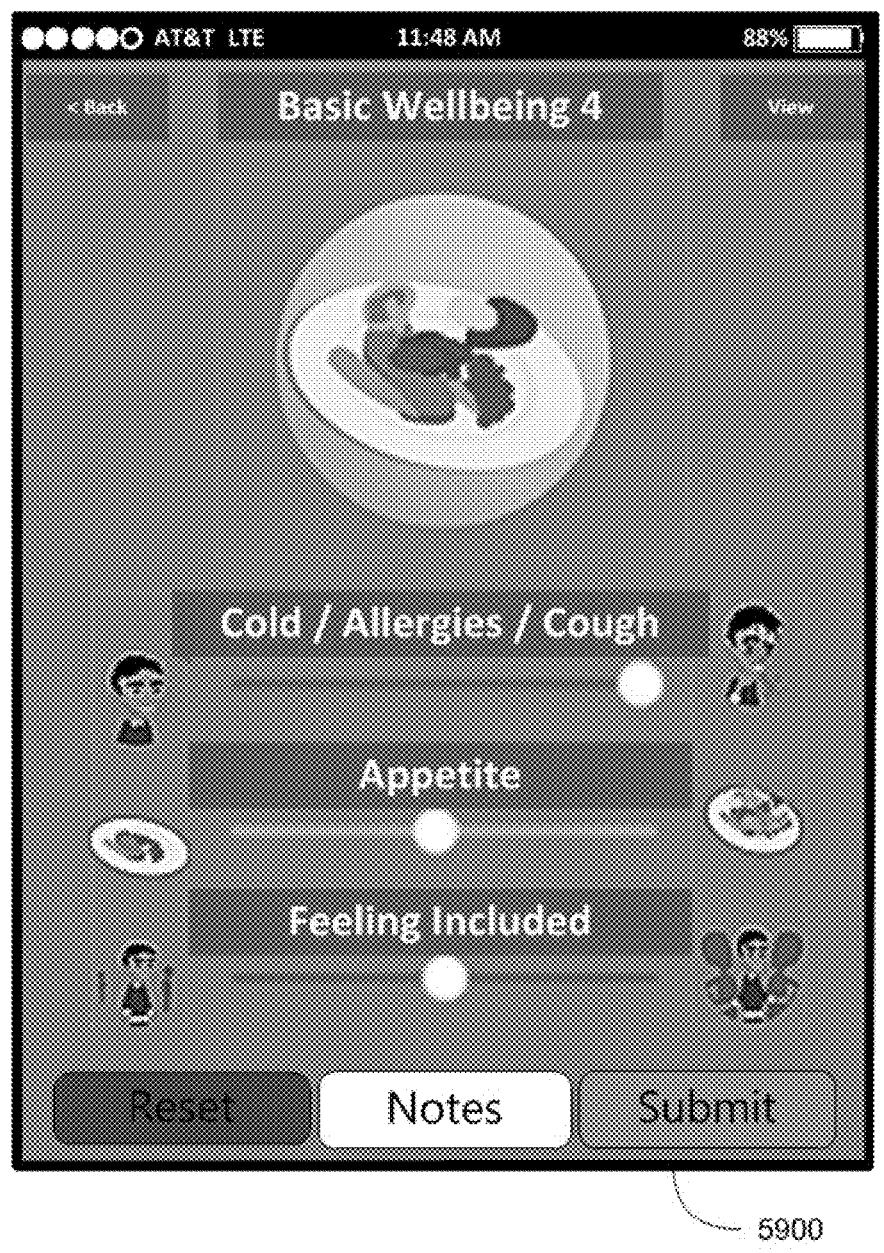
FIGS. 63-64 each illustrates the user interface of FIG. 62 in which user input regarding a level of a user's appetite is being received by sliding the slider control for "Appetite" to a new position as illustrated therein.

FIG. 63 illustrates the same user interface 5900 in which user input regarding a level of a user's appetite is being received by sliding the slider control for "Appetite" to a new position as illustrated therein.

Figure 64:
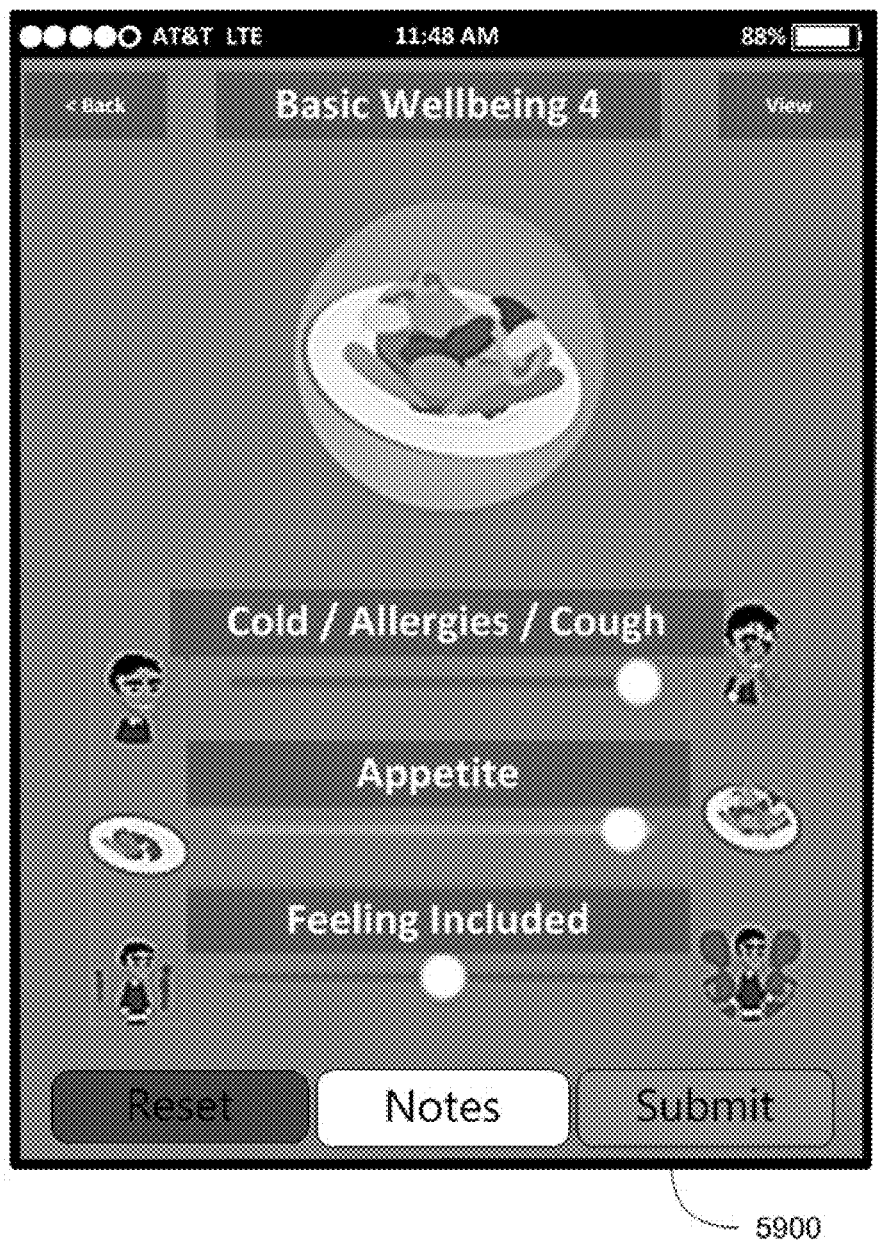

FIG. 64 illustrates the same user interface 5900 in which user input regarding a level of a user's appetite is being received by sliding the slider control for "Appetite" to a position as illustrated therein.

Figure 65:
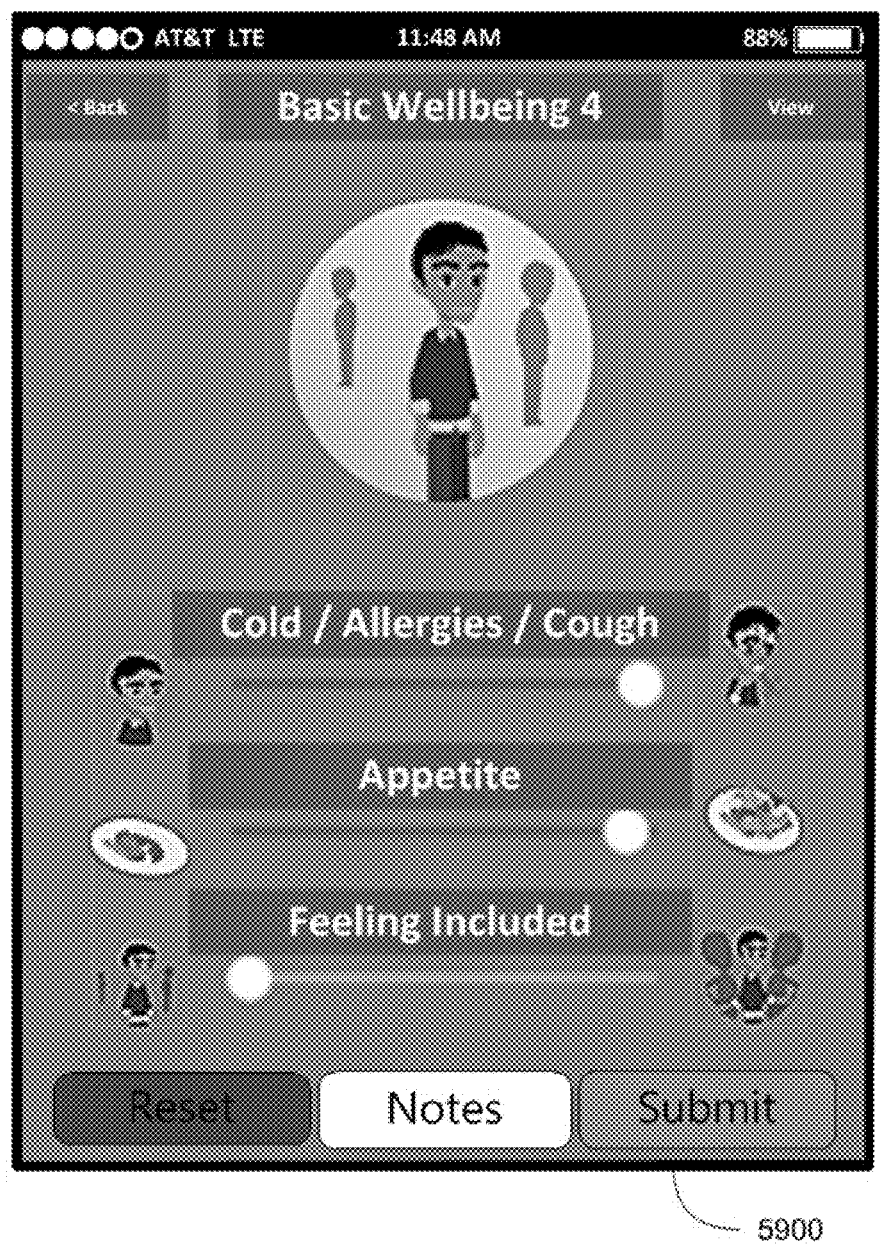
FIG. 65 illustrates the user interface of FIG. 59 in which user input regarding a user's feeling of inclusion is being received by sliding the slider control for "Feeling Included" to a position as illustrated therein.

FIG. 65 illustrates the same user interface 5900 in which user input regarding a user's feeling of inclusion is being received by sliding the slider control for "Feeling Included" to a position as illustrated therein.

Figure 66:
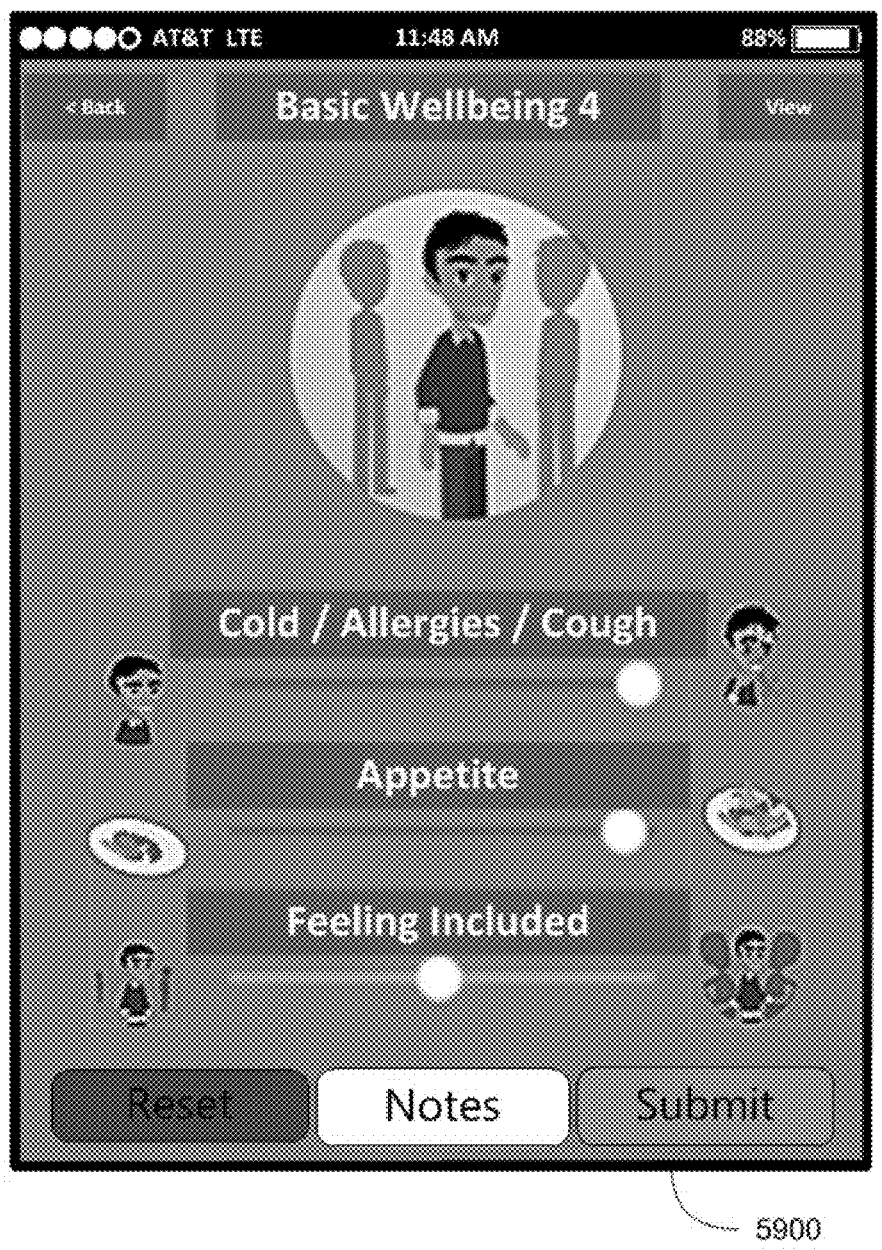
FIGS. 66-67 each illustrates the same user interface of FIG. 65 in which user input regarding a user's feeling of inclusion is being received by sliding the slider control for "Feeling Included" to a new position as illustrated therein.

FIG. 66 illustrates the same user interface 5900 in which user input regarding a user's feeling of inclusion is being received by sliding the slider control for "Feeling Included" to a new position as illustrated therein.

Figure 67:
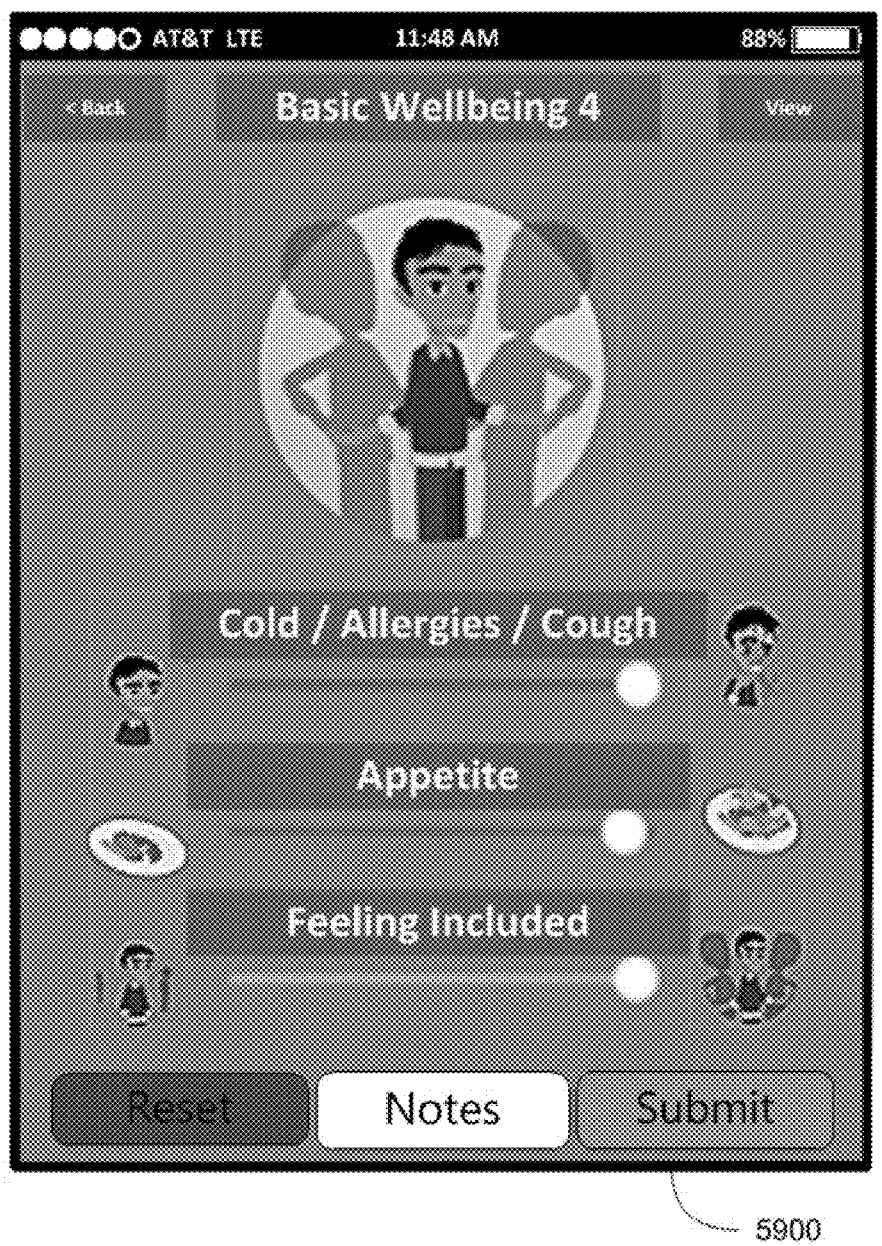

FIG. 67 illustrates the same user interface 5900 in which user input regarding a user's feeling of inclusion is being received by sliding the slider control for "Feeling Included" to a position as illustrated therein.

Figure 68:
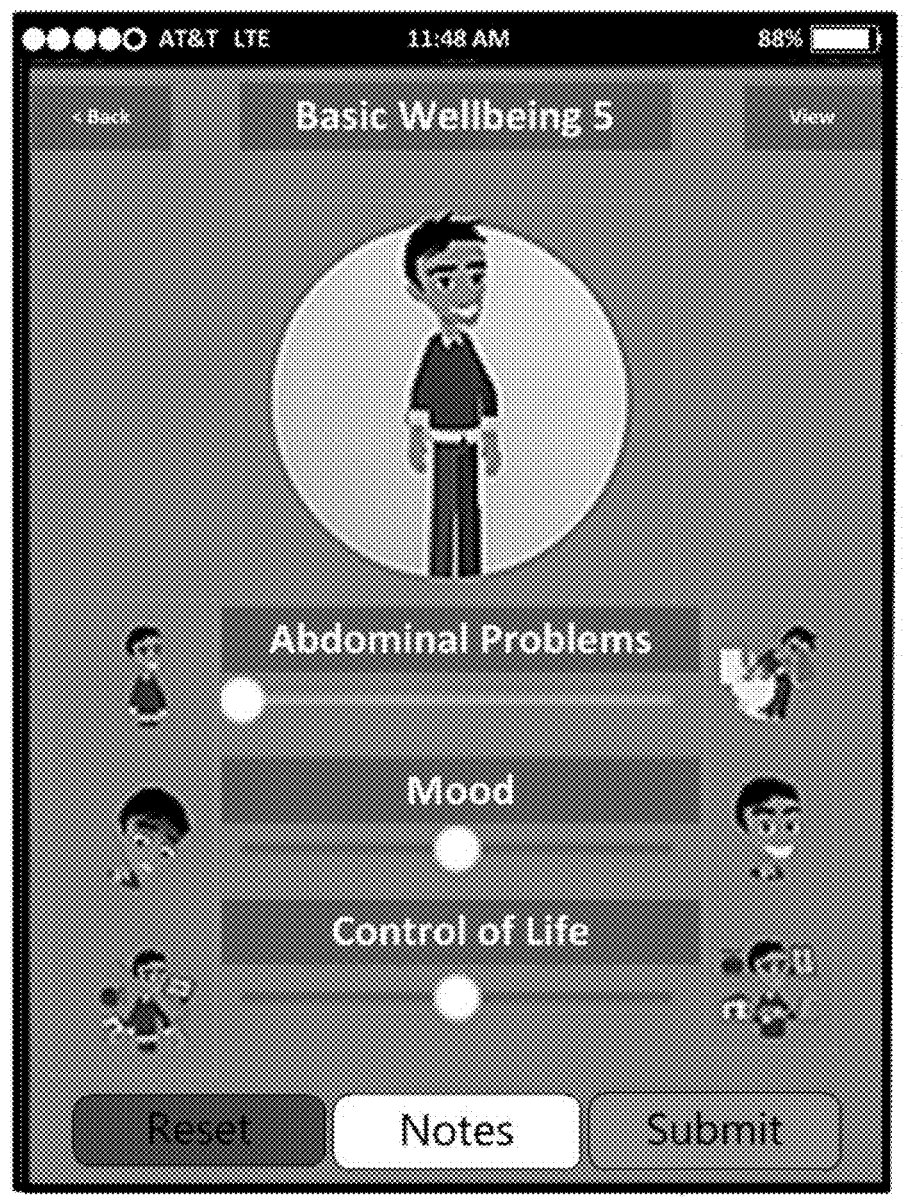
FIG. 68 illustrates a user interface in which user input regarding a degree of abdominal problems is being received by sliding the slider control for "Abdominal Problems" to a position as illustrated therein.

FIG. 68 illustrates a user interface 6800 in which user input regarding a degree of abdominal problems is being received by sliding the slider control for "Abdominal Problems" to a position as illustrated therein.

Figure 69:
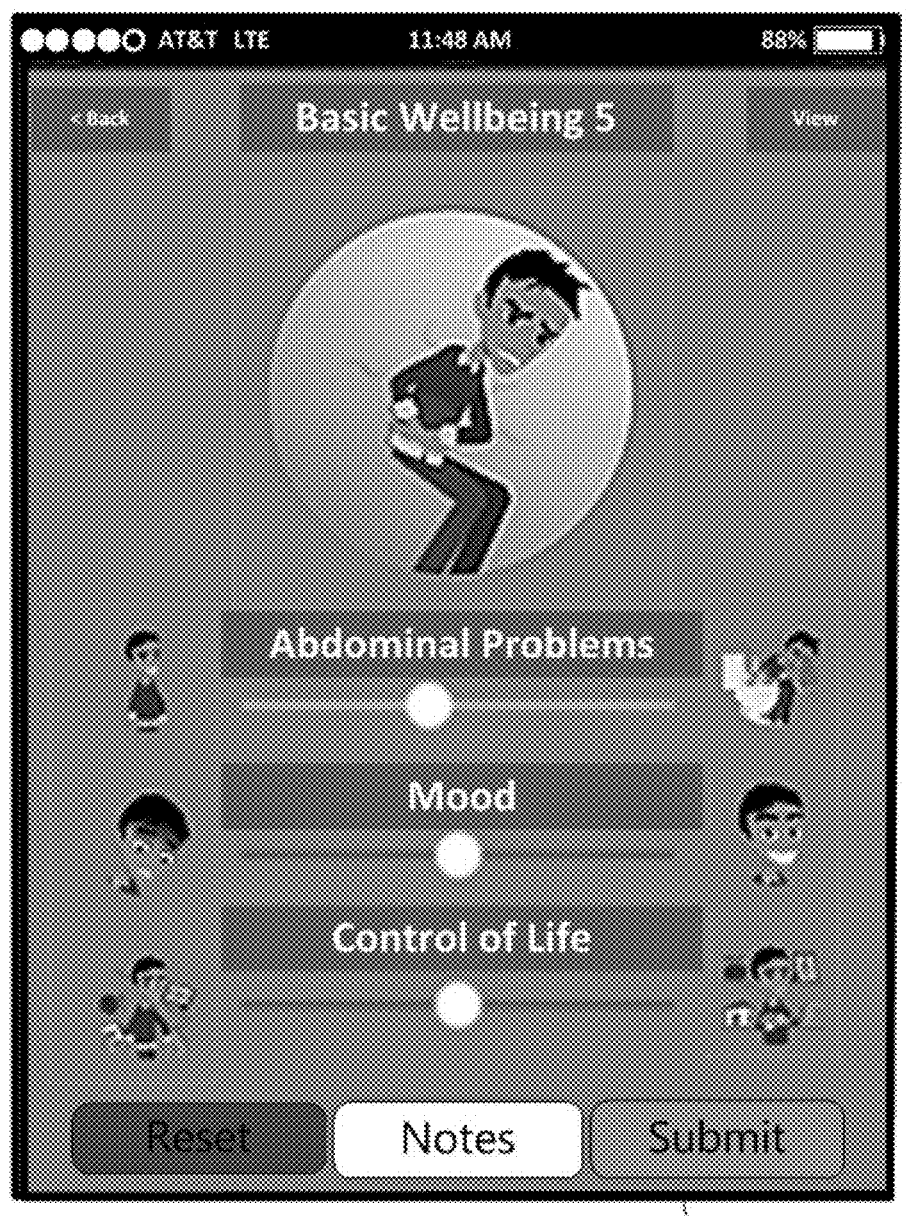
FIGS. 69-70 each illustrates the user interface of FIG. 68 in which user input regarding a degree of abdominal problems is being received by sliding the slider control for "Abdominal Problems" to a new position as illustrated therein.

FIG. 69 illustrates the same user interface 6800 in which user input a degree of abdominal problems is being received by sliding the slider control for "Abdominal Problems" to a new position as illustrated therein.

Figure 70:
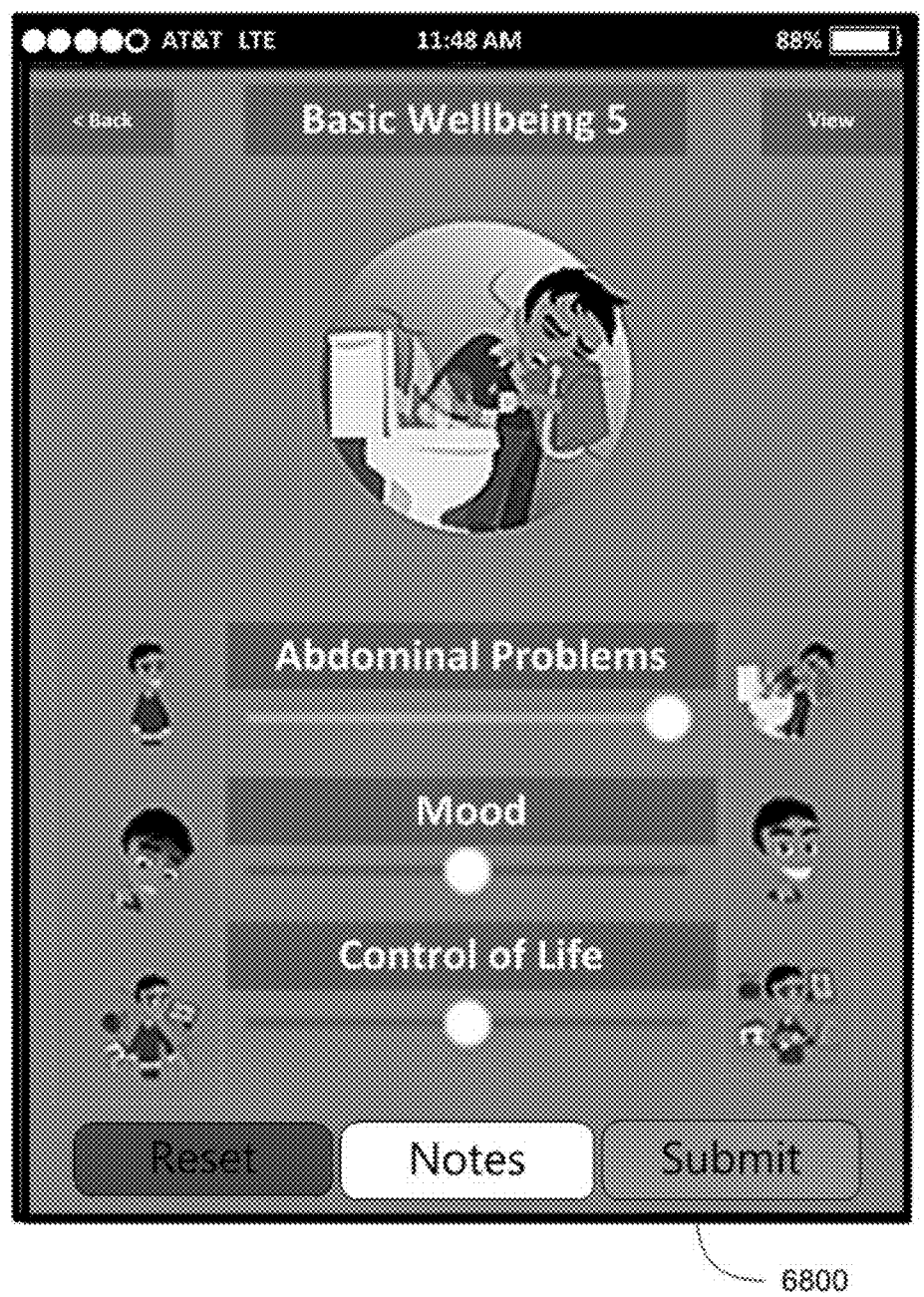

FIG. 70 illustrates the same user interface 6800 in which user input regarding a degree of abdominal problems is being received by sliding the slider control for "Abdominal Problems" to a position as illustrated therein.

Figure 71:
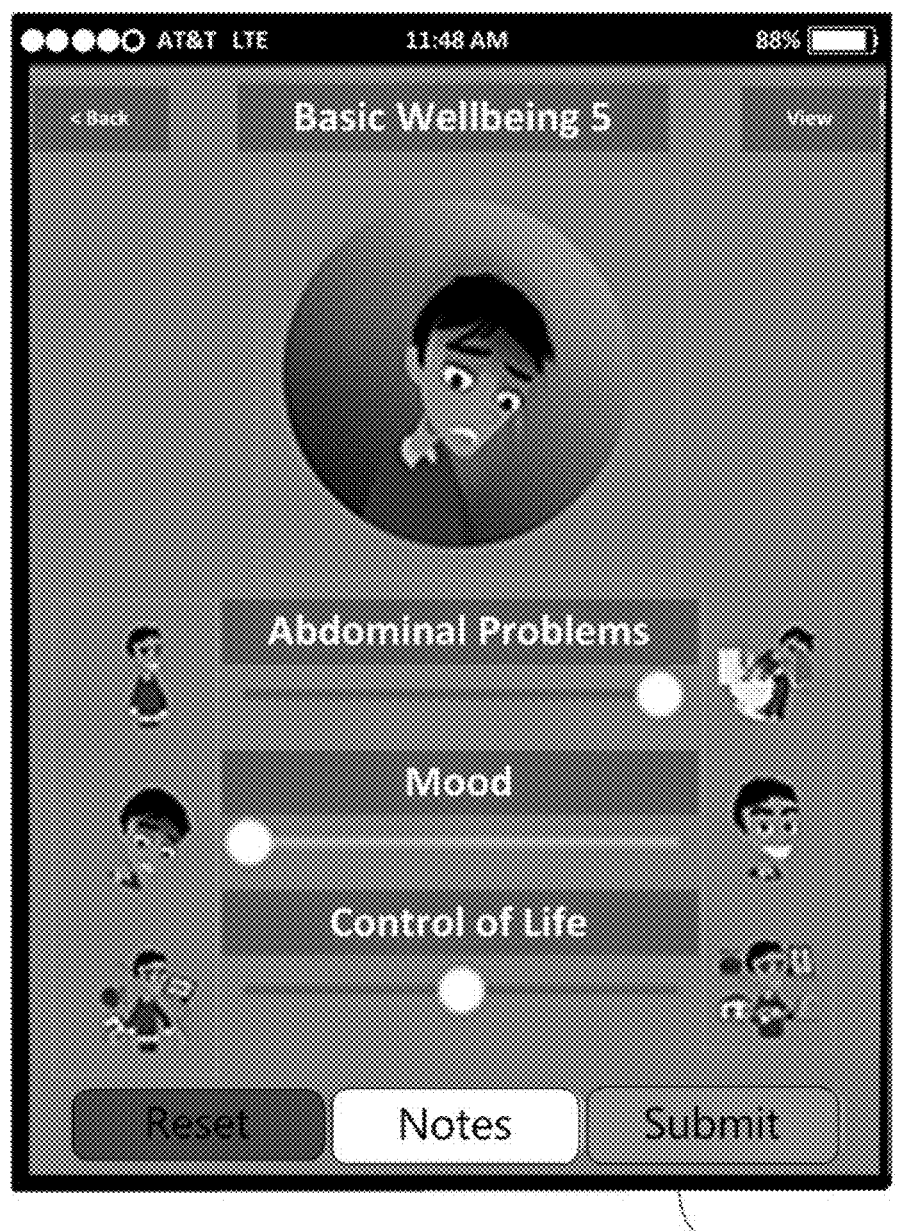
FIG. 71 illustrates the user interface of FIG. 68 in which user input regarding a user's mood is being received by sliding the slider control for "Mood" to a position as illustrated therein.

FIG. 71 illustrates the same user interface 6800 in which user input regarding a user's mood is being received by sliding the slider control for "Mood" to a position as illustrated therein.

Figure 72:
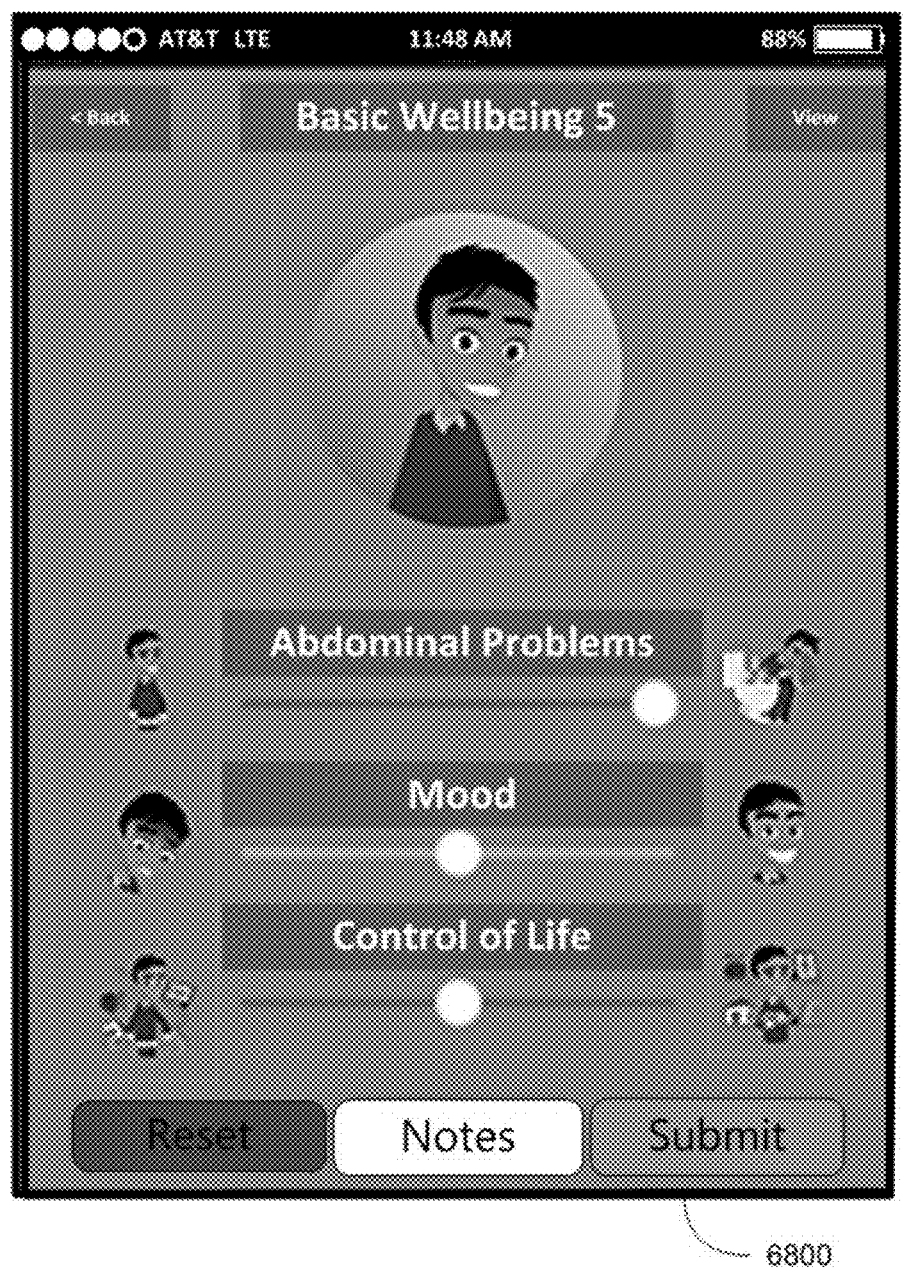
FIG. 72-73 each illustrates the user interface of FIG. 71 in which user input regarding a user's mood is being received by sliding the slider control for "Mood" to a new position as illustrated therein.

FIG. 72 illustrates the same user interface 6800 in which user input regarding a user's mood is being received by sliding the slider control for "Mood" to a new position as illustrated therein.

Figure 73:
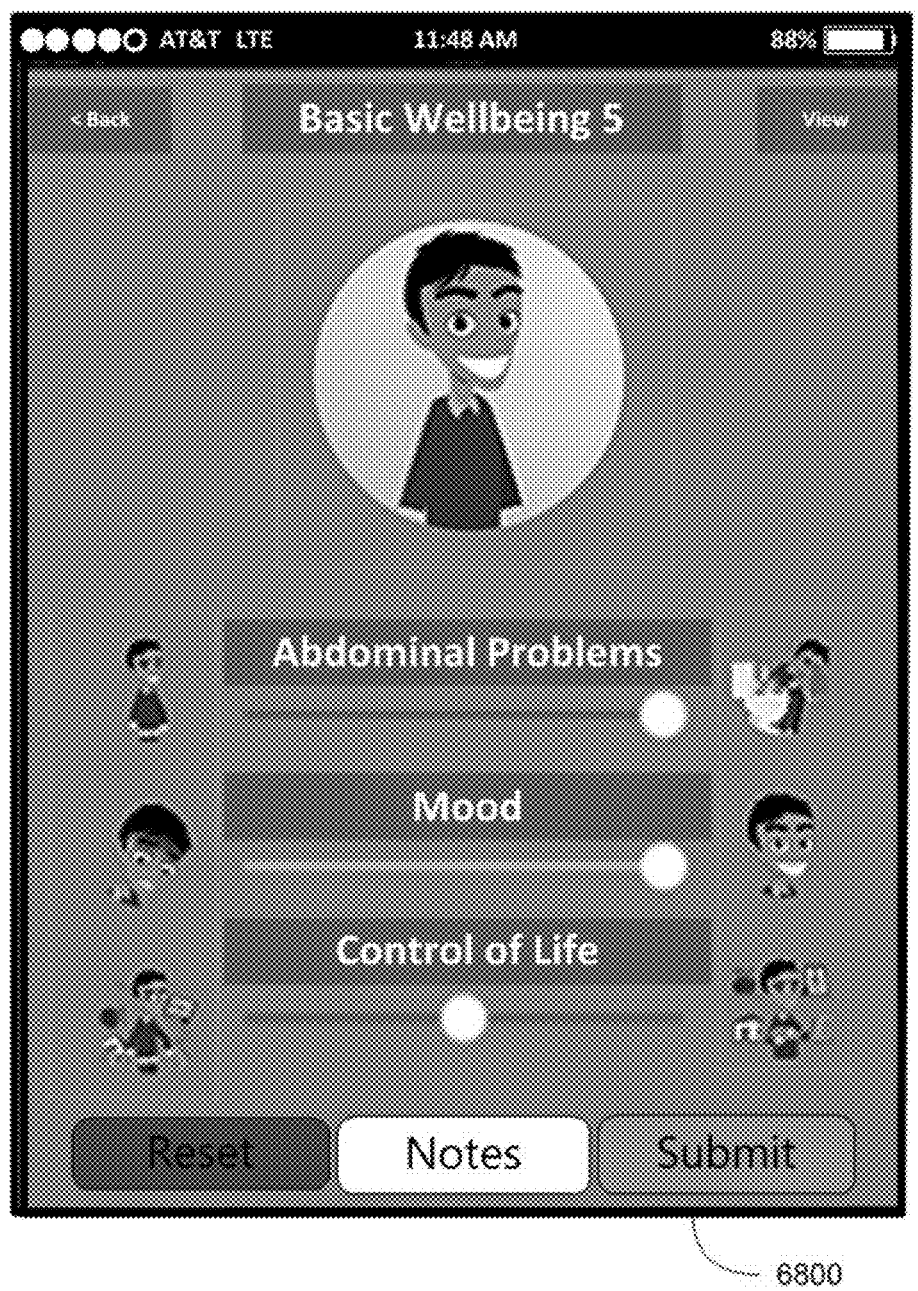

FIG. 73 illustrates the same user interface 6800 in which user input regarding a user's mood is being received by sliding the slider control for "Mood" to a position as illustrated therein.

Figure 74:
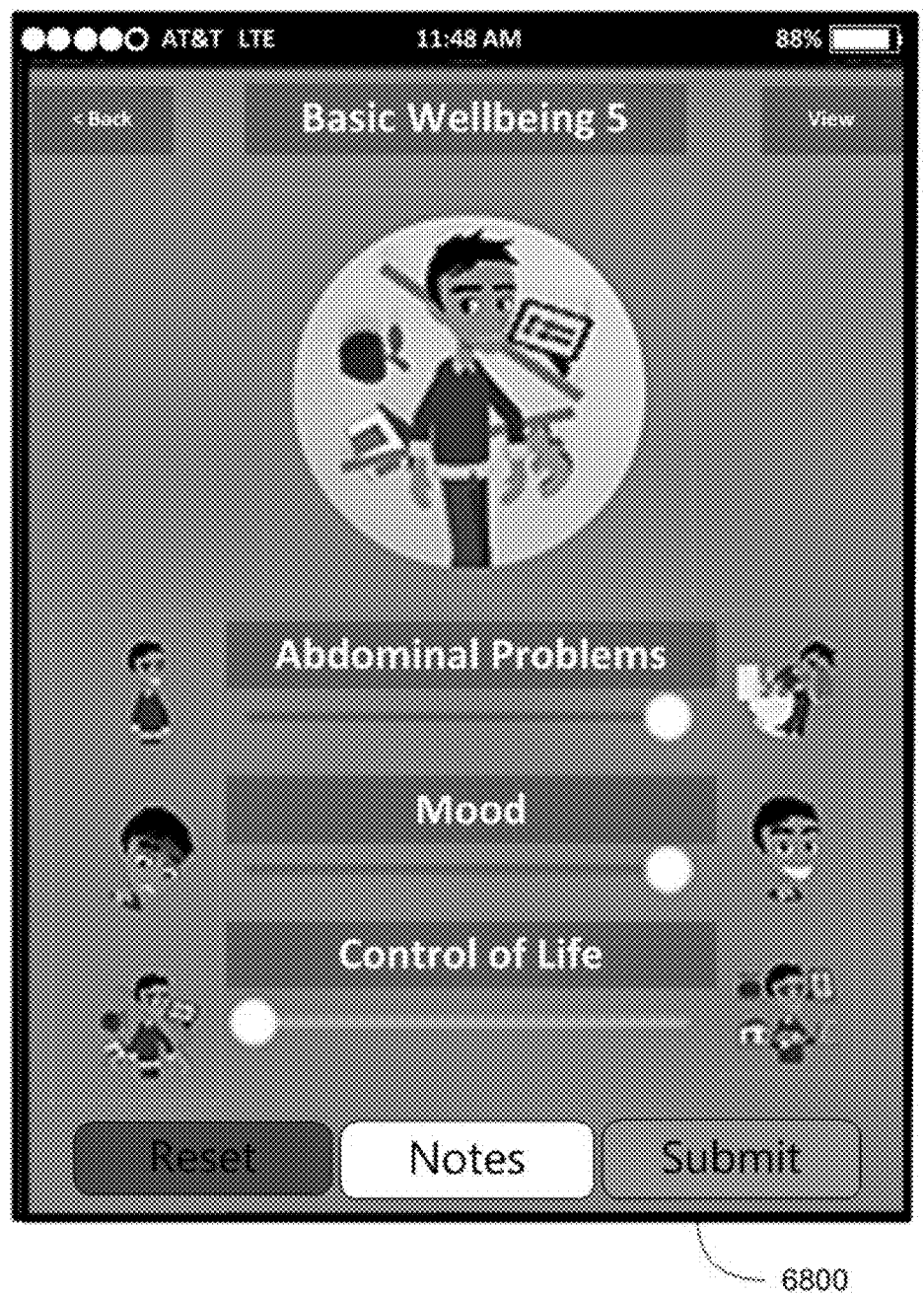
FIG. 74 illustrates the user interface of FIG. 68 in which user input regarding a user feeling of control of life at home is being received by sliding the slider control for "Control of Life" to a position as illustrated therein.

FIG. 74 illustrates the same user interface 6800 in which user input regarding a user feeling of control of life home is being received by sliding the slider control for "Control of Life" to a position as illustrated therein.

Figure 75:
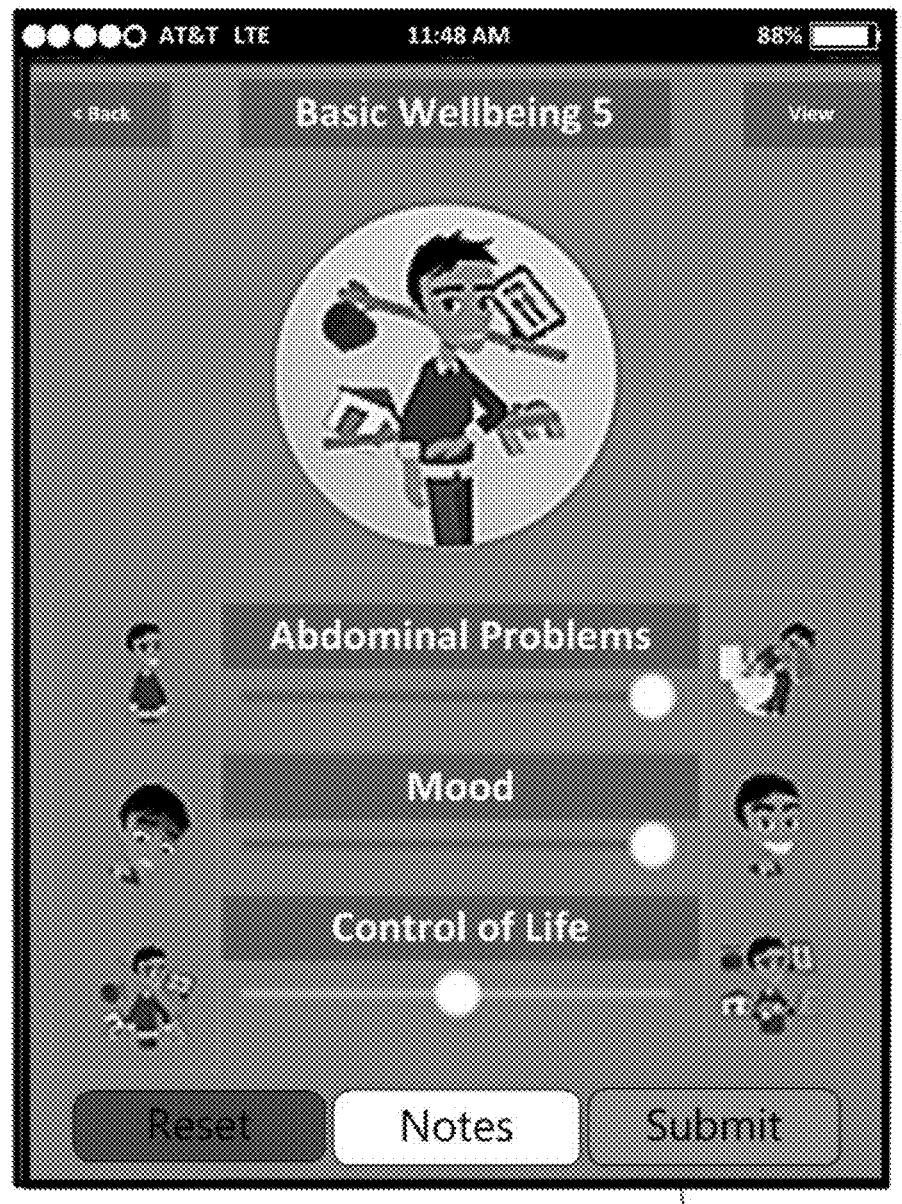
FIGS. 75-76 each illustrates the user interface of FIG. 68 in which user input regarding a user feeling of control of life home is being received by sliding the slider control for "Control of Life" to a new position as illustrated therein.

FIG. 75 illustrates the same user interface 6800 in which user input regarding a user feeling of control of life home is being received by sliding the slider control for "Control of Life" to a new position as illustrated therein.

Figure 76:
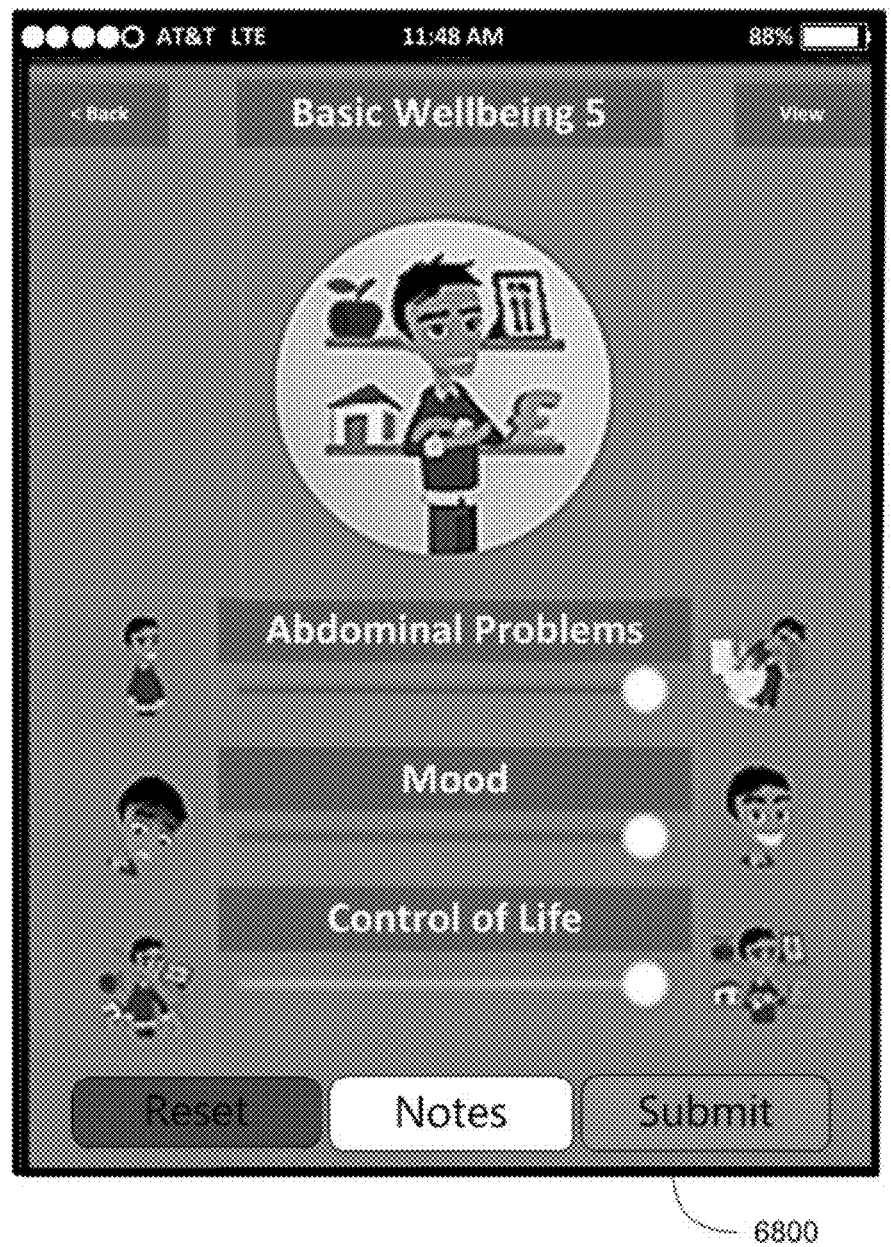

FIG. 76 illustrates the same user interface 6800 in which user input a user feeling of control of life home is being received by sliding the slider control for "Control of Life" to a position as illustrated therein.

Figure 77:
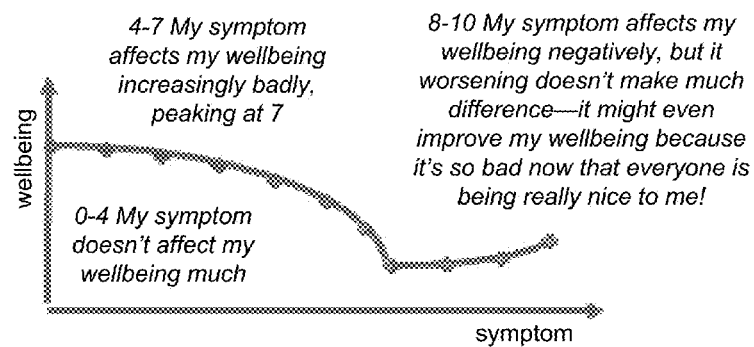
FIG. 77 demonstrates an exemplary shape of how wellbeing may change as severity of a symptom increases.
Figure 78:
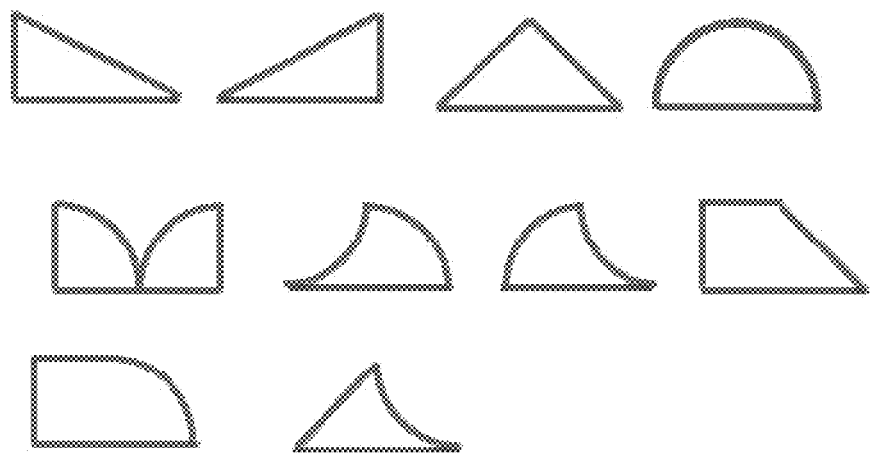
FIG. 78 schematically illustrates an additional ten shapes any of which that may apply in graphically illustrating how wellbeing may change as severity of a symptom increases.

FIG. 77 demonstrates an exemplary shape of how wellbeing may change as severity of a symptom increases. FIG. 78 schematically illustrates additional shapes that may be applicable. A particular shape can be determined after a large number of surveys has been conducted for different severities of a symptom versus wellbeing of such persons, and the shape can continue to be adjusted as more survey data is collected.

Moreover, while "Overall Wellbeing" is the target metric in the graph of FIG. 77, an important secondary health outcome instead could be graphed as the target metric, such as hospital admission, depending on the reason for the analysis. Therefore, the outcome could either be one metric, as defined by the user's "Overall Wellbeing", or more likely, a combination of metrics that may relate to, for example, "Quality of Life" or "Overall Cost". Part of the analysis will involve extracting the factors that affect the metric most, and in which concentrations.

It will be appreciated that a database can be constructed to contain a sentiment ($s\_q$), where sentiment can be good, bad or a shape as illustrated in FIGS. 77-78; and a weight ($w\_q$) which assigns the importance for overall wellbeing or a particular target such as "Overall Cost" for each question. Answers can be in the range 0-10, and are stored as integers. Questions which have a positive sentiment indicate that a large answer is "good" wellbeing (e.g. sleep quality), whereas if the sentiment is negative a large score is "bad" (e.g. tummy ache). A sentiment of 0 indicates that a good score is somewhere in the middle and if you indicate a high or low value it's "bad" (e.g. urinary frequency: for "good" wellbeing this should be neither too frequent nor too infrequent).

The wellbeing score for a question $y\_q$ with answer $a\_q$ is calculated by:

If $(s\_q==1) y\_q=a\_q$ Else if $(s\_q==-1) y\_q=10-a\_q$

Else if $(s\_q==0)\{$if $(a\_q<=5) y\_q=a\_q*2$ else $y\_q=(10-a\_q)*2\}$

To calculate the overall wellbeing for a survey $W\_s$, we do a weighted average of all the wellbeing scores in that survey is performed:

$W\_s=\text{sum}(y\_q*w\_q)/\text{sum}(w\_q)$

For any individual survey, the result of the last survey that was filled in is presented, no matter when it was. If it was more than a week ago, a note saying that this survey has not been filled in within a week is shown, allowing the observer to weight the importance of this result with a view to the latency between recording and observation.

There are a number of ways the overall wellbeing score, or another target metric, which weights previous data, can be generated as follows:

First, take the last survey filled in (MOST RECENT): This is simple and intuitive—take the last survey that was filled in (or mean of surveys if several were filled in on the same day). However, it can be misleading, as it will be very affected by the type of survey the user last filled in. It does not necessarily give meaningful results, and can confuse the decision making process.

The second method involves including the last of each type of survey that was filled in, within a certain (five days as an example) time period (FIVE DAY). It assumes that all surveys filled in in the last five days have the same validity. This method takes the last of each type that was filled in and discards any that are more than five days old. The mean of the results of the remaining surveys is then the output. This gives a more meaningful smoothed output. However, it suffers from "jumps" as surveys with extreme values are removed from the dataset at day 6, and five days, or any set time period, is an arbitrary value.

The third method involves taking the last survey filled in for each type, regardless of how long ago it was filled in. The result is weighted by how long ago it was taken, where the most recent surveys are more highly weighted (LS).

$dd\_s$=no. days ago that survey was taken (0=today, 1=yesterday . . . )alpha$\_s$=2/(2+$dd\_s$):

weighting factor (=1 if survey was today,0.6 yesterday,0.16 if 10 days ago . . . )

$OW=\text{sum}(W\_s*\text{alpha})/\text{sum}(\text{alpha})$

This takes a weighted average of the last of each survey each certain type to be taken. Each survey type will be represented, no matter how long ago the last one was taken, but very old surveys will not affect the outcome much. Alpha could be adjusted to be more/less front-loaded. This method has one potential issue which is that when time rolls forward by a day, or whatever interval is determined for the analysis, the weights change but not directly in proportion.

If one fills in a survey today, and one yesterday then their weights are 1 and 0.6, so their relative contribution is 1:0.6 (63% of the result comes from the first survey). If a survey is not filled in a survey for another 5 days, then the only data analyzed is from the two surveys which are now at dd=5 and dd=6, with relative weights 0.29:0.25 (54% of the result comes from the first survey). This leads to a gradual change in the result, even though a survey has not been filled in in the interim.

This is not in itself a bad thing—it makes perfect sense. If one did a survey yesterday and another today, their wellbeing today is clearly much more affected by today's survey. If one waits 20 days, however, and look back—then the survey 20 days ago and one 21 days ago can be assumed to have roughly the same impact on the response today. This sort of analysis may confuse users, however can be corrected by input of notes or visualizations to alert the viewer to the change when time rolls forward.

The fourth method involves taking the LS result above but only calculate results when a survey is filled in, so that the results don't wander when surveys are not being filled (LS NO DRIFT).

This is exactly the same as method 3, except that the results are not allowed to vary in time when surveys are not filled in. This tends to be more intuitive to the end user, suggesting that wellbeing doesn't change if you don't fill in surveys. This method has the potential of being less scientifically accurate than method 3, but more visually pleasing.

Method 5 involves determining the irregular Exponential Moving Average (EMA, EMA Daily).

Exponential moving averages (EMAs) are very useful in producing smoothed average data. The general formula is $s_t=\alpha \cdot x_t+(1-\alpha)\cdot s_{t-1}$ where $\alpha$ is the smoothing factor ($0<\alpha<1$); $s_t$ is the EMA at time t; and $x_t$ is the raw input value at time t. The result is a simple weighted average of the current data, and the previous smoothed value. This is easily calculated as the current input only is needed, and the last value of the function. $\alpha$ is related to the window (k) of a simple moving average by $\alpha \sim 2/(k+1)$, so an EMA with an approximately five day look back has α~0.3, and that is what we are using here. (α=1 will return the original data.)

The EMAs require a regular time series. We need to use an approximation that allows different time periods between each measure.

$$a = \text{deltaTime}/\text{alpha}; u = \exp(a*-1); v = (1-u)/a; s_t = (u*s_{t-1}) + ((v-u)*x_{t-1}) + ((1.0-v)*x_t);$$

This is calculated on the day, or other interval, that each survey is taken. It can be "forward filled" for days where no new surveys are taken. This will make any smoothing fits more accurate, and show a flat line for times when surveys are not filled. This is the method that has been used for the embodiment described and to access the data as a user then a survey must be filled in.

From here the result is either represented as a raw integer in the graphs view or multiplied by two for the combined pictorial representation view. The number is then rounded to the nearest whole number and assigned to one of the following png files for each category as below where the top left is the highest score for each category and the bottom right is the lowest score.

Figure 82:
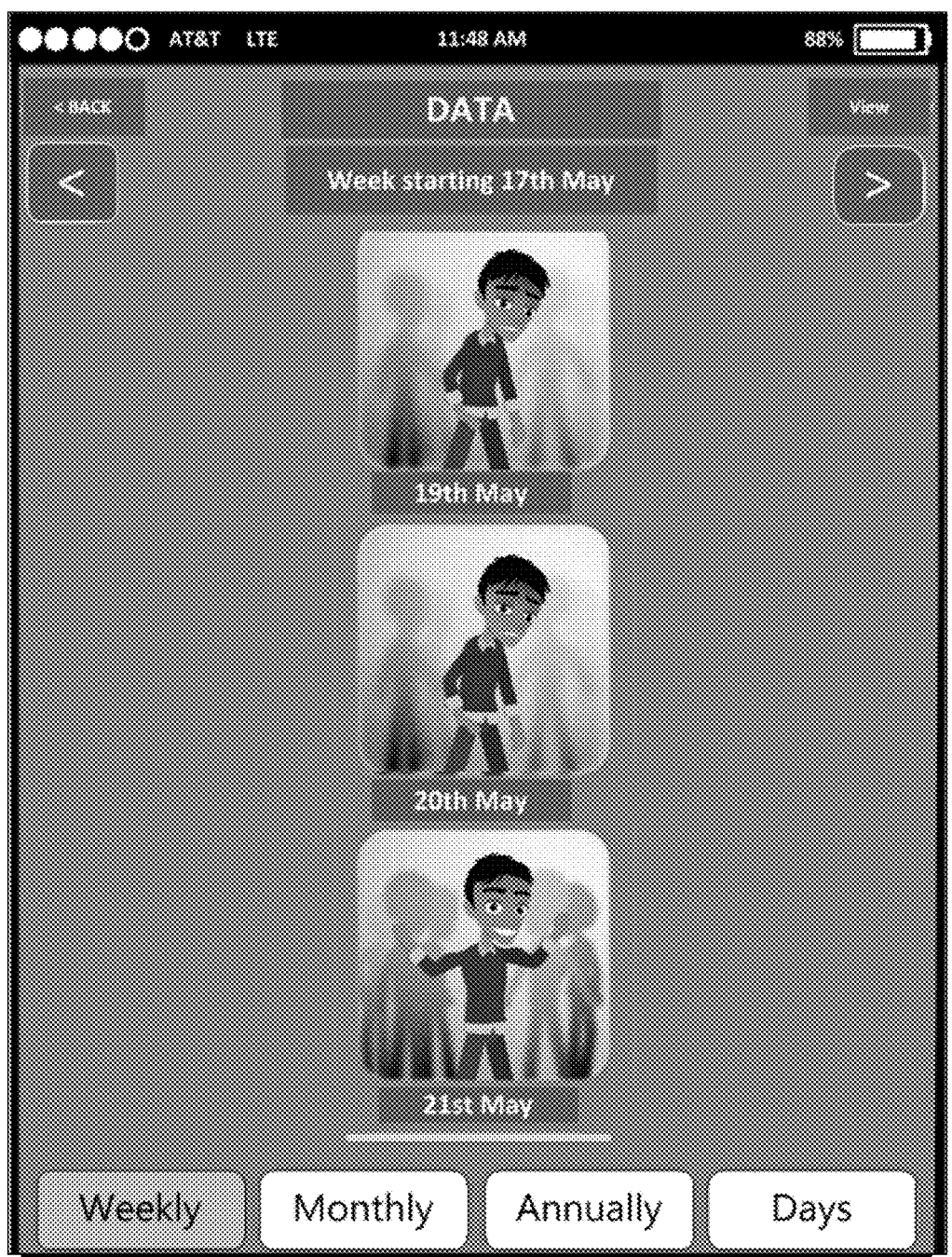
FIG. 82 illustrates a user interface in which a composite output for the health and wellbeing of a user is shown over a course of weeks.

FIG. 82 illustrates a user interface 8200 in which a composite output for the health and wellbeing of a user is shown over a course of weeks.

Figure 83:
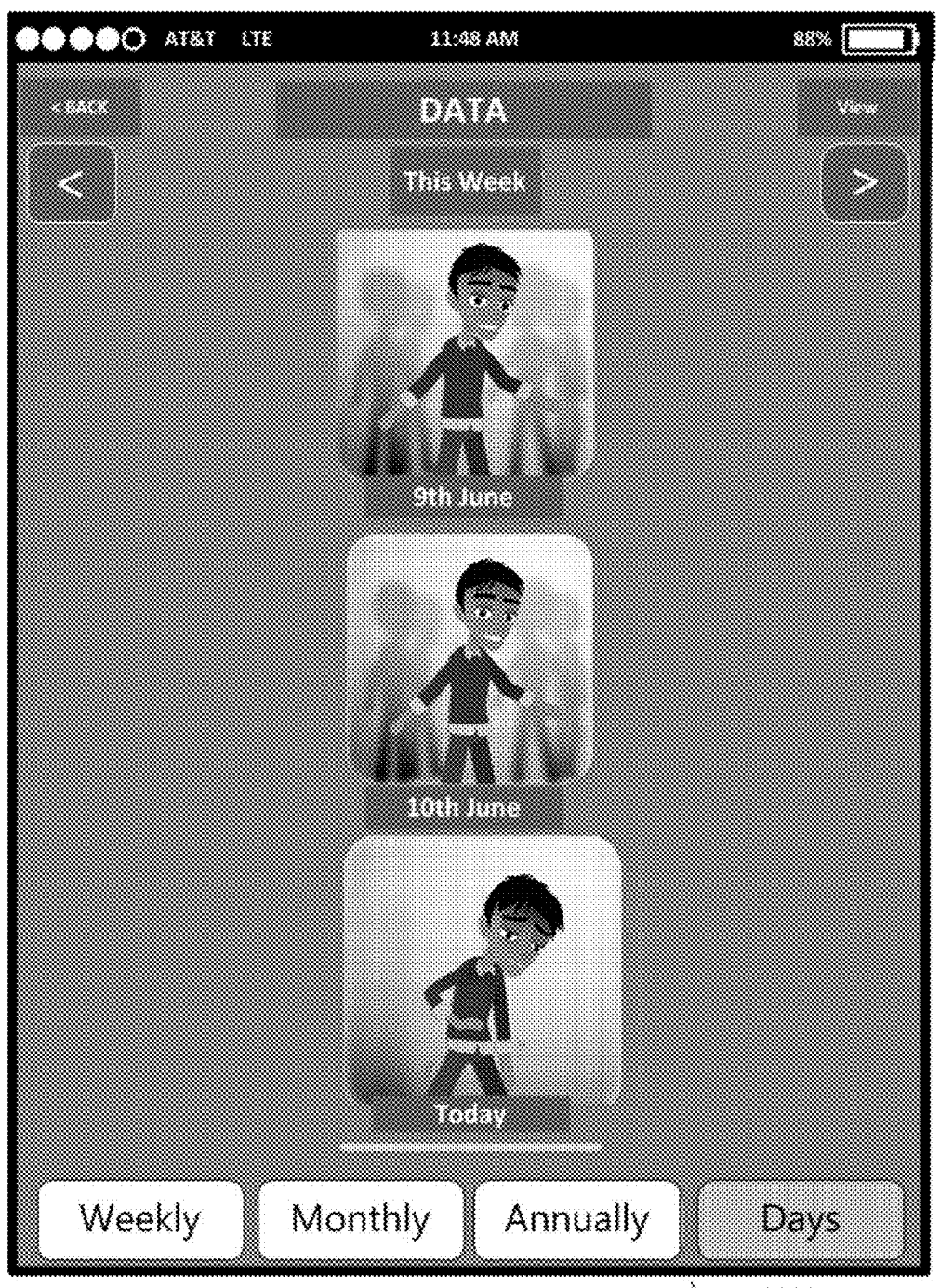
FIG. 83 illustrates a user interface in which a composite output for the health and wellbeing of a user is shown over a course of days.

FIG. 83 illustrates a user interface 8300 in which a composite output for the health and wellbeing of a user is shown over a course of days.

Figure 84:
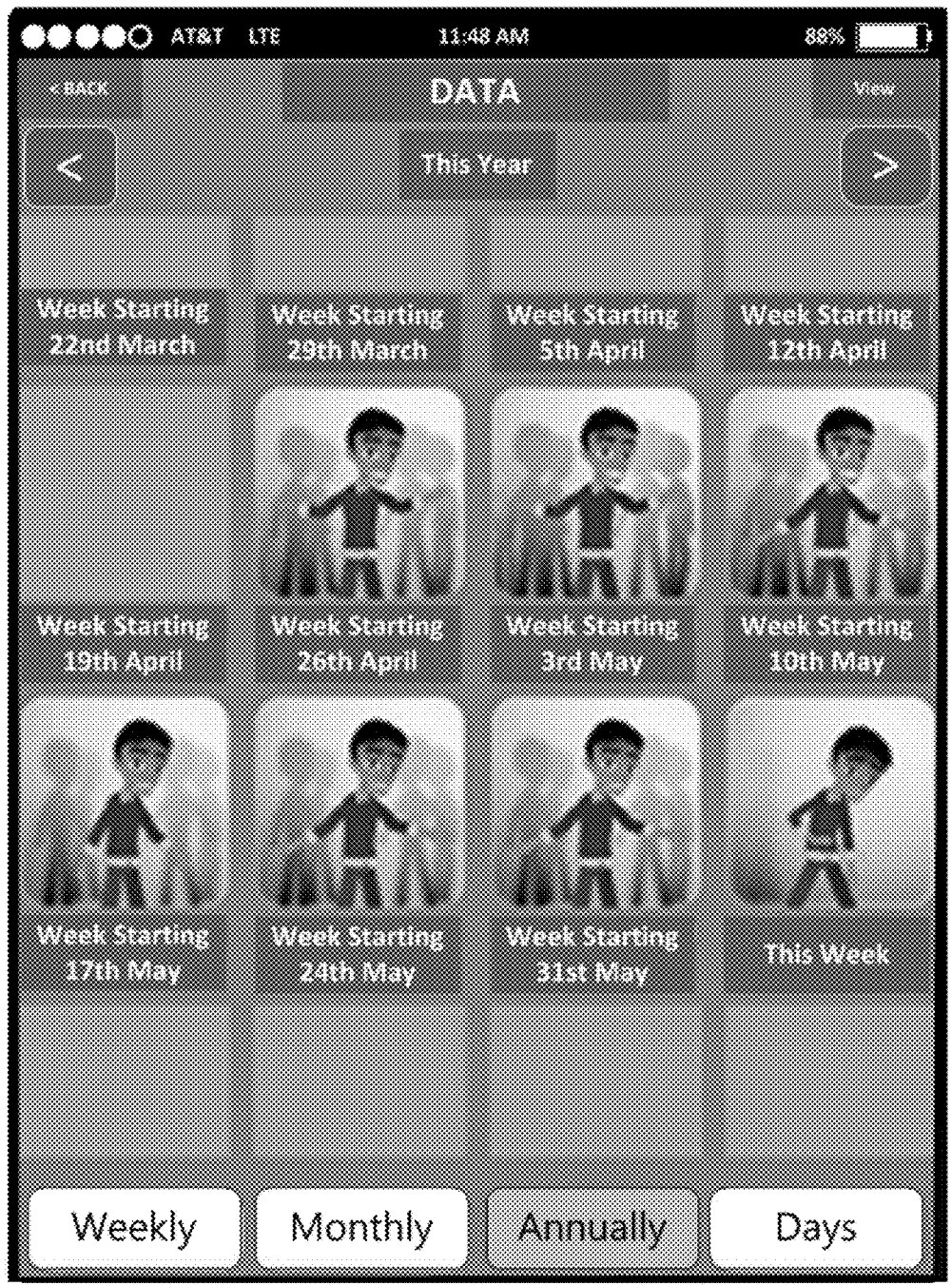
FIG. 84 illustrates a user interface in which a composite output for the health and wellbeing of a user is shown annually in increments of weeks.

FIG. 84 illustrates a user interface 8400 in which a composite output for the health and wellbeing of a user is shown annually in increments of weeks.

Figure 85:
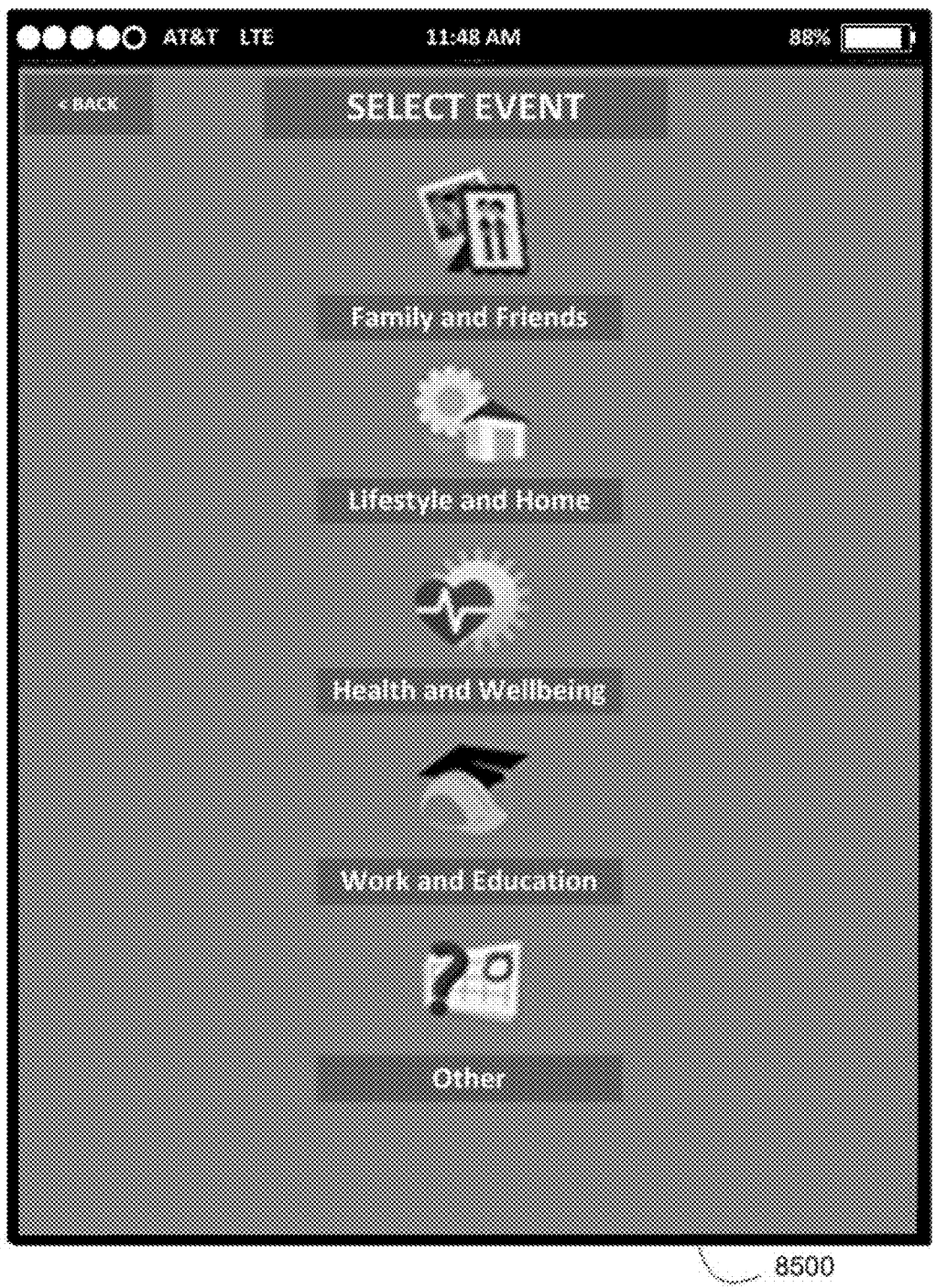
FIG. 85 illustrates a user interface in which particular types of "individual" events can be selected by a user.

FIG. 85 illustrates a user interface 8500 in which particular types of "individual" events can be selected by a user.

Figure 86:
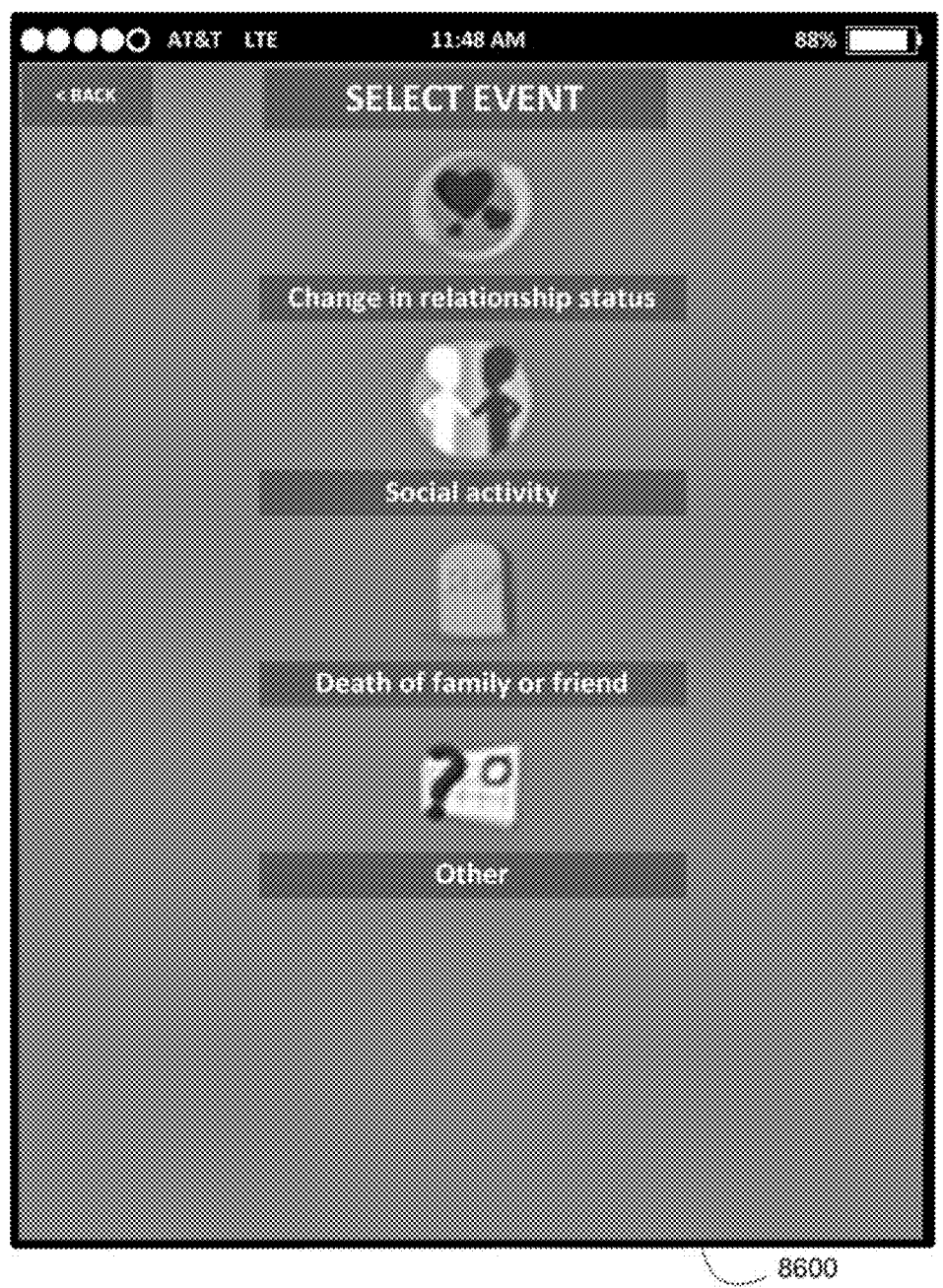
FIG. 86 illustrates a user interface in which particular types of "family and friends" events can be selected by a user.

FIG. 86 illustrates a user interface 8600 in which particular types of "family and friends" events can be selected by a user.

Figure 87:
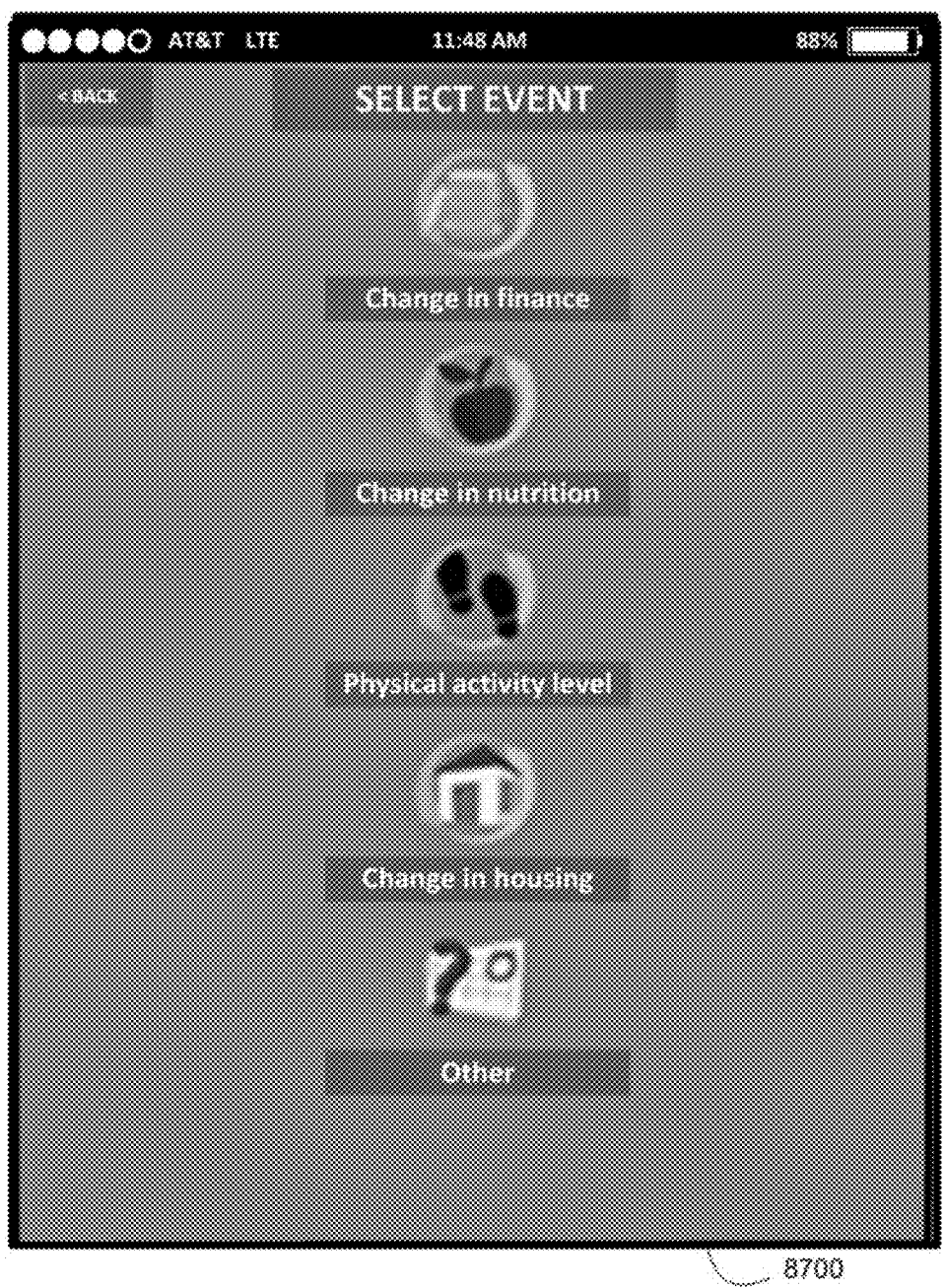
FIG. 87 illustrates a user interface in which particular types of "lifestyle and home" events can be selected by a user.

FIG. 87 illustrates a user interface 8700 in which particular types of "lifestyle and home" events can be selected by a user.

Figure 88:
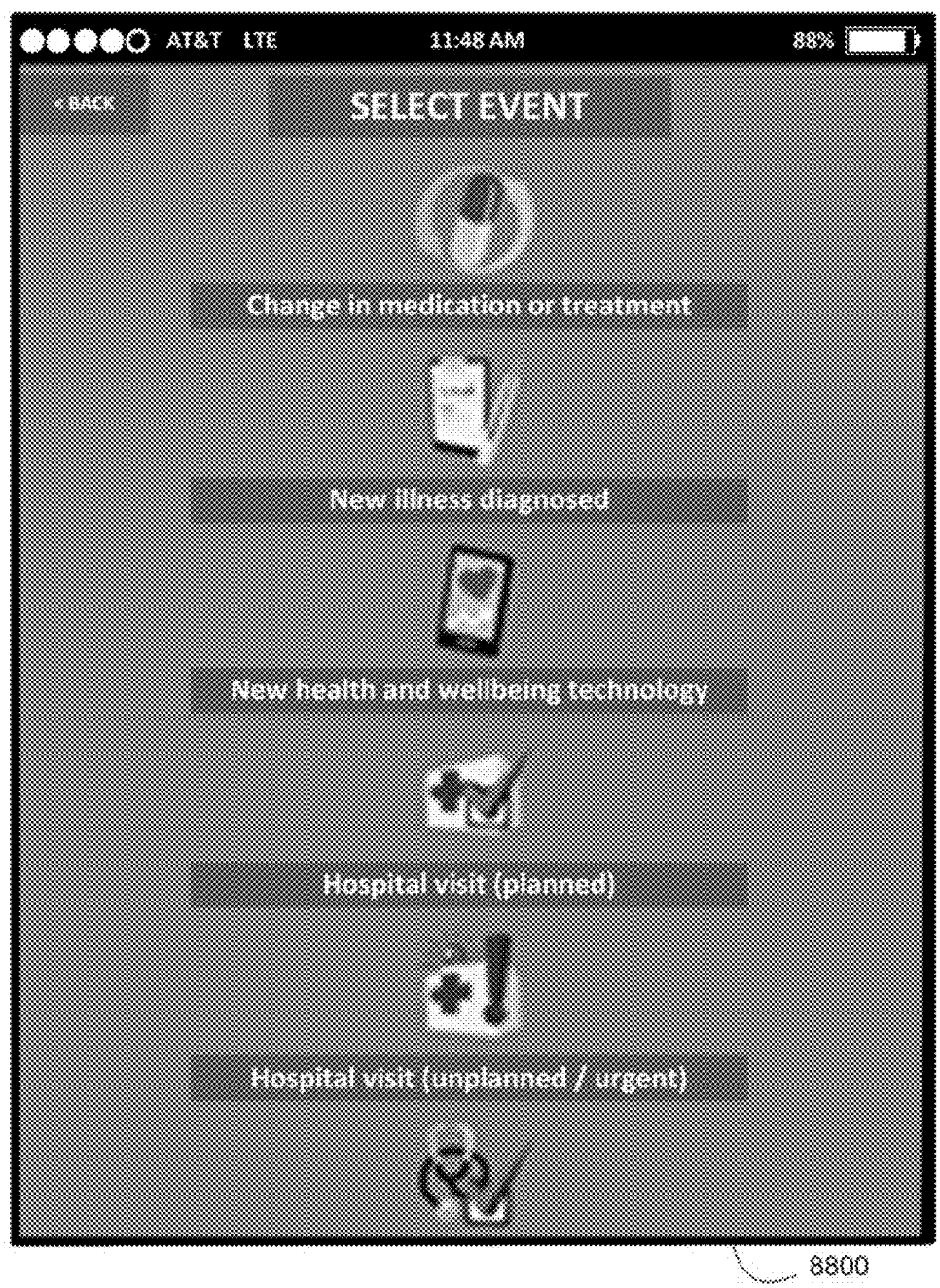
FIG. 88 illustrates a user interface in which particular types of "health and wellbeing" events can be selected by a user.

FIG. 88 illustrates a user interface 8800 in which particular types of "health and wellbeing" events can be selected by a user.

Figure 89:
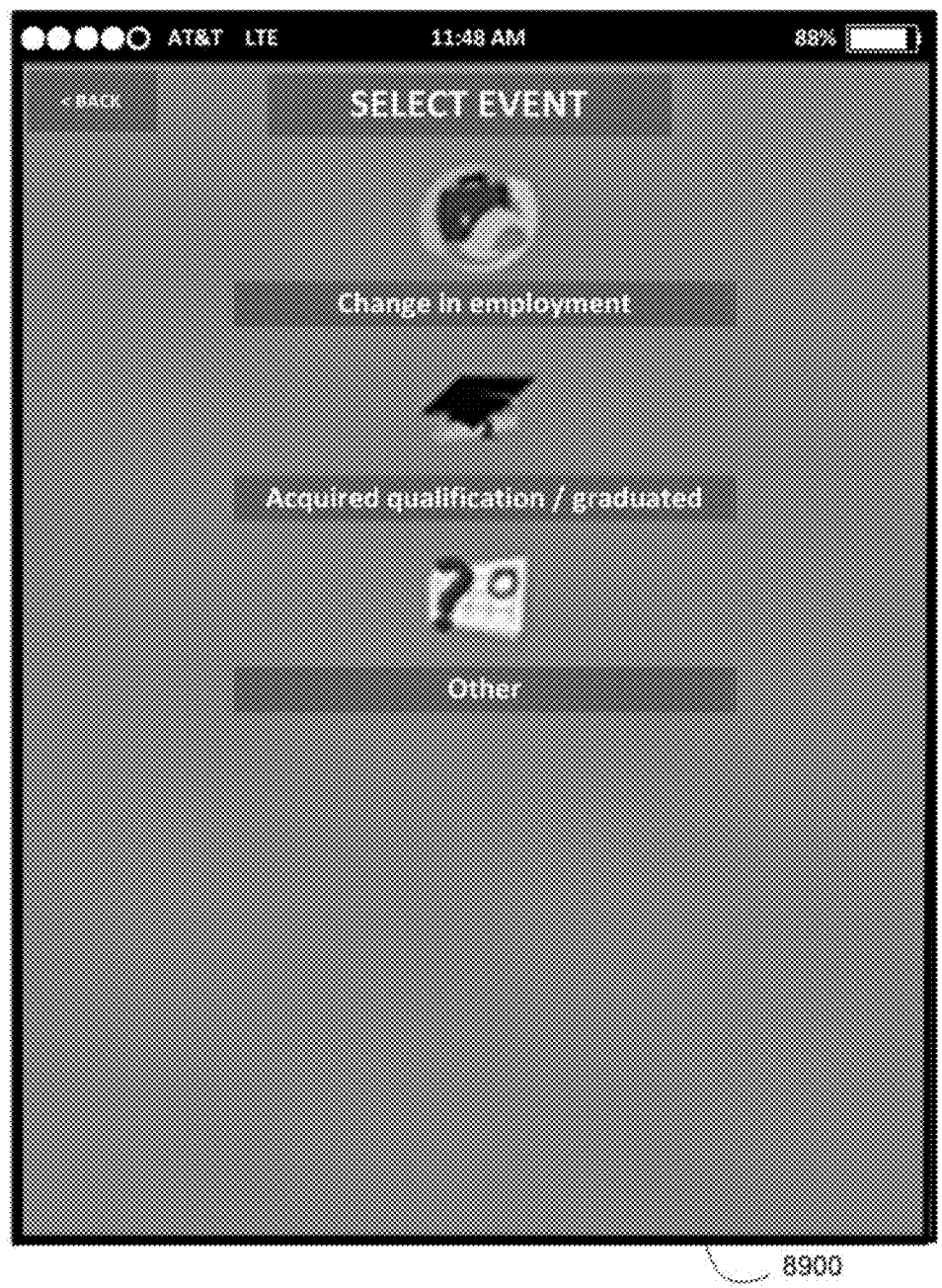
FIG. 89 illustrates a user interface in which particular types of "work and education" events can be selected by a user.

FIG. 89 illustrates a user interface 8900 in which particular types of "work and education" events can be selected by a user.

Figure 90:
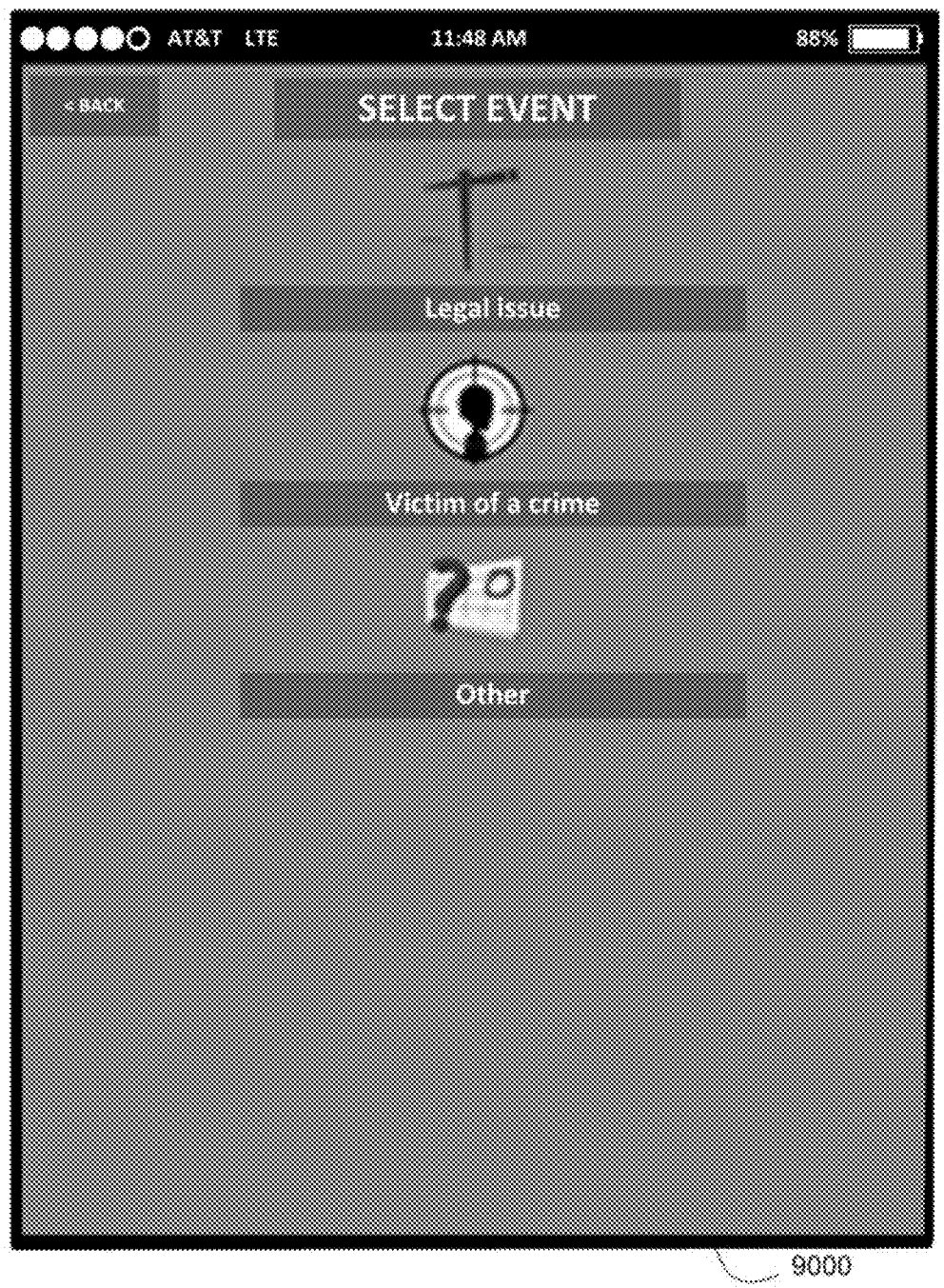
FIG. 90 illustrates a user interface in which particular types of "miscellaneous" events can be selected by a user.

FIG. 90 illustrates a user interface 9000 in which particular types of "miscellaneous" events can be selected by a user.

Figure 91:
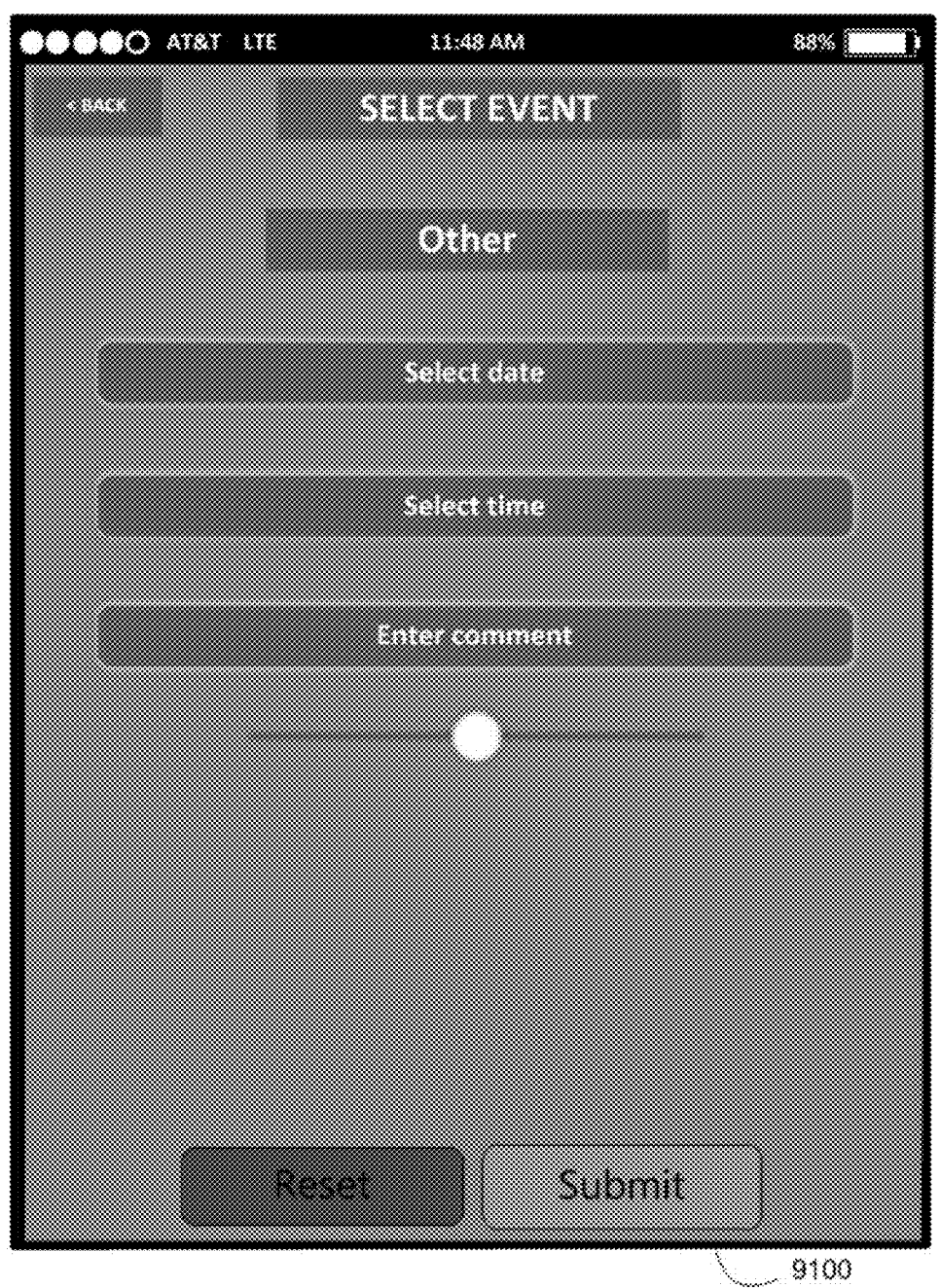
FIG. 91 illustrates a user interface in which a custom event can be entered by a user.

FIG. 91 illustrates a user interface 9100 in which a custom event can be entered by a user. Data regarding entered for custom events includes details such as time and impact blue slider along with notes. The system automatically defaults to current time and location tagging with any impact being neutral or in the middle as per the diagram. The user then adjusts the slider from the neutral/default position as desired.

The data entered or otherwise captured through the mobility device, such as an iPhone or iPad, is stored and can be viewed by the end user in relation to overall wellbeing scores and how they change over time preceding or after an event. The events and wellbeing data is uploaded wireless to the server where it can be further analyzed either individually, or on a population basis.

For example, one could search the database of an individuals for aggravation of irritable bowel syndrome as an event and seek correlating events of wellbeing scores preceding this event. It may be found that as a result of this search and analysis that eating bananas 7-9 days was a regular association with an increase in negative bowel symptoms and the flare up. This would allow the user to trial not eating bananas for a period to see if the irritable bowel syndrome symptoms would decrease. Another finding might be that in the days prior to a flare up of bowel symptoms that anxiety and fatigue levels are increased whereas activity is decreased, through measurement of self-report, wearable sensing devices and movement around the house assessed by analysis smart environmental sensors. By logging this pattern of data change the system could then recognize it in the future and flag the trend early allowing for early intervention and potential avoidance of the flare up of symptoms. In another though related scenario, or scenarios, the individual may have the alert that their wellbeing was trending towards an irritable bowel syndrome "event". They could then log an intervention such as a medication, change in activity or nutrition. The system could then interrogate this intervention by comparing the time before and after the intervention to measure the efficacy of the intervention. The system allows analysis of variable time periods before and after certain interventions with further analysis of what reported metrics are most impacted.

In view of the foregoing, it will be appreciated that apparatus, systems, and methods in accordance with one or more aspects and features of the invention will engage and promote by individuals of varying literacy levels the reporting of their health information more frequently and accurately over time, and empower such individuals to better understand and act upon feedback provided in and by such apparatus, systems, and methods. Health literacy of users will be improved via targeted feedback and information relating to their health. Ultimately for such individuals a clearer picture will be provided of their health and wellbeing; how it changes over time; and the impact of events, interventions or lifestyle choices. This, in turn, will or may enhance self-care and encourage such individuals to make and maintain positive lifestyle choices. For professional healthcare providers such as clinicians, apparatus, systems, and methods in accordance with one or more aspects and features of the invention will enable earlier detection of health deterioration with alert functionality, and enhanced decision support. This will or may lead to improved health outcomes, better patient satisfaction, and will reduce costs associated with undetected health deterioration and the need for costlier intervention. Additionally, apparatus, systems, and methods in accordance with one or more aspects and features of the invention allow enhanced accessibility of medical records in a way that can be understood by individuals of a range of literacy levels, thereby further enhancing health knowledge and self-care by such individuals. Overall benefits further include enhanced community care and home care, decreasing costs associated with transport, parking, and time off work associated with hospital care.

It will be appreciated from the foregoing that health reporting apparatus, systems and methods in accordance with one or more aspects and features of the invention include progressive combinatorial pictorial visualizations and that at least some embodiments of the invention relate to apparatus, systems, and methods incorporating progressive combinatorial pictorial visualizations whether used in the context of the above described health reporting context or in other health related contexts. As describe above, the disclosed progressive pictorial representations are linked to numerical outputs that are calculated based on the mental, social and physical data that is entered by an individual using the slider controls of the various user interfaces. This could be applied to other situations such as, for example, heart failure where that data entered by an individual pertains to coughing, swollen ankles, fatigue, and cyanosis (blue peripheries). This is illustrated, for example, in each of FIGS. 92 and 93.

Other examples of use of this technology include receiving data pertaining to alcohol or substance abuse; job satisfaction; home situation; and activity. For instance, this is illustrated in FIG. 94, wherein the separate pictorial visualizations corresponding to input that has been received are shown along the top of the interface 9400 in the area indicated at 9425, and the combined combinatorial pictorial visualization is shown below in the area indicated at 9450.

Figure 95:
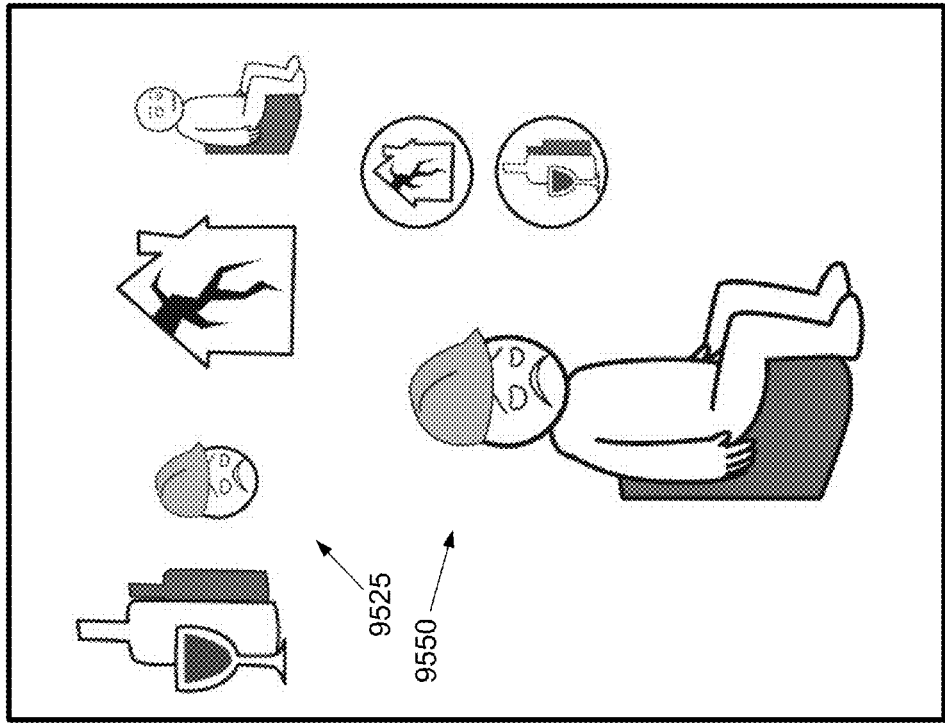
FIG. 95 illustrates the same combination of factors as those represented in FIG. 94, but are represented as being severe, which indicates a high likelihood of domestic violence.

Another instance of this is illustrated in FIG. 95, wherein the separate pictorial visualizations corresponding to input that has been received are shown along the top of the interface 9500 in the area indicated at 9525, and the combined combinatorial pictorial visualization is shown below in the area indicated at 9550.

Figure 94:
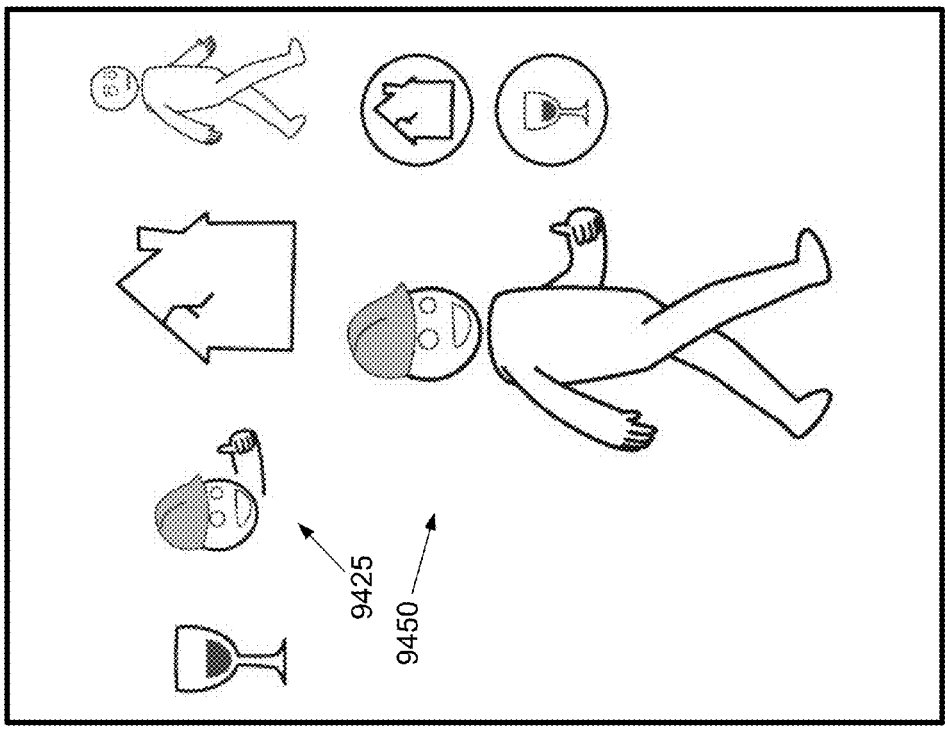
FIG. 94 illustrates an individual with a combination of factors including alcohol or substance abuse; job satisfaction; home situation; and activity, which combined factors in the illustrated severity indicate a healthy individual.

It is believed that the metrics obtained in the instances illustrated in FIGS. 94 and 95 could be used as indicators or predictors of likelihood of domestic violence, for example.

Another example that could be represented in a progressive combined pictorial representation is a combination of: feeling supported; mood; self-image; activity (as self-assessed or measured by a wrist tracker"; and feelings of control. For instance, this is illustrated in FIG. 96, wherein the separate pictorial visualizations corresponding to input that has been received are shown along the top of the interface 9600 in the area indicated at 9625, and the combined combinatorial pictorial visualization is shown below in the area indicated at 9650.

Figure 97:
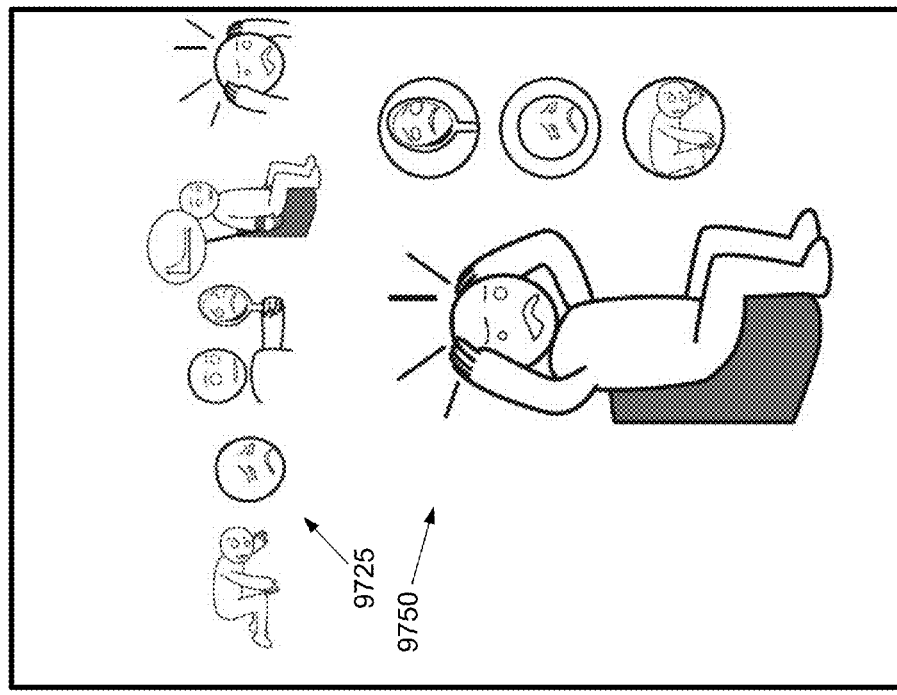
FIG. 97 illustrates the same combination of factors as those represented in FIG. 96, but are represented as being severe with deterioration, which indicates someone who has a high risk of suicide.

Another instance of this is illustrated in FIG. 97, wherein the separate pictorial visualizations corresponding to input that has been received are shown along the top of the interface 9700 in the area indicated at 9725, and the combined combinatorial pictorial visualization is shown below in the area indicated at 9750.

Figure 96:
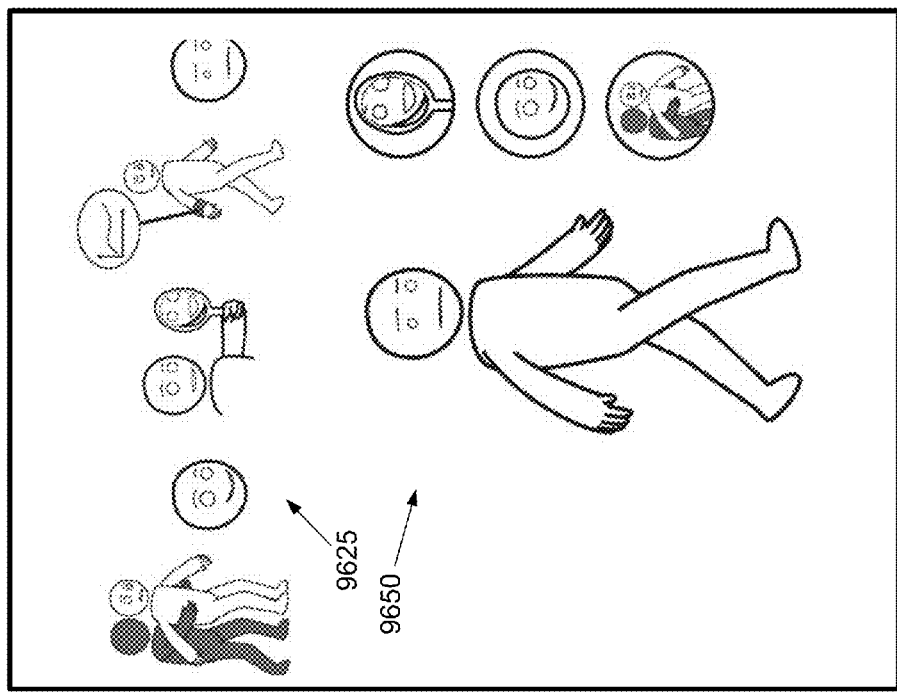
FIG. 96 illustrates an individual with a combination of factors including feeling supported; mood; self-image; activity (self-assessed or measured by a tracker); and feelings of control, which combined factors in the illustrated indicate a healthy individual.

It is believed that the metrics obtained in the instances illustrated in FIGS. 96 and 97 could be used as indicators or predictors for suicide risk.

Figure 98:
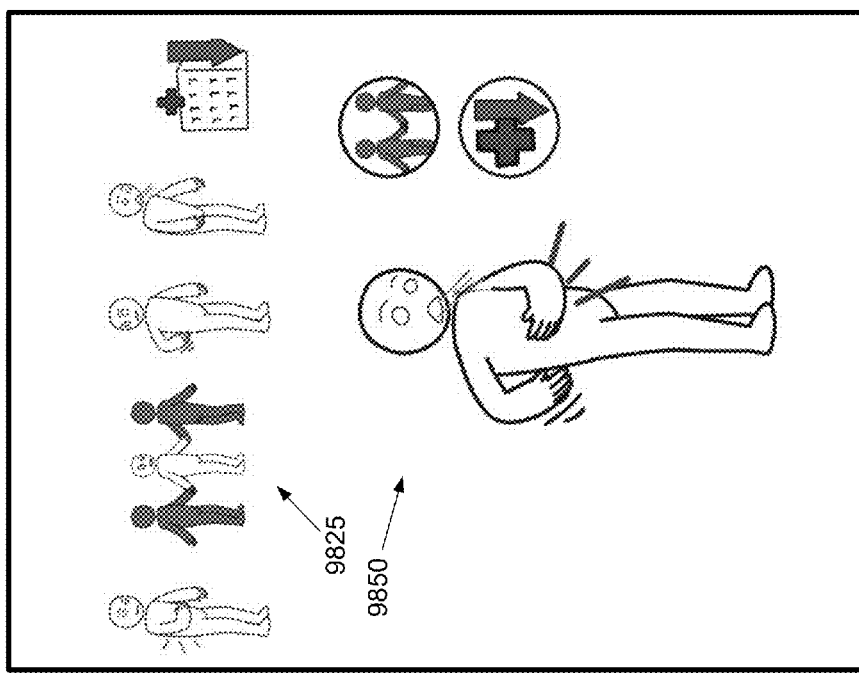
FIG. 98 illustrates an individual with a combination of factors including discomfort; loneliness; itchiness; and shortness of breath, which combined factors in the illustrated severity indicate an individual who is not particularly healthy but who has a low risk of hospital admission.

Yet another example that could be represented in a progressive combined pictorial representation is a combination of discomfort, loneliness, itchiness, and shortness of breath, and it is believed that the metrics obtained could be a powerful indicator for likelihood of hospital admission. For instance, this is illustrated in FIG. 98, wherein the separate pictorial visualizations corresponding to input that has been received are shown along the top of the interface 9800 in the area indicated at 9825, and the combined combinatorial pictorial visualization is shown below in the area indicated at 9850.

Figure 99:
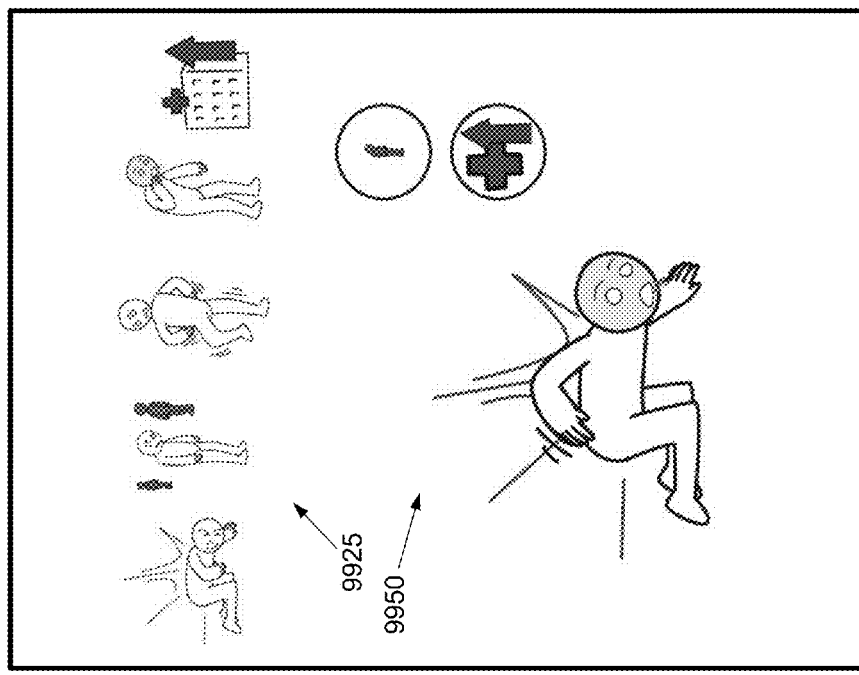
FIG. 99 illustrates the same combination of factors as those represented in FIG. 98, but with deterioration and are indicative of someone who is at high risk of hospitalization.

Another instance of this is illustrated in FIG. 99, wherein the separate pictorial visualizations corresponding to input that has been received are shown along the top of the interface 9900 in the area indicated at 9925, and the combined combinatorial pictorial visualization is shown below in the area indicated at 9950.

It will further be appreciated that in each of the examples of FIGS. 94-99, the pictorial representation for an input can be combined with one or more other pictorial representations in order to generate the combinatorial pictorial visualization, with a pictorial representation for an input being selected—based on the degree, level, or extent thereof as indicated in the input—from a set of pictorial representations for that input that extend along a spectrum or range between best and worst possibilities. Furthermore, one or more other pictorial representations could be included as a group of icons around such combinatorial pictorial representation.

Figure 100:
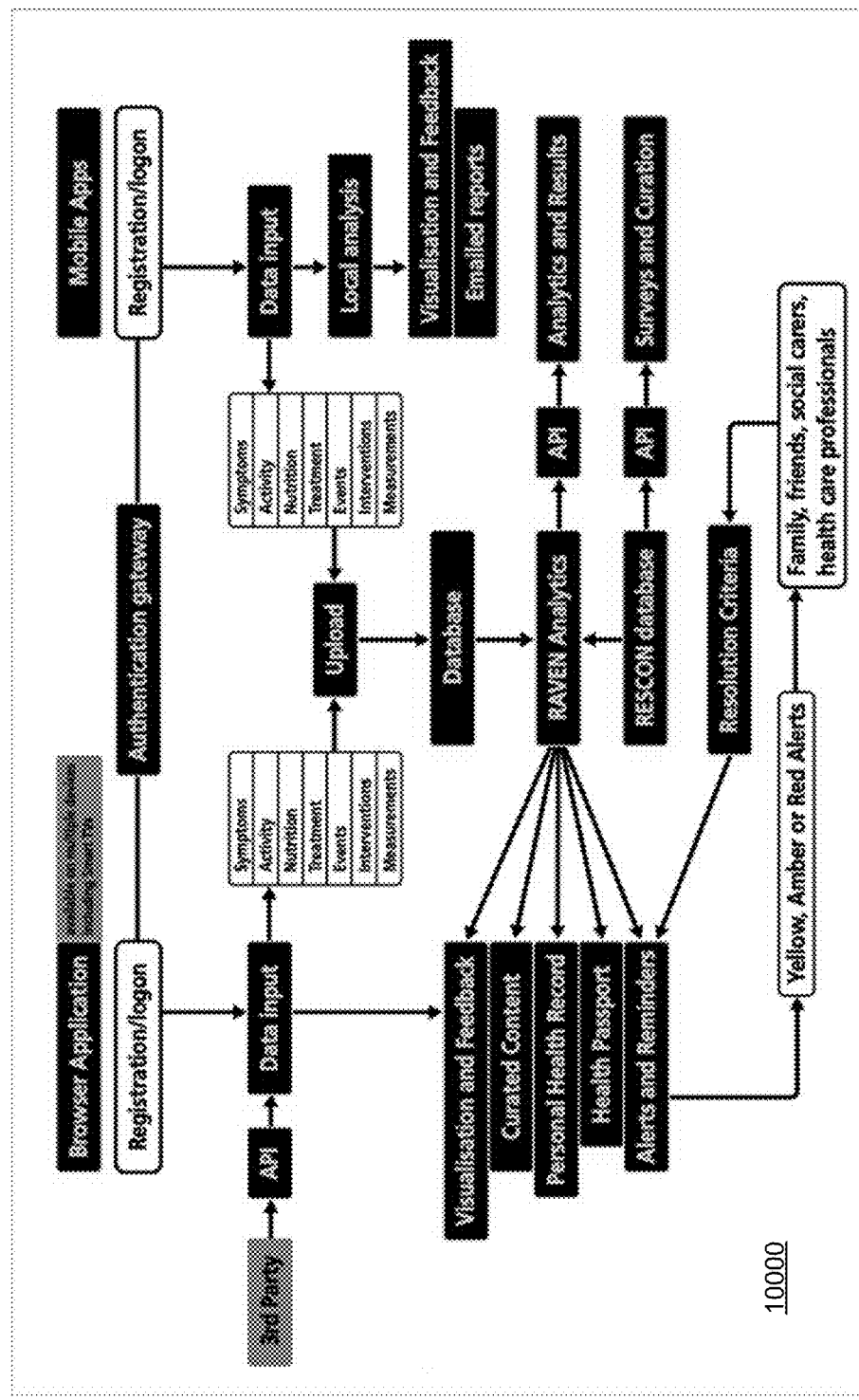
FIGS. 100 and 101 illustrate collectively a system architecture for implementing preferred embodiments.
Figure 101:
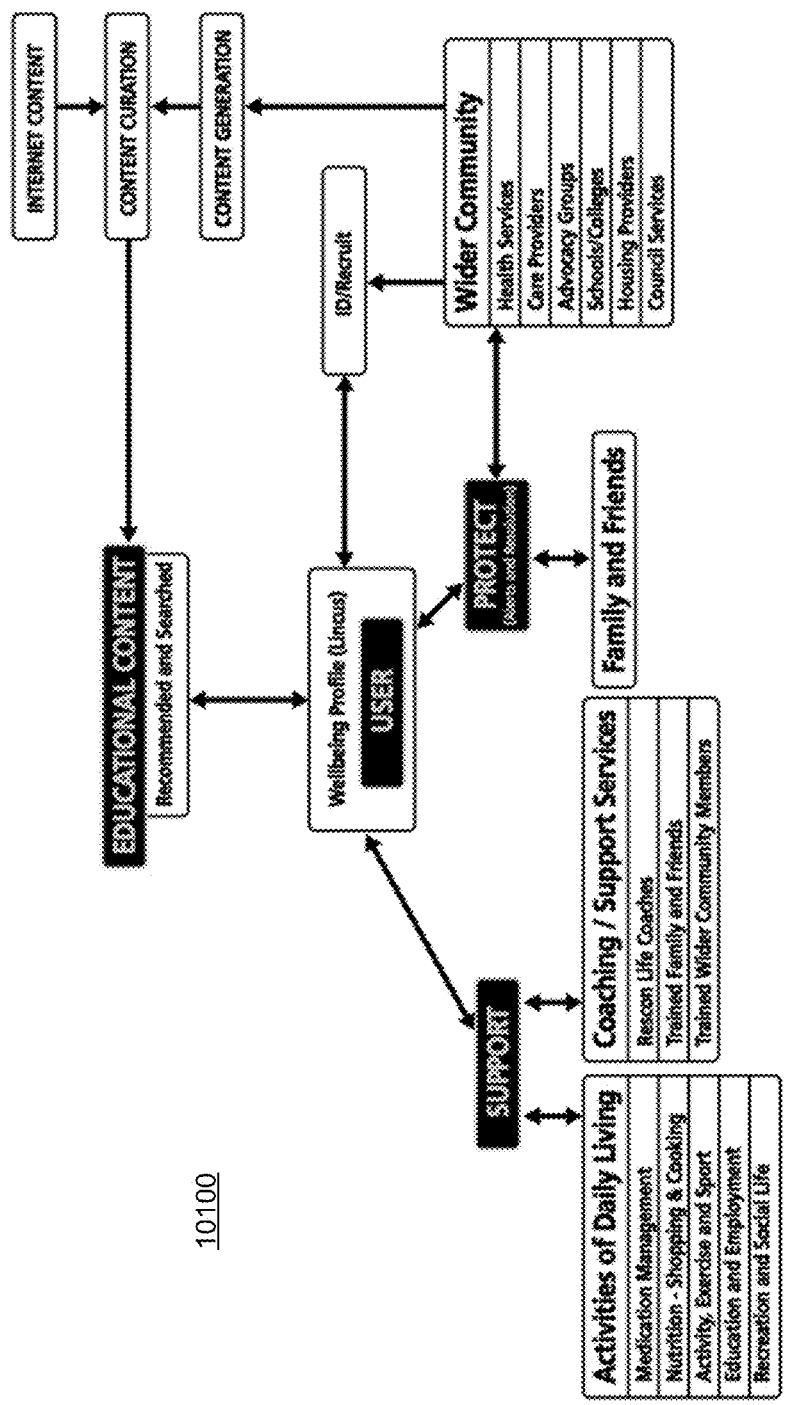
Figure 105:
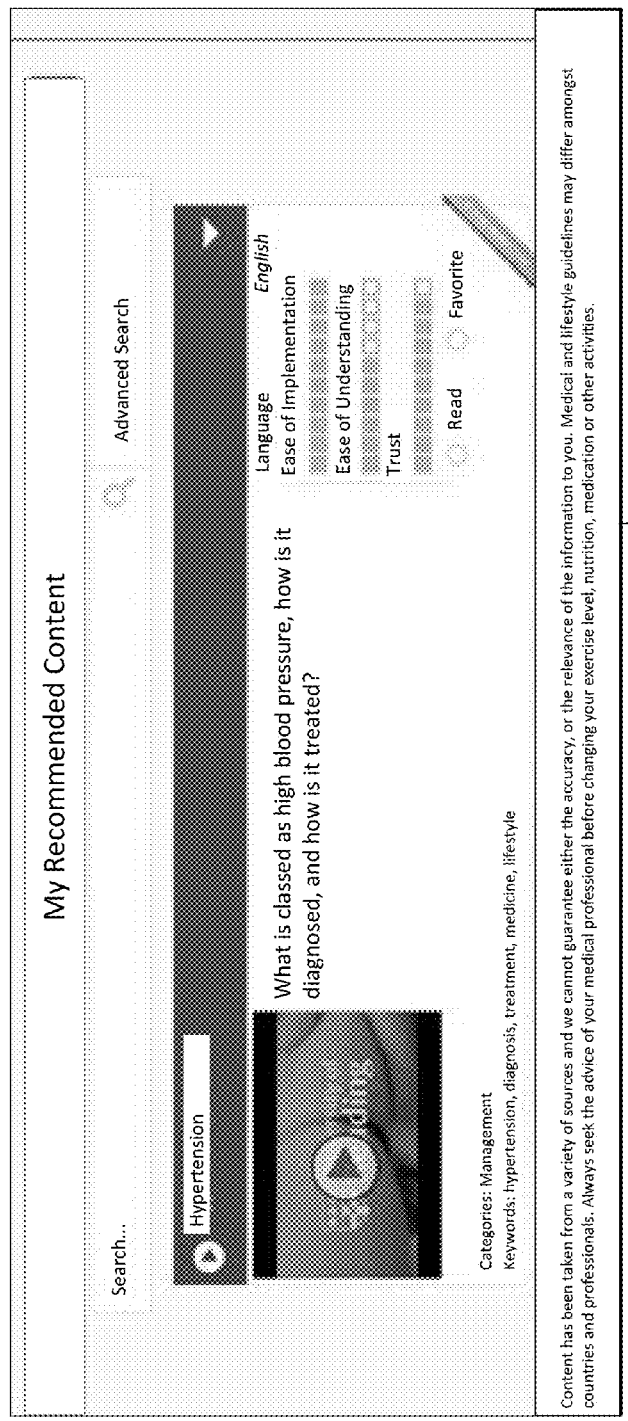
FIG. 105 illustrates exemplary content delivery via a user interface, which content is provided to a user using the personalized recommended content engine and search engine of preferred embodiments of the invention.

With reference FIGS. 100-101, a system architecture of a preferred implementation is collectively illustrated. In particular, FIG. 100 illustrates a computer architecture 10000 in which "Rescon" is illustrated in FIG. 100 as representative of a service provider of a database of user profiles and surveys, which facilitate such preferred implementation. The profiles and surveys are provided by Rescon via a system branded as "lincus", which is sometimes referred to in the drawings, such as FIG. 101. FIG. 101 further illustrates an abstracted architecture 10100 of a preferred embodiment showing the support, protection, and education of a user.

In one or more preferred implementations, and with reference to FIGS. 102-105, a personalized recommended content engine and search engine is provided, which is designed to match content with an individual's profile, thereby delivering a recommended content service. This includes the following components: a content manager profile, where the content manager reviews content and curates it; a content manager user interface and database, where content is reviewed; content that has been curated—this can be stored privately or on the world wide web and accessible through a URL; a matching algorithm that sorts content from highest rank to lowest rank; and a database of read, favorite, and ranked content that is stored and linked to the individual, allowing for later changes to the individuals profile, and refinement of recommendations for individuals with similar profiles.

In greater detail, the content manager profile is used to identify more relevant content for an individual and can be taken into account when content from the content manager is recommended or not. For instance, content from a Professor at Yale may be more likely to be recommended than content from an undergraduate at Harvard. The content manager curates content utilizing a structure review process. In addition to the categories seen in the user interface 10200 of FIG. 102, other categories can be used, such as usefulness and information density, to further stratify content. The content that is curated is stored in a database and made available through the content manager portal Curated content, as seen in the user interface 10300 of FIG. 103. The matching algorithm is used to match content to users, which is then ranked.

Figure 104:
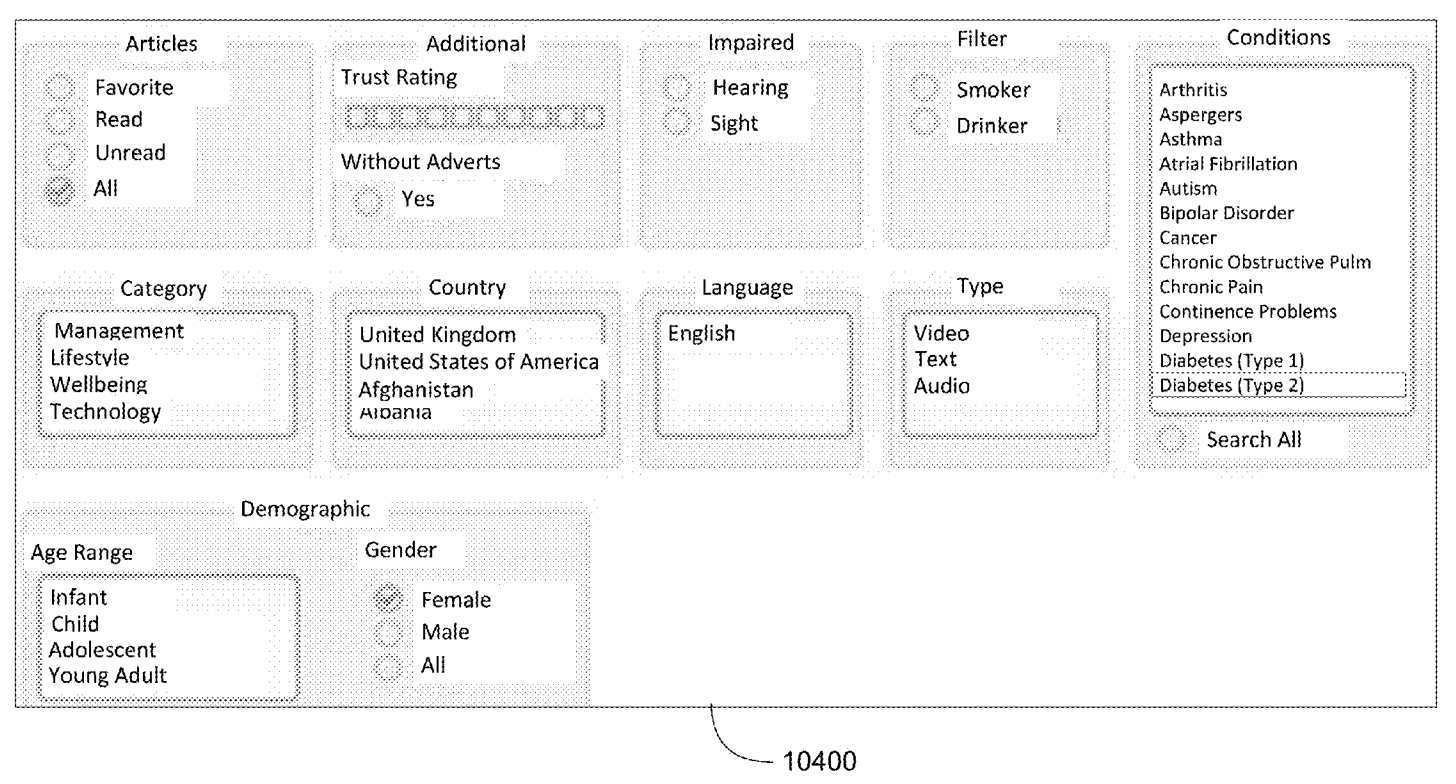

Additionally, a user can search through curated—and hence trusted—content utilizing normal search terms with matching functions using a representative interface 10400 as illustrated, for example, in FIG. 104. An example of recommended content that is provided to an individual user is illustrated via the user interface 10500 of in FIG. 105. Furthermore, a database of how each user responds to recommended or searched content can be compiled, and the database can be used to modify profiles, recommendations, and inform recommendations to make for individuals with similar profiles that are demographically or otherwise matched.

It is believed that use of the personalized recommended content engine and search engine will improve health literacy, that access to curated articles will help educate care givers about people that they support, increase rapid academic article review and improve information search functionality, and enhance professional training with the right information at the right place and right time.

Based on the foregoing description, it will be readily understood by those persons skilled in the art that the present invention is susceptible of broad utility and application.

Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method for automatically creating a computer-generated composite pictorial visualization based on multivariate health data for a user, the method comprising:
   (a) displaying, to a user via a touchscreen display associated with an electronic device,
      (i) a first input control displayed in association with a first health question,
      (ii) a second input control displayed in association with a second health question, and
      (iii) a third input control displayed in association with a third health question,
      (iv) wherein the first, second, and third health questions are all related to a first health metric;
   (b) receiving, from the user via touching of the touchscreen display, first user input corresponding to interaction with the first input control;
   (c) receiving, from the user via touching of the touchscreen display, second user input corresponding to interaction with the second input control;
   (d) receiving, from the user via touching of the touchscreen display, third user input corresponding to interaction with the third input control;
   (e) determining, based on the first user input, a first answer value associated with the first question;
   (f) determining, based on the second user input, a second answer value associated with the second question;
   (g) determining, based on the third user input, a third answer value associated with the third question;
   (h) determining, based on the first answer value associated with the first question, a first score for the first answer by,
      (i) accessing a sentiment value associated with the first question,
      (ii) calculating the first score for the first answer based on the first answer value and the accessed sentiment value associated with the first question, wherein,
         (A) if the sentiment value is positive, the first score is set to be the first answer value,
         (B) if the sentiment value is negative, the first score is set to be the difference between a maximum possible first answer value and the input first answer value, and
         (C) if the sentiment value is zero, the first score is calculated differently based on whether the first answer value was above or below the median possible first answer value;
   (i) determining, based on the second answer value associated with the second question, a second score for the second answer by,
      (i) accessing a sentiment value associated with the second question,
      (ii) calculating the second score for the second answer based on the second answer value and the accessed sentiment value associated with the second question, wherein,
         (A) if the sentiment value is positive, the second score is set to be the second answer value,
         (B) if the sentiment value is negative, the second score is set to be the difference between a maximum possible second answer value and the input second answer value, and
         (C) if the sentiment value is zero, the second score is calculated differently based on whether the second answer value was above or below the median possible second answer value;
   (j) determining, based on the third answer value associated with the third question, a third score for the third answer by,
      (i) accessing a sentiment value associated with the third question,
      (ii) calculating the third score for the third answer based on the third answer value and the accessed sentiment value associated with the third question, wherein,
         (A) if the sentiment value is positive, the third score is set to be the third answer value,
         (B) if the sentiment value is negative, the third score is set to be the difference between a maximum possible third answer value and the input third answer value, and
         (C) if the sentiment value is zero, the third score is calculated differently based on whether the third answer value was above or below the median possible third answer value;
   (k) determining a weighted metric score for the first health metric by,
      (i) accessing weight values associated with the first, second, and third questions, and
      (ii) calculating the weighted metric score for the first health metric utilizing the calculated first, second, and third scores and the accessed weight values;
   (l) calculating a first image value for the first health metric based on the determined weighted metric score;
   (m) accessing, based on the calculated first image value, from a data store containing a plurality of pictorial images each associated with a respective image value for the first health metric, a first component pictorial image associated with the calculated first image value;
   (n) accessing, based on a calculated second image value, from a data store containing a plurality of pictorial images each associated with a respective image value for a second health metric, a second component pictorial image associated with the calculated second image value;
   (o) accessing, based on a calculated third image value, from a data store containing a plurality of pictorial images each associated with a respective image value for a third health metric, a third component pictorial image associated with the calculated third image value;
   (p) automatically combining the accessed first component pictorial image, the accessed second component pictorial image, and the accessed third component pictorial image to generate the composite pictorial visualization;

(q) displaying, to the user via the touchscreen display, the generated composite pictorial visualization;

(r) communicating the generated composite pictorial visualization from the electronic device for view by others, wherein the generated composite pictorial visualization is displayed to others by way of a social networking application; and (s) displaying on a different electronic device the generated composite pictorial visualization.

2. The method of claim 1, further comprising maintaining a profile of the user, wherein the weighting is based at least in part on the profile of the user that is maintained.

3. The method of claim 2, wherein the profile includes a medical history of the user.

4. The method of claim 1, further comprising maintaining a profile of the user, wherein the determining of the pictorial visualization is based at least in part on the profile of the user that is maintained.

5. The method of claim 1, wherein the method further comprises receiving input representative of a physical determinant of overall health of the user from an electronic sensor that acquires data pertaining to the physical determinant.

6. The method of claim 5, wherein the electronic sensor is worn by the user.

7. The method of claim 5, wherein the electronic sensor is a scale.

8. The method of claim 5, wherein the electronic sensor is an exercise machine.

9. The method of claim 5, wherein the electronic sensor is a phone.

10. The method of claim 5, wherein the electronic sensor is a watch.

11. A method for automatically creating a computer-generated composite pictorial visualization based on multivariate health data for a user, the method comprising:

(a) displaying, to a user via a touchscreen display associated with an electronic device, a first graphical user interface including
  (i) a first slider input control displayed in association with,
    (A) a label indicating a first health parameter,
    (B) a first pictorial character image displayed proximate a first end of the first slider input control representing a first state of the first health parameter, and
    (C) a second pictorial character image displayed proximate a second, opposite end of the first slider input control representing a second, opposite state of the first health parameter, and
  (ii) a second slider input control displayed in association with,
    (A) a label indicating a second health parameter,
    (B) a first pictorial character image displayed proximate a first end of the second slider input control representing a first state of the second health parameter, and
    (C) a second pictorial character image displayed proximate a second, opposite end of the second slider input control representing a second, opposite state of the second health parameter, and
  (iii) a third slider input control displayed in association with,
    (A) a label indicating a third health parameter,
    (B) a first pictorial character image displayed proximate a first end of the third slider input control representing a first state of the third health parameter, and
    (C) a second pictorial character image displayed proximate a second, opposite end of the third slider input control representing a second, opposite state of the third health parameter; and (b) receiving, from the user via touching of the touchscreen display, first user input corresponding to positioning of a slider on the first slider input control;

(c) receiving, from the user via touching of the touchscreen display, second user input corresponding to positioning of a slider on the second slider input control;

(d) receiving, from the user via touching of the touchscreen display, third user input corresponding to positioning of a slider on the third slider input control;

(e) automatically determining, based on the location of the slider on the first slider input control following the first user input, a first health parameter value;

(f) accessing, based on the first health parameter value, a first component pictorial image stored in association with that health parameter value;

(g) automatically determining, based on the location of the slider on the second slider input control following the second user input, a second health parameter value;

(h) accessing, based on the second health parameter value, a second component pictorial image stored in association with that health parameter value;

(i) automatically determining, based on the location of the slider on the third slider input control following the third user input, a third health parameter value;

(j) accessing, based on the third health parameter value, a third component pictorial image stored in association with that health parameter value;

(k) automatically combining the accessed first component pictorial image, the accessed second component pictorial image, and the accessed third component pictorial image to generate the composite pictorial visualization;

(l) displaying, to the user via the touchscreen display, the generated composite pictorial visualization;

(m) communicating the generated composite pictorial visualization from the electronic device for view by others, wherein the generated composite pictorial visualization is displayed to others by way of a social networking application; and (n) displaying on a different electronic device the generated composite pictorial visualization.

12. The method of claim 1, further comprising maintaining a profile of the user.

13. The method of claim 12, wherein the profile includes a medical history of the user.

14. The method of claim 11, further comprising maintaining a profile of the user, wherein the determining of the pictorial visualization is based at least in part on the profile of the user that is maintained.

15. A method for automatically creating a computer-generated composite pictorial visualization based on multivariate health data for a user, the method comprising:

(a) displaying, to a user via a touchscreen display associated with an electronic device, a first graphical user interface including
  (i) a first slider input control displayed in association with,
    (A) a label indicating a first health parameter,
    (B) a first pictorial character image displayed proximate a first end of the first slider input control representing a first state of the first health parameter, and (C) a second pictorial character image displayed proximate a second, opposite end of the first slider input control representing a second, opposite state of the first health parameter, and
(ii) a second slider input control displayed in association with,
  (A) a label indicating a second health parameter,
  (B) a first pictorial character image displayed proximate a first end of the second slider input control representing a first state of the second health parameter, and
  (C) a second pictorial character image displayed proximate a second, opposite end of the second slider input control representing a second, opposite state of the second health parameter, and
(iii) a third slider input control displayed in association with,
  (A) a label indicating a third health parameter,
  (B) a first pictorial character image displayed proximate a first end of the third slider input control representing a first state of the third health parameter, and
  (C) a second pictorial character image displayed proximate a second, opposite end of the third slider input control representing a second, opposite state of the third health parameter; and
(b) receiving, from the user via touching of the touchscreen display, first user input corresponding to positioning of a slider on the first slider input control;
(c) receiving, from the user via touching of the touchscreen display, second user input corresponding to positioning of a slider on the second slider input control;
(d) receiving, from the user via touching of the touchscreen display, third user input corresponding to positioning of a slider on the third slider input control;
(e) automatically determining, based on the location of the slider on the first slider input control following the first user input, a first health parameter value;
(f) accessing, based on the first health parameter value, from a data store containing a plurality of images each associated with a respective value for the first health parameter, a first component pictorial image stored in association with the first health parameter value;
(g) automatically determining, based on the location of the slider on the second slider input control following the second user input, a second health parameter value;
(h) accessing, based on the second health parameter value, from a data store containing a plurality of images each associated with a respective value for the second health parameter, a second component pictorial image stored in association with the second health parameter value;
(i) automatically determining, based on the location of the slider on the third slider input control following the third user input, a third health parameter value;
(j) accessing, based on the third health parameter value, from a data store containing a plurality of images each associated with a respective value for the third health parameter, a third component pictorial image stored in association with the third health parameter value;
(k) automatically combining the accessed first component pictorial image, the accessed second component pictorial image, and the accessed third component pictorial image to generate the composite pictorial visualization;
(l) displaying, to the user via the touchscreen display, the generated composite pictorial visualization;
(m) communicating the generated composite pictorial visualization from the electronic device for view by others, wherein the generated composite pictorial visualization is displayed to others by way of a social networking application; and
(n) displaying on a different electronic device the generated composite pictorial visualization.

* * * * *